US010576456B2

(12) United States Patent
Saavedra et al.

(10) Patent No.: US 10,576,456 B2
(45) Date of Patent: Mar. 3, 2020

(54) SYSTEMS AND METHODS OF PREPARING STABILIZED LIPID ASSEMBLIES

(71) Applicant: ARIZONA BOARD OF REGENTS ON BEHALF OF THE UNIVERSITY OF ARIZONA, Tucson, AZ (US)

(72) Inventors: Steven Scott Saavedra, Tucson, AZ (US); Craig A. Aspinwall, Tucson, AZ (US); Saliya N. Ratnayaka, Tucson, AZ (US); Leonard Bright, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 0 days.

(21) Appl. No.: 15/318,905

(22) PCT Filed: Jun. 30, 2015

(86) PCT No.: PCT/US2015/038539
§ 371 (c)(1),
(2) Date: Dec. 14, 2016

(87) PCT Pub. No.: WO2016/004029
PCT Pub. Date: Jan. 7, 2016

(65) Prior Publication Data

US 2017/0120218 A1 May 4, 2017

Related U.S. Application Data

(60) Provisional application No. 62/018,794, filed on Jun. 30, 2014, provisional application No. 62/018,822, filed on Jun. 30, 2014.

(51) Int. Cl.
*B01J 20/32* (2006.01)
*B01D 69/10* (2006.01)
(Continued)

(52) U.S. Cl.
CPC ......... *B01J 20/3272* (2013.01); *B01J 20/286* (2013.01); *B01J 20/288* (2013.01);
(Continued)

(58) Field of Classification Search
None
See application file for complete search history.

(56) References Cited

U.S. PATENT DOCUMENTS 2,689,242 A * 9/1954 Lucht ...................... C08F 14/06 526/87
3,799,743 A * 3/1974 Alexander ....... G01N 33/48728 422/82.02
(Continued)

FOREIGN PATENT DOCUMENTS

DE 102006039588 A1 * 2/2008 ............ B82Y 30/00
JP 2004309464 A * 11/2004
(Continued)

OTHER PUBLICATIONS

Meier, Polymer nanocapsules, Jul. 2000, Chem. Soc. Review, Issue 29, pp. 295-303 (Year: 2000).*
(Continued)

*Primary Examiner* — Jeffrey A Vonch
(74) *Attorney, Agent, or Firm* — Ngyuen Tarbet

(57) ABSTRACT

Direct polymerization of lipid monomers or polymer scaffolding of non-lipid monomers coupled with irradiation or redox polymerization performed at neutral pH resulted in stabilized lipid assemblies. An initiator-buffer component and NaHS03 redox mixture polymerizes reactive lipid monomers at near neutral pH conditions to preserve functionality of reconstituted membrane proteins. Improved stability of black lipid membranes (BLMs) is attained by chemical cross-linking of polymerizable, hydrophobic and commercially available non-lipid monomers partitioned into
(Continued)

F~H,E~
F~ms~
R
Si
O
Glass substrate
R group
PFDCS
CPDCS the suspended lipid membranes, and by suspending the BLMs across low surface energy apertures. Substrate apertures having low surface energy modifiers with amphiphobic properties facilitated a reproducible formation of BLMs by promoting interactions between the lipid tail and the substrate material. In addition, polymeric lipid bilayer membranes were prepared by photochemical or redox initiated polymerization of polymerizable lipid monomers, and disposed onto supporting substrates for use in chromatography columns.

33 Claims, 36 Drawing Sheets

(51) Int. Cl.

| | |
|---|---|
| ***B32B 3/24*** | (2006.01) |
| ***G01N 33/487*** | (2006.01) |
| ***B82Y 5/00*** | (2011.01) |
| ***B82Y 15/00*** | (2011.01) |
| ***C08F 30/08*** | (2006.01) |
| ***B01J 20/288*** | (2006.01) |
| ***C08F 2/48*** | (2006.01) |
| ***B01J 20/286*** | (2006.01) |
| *B82Y 40/00* | (2011.01) |
| *B32B 3/26* | (2006.01) |
| *G01N 30/52* | (2006.01) |
| *B32B 3/10* | (2006.01) |

(52) U.S. Cl.

CPC ....... *B01J 20/3204* (2013.01); *B01J 20/3219* (2013.01); *B01J 20/3282* (2013.01); *B01J 20/3287* (2013.01); *B01J 20/3289* (2013.01); *C08F 2/48* (2013.01); *C08F 30/08* (2013.01); *B01D 69/10* (2013.01); *B01D 69/105* (2013.01); *B01J 20/3208* (2013.01); *B01J 20/3274* (2013.01); *B32B 3/10* (2013.01); *B32B 3/266* (2013.01); *B32B 2307/20* (2013.01); *B32B 2307/70* (2013.01); *B82Y 5/00* (2013.01); *B82Y 15/00* (2013.01); *B82Y 40/00* (2013.01); *C12Q 2565/631* (2013.01); *G01N 33/48721* (2013.01); *G01N 2030/527* (2013.01); *Y10S 435/975* (2013.01); *Y10T 428/24331* (2015.01)

(56) References Cited

U.S. PATENT DOCUMENTS 4,931,498 A * 6/1990 Pidgeon ................. A61K 9/127 210/656
5,368,712 A * 11/1994 Tomich ................ C07K 14/001 204/403.06
5,443,955 A * 8/1995 Cornell .............. A61B 5/14546 435/317.1
6,019,998 A * 2/2000 Nomoto ............... A61K 9/1271 264/4.32
6,217,901 B1 * 4/2001 Perrott ................. A61K 9/5138 424/450
6,835,393 B2 * 12/2004 Hoffman ............ A61K 41/0028 424/450
6,863,833 B1 * 3/2005 Bloom .................... B81B 1/004 204/403.08
2002/0037986 A1 * 3/2002 Meier .................... A61K 9/009 526/279
2004/0063200 A1 * 4/2004 Chaikof ............... A61K 9/5031 435/317.1
2005/0191616 A1 * 9/2005 Shenoy .................. B01D 61/38 435/4
2005/0244453 A1 * 11/2005 Stucke .................... A61L 27/34 424/423
2006/0014013 A1 * 1/2006 Saavedra ................ A61L 27/34 428/338
2006/0251709 A1 * 11/2006 Ide ................... G01N 33/48728 424/450
2008/0101988 A1 * 5/2008 Kang .............. G01N 33/48721 422/400
2008/0286549 A1 * 11/2008 Pinkhassik ................. C08J 9/26 428/220
2009/0142504 A1 * 6/2009 Ervin ..................... H01B 1/122 427/430.1
2010/0068808 A1 3/2010 Bangera et al.
2010/0196203 A1 * 8/2010 Sanghera ............... G01N 33/92 422/68.1
2010/0320094 A1 * 12/2010 White ............. G01N 33/48721 205/778
2010/0331194 A1 * 12/2010 Turner ................. C12Q 1/6869 506/2
2011/0020950 A1 * 1/2011 Vogel ................... B01D 67/006 436/501
2011/0120890 A1 * 5/2011 Macpherson .... G01N 33/48721 205/792
2012/0114925 A1 * 5/2012 Harnack ................ B01D 69/10 428/216
2013/0146480 A1 * 6/2013 Garaj ............... G01N 33/48721 205/787
2014/0034497 A1 * 2/2014 Davis ............... G01N 27/44791 204/451
2015/0153302 A1 * 6/2015 Davis ............... G01N 33/48721 204/403.08

FOREIGN PATENT DOCUMENTS

JP 2011149868 A * 8/2011
WO WO-9813025 A1 * 4/1998 ............... A61K 8/14
WO WO-2006104639 A2 * 10/2006 ........ B01L 3/502707
WO 2013/180659 A1 12/2013

OTHER PUBLICATIONS

Graff et al., Nanoreactors from Polymer-Stabilized Liposomes, Jan. 2001, 17(3), pp. 919-923 (Year: 2001).*
Kohut-Svelko et al, Redox initiator systems for emulsion polymerization of acrylates, Journal of Polymer Science Part A: Polymer Chemistry, vol. 47, Issue 11, pp. 2917-2927 (Year: 2009).*
Heitz et al., Polymerized Planar Suspended Lipid Bilayers for Single Ion Channel Recordings: Comparison of Several Dienoyl Lipids, Jan. 2011, Langmuir, 27(5), pp. 1882-1890 (Year: 2011).*
Supporting Information, 2013 (no month), Journal of Materials Chemistry BSupporting Information, 2013 (no month), Journal of Materials Chemistry B (Year: 2013).*
Okazaki et al., Creation of a polymer backbone in lipid bilayer membrane-based nanotubes for morphological and microenvironmental stabilization, Jul. 2014 (Year: 2014).*
Israelachvili et al., Physical principles of membrane organization, 1980, Quarterly Reviews of Biophysics, vol. 13, Issue 2, pp. 121-200 (Year: 1980).*
Paul et al., Sodium Metabisulphite Initiated Aqueous Polymerisation of Methyl Methacrylate, Sep. 1982, British Polymer Journal, pp. 105-112 (Year: 1982).*
Murtagh et al., Mobility and reactivity in colloidal aggregates with motion restricted by polymerization, 1986, Faraday Discussions of the Chemical Society, vol. 81, pp. 127-136 (Year: 1986).*
Wu et al, Two-Dimensional Reaction Solvents: Surfactant Bilayers in the Formation of Ultrathin Films, 1987, Langmuir, vol. 3, pp. 531-537 (Year: 1987).*
Gomes et al., Stable Polymethacrylate Nanocapsules from Ultraviolet Light-Induced Template Radical Polymerization of Unilamellar Liposomes, Jul. 2006, Langnnuir,vol. 22, Issue 18, pp. 7755-7759 (Year: 2006).*
Sandison et al., Micromachined glass apertures for artificial lipid bilayer formation in a microfluidic system, Jul. 2007, Journal of Micromechanics and Microengineering, vol. 17, pp. S189-S196 (Year: 2007).*

(56) References Cited

OTHER PUBLICATIONS

White et al, Single Ion-Channel Recordings Using Glass Nanopore Membranes, Sep. 2007, Journal of the American Chemical Society, vol. 129, Issue 38, pp. 11766-11775 (Year: 2007).*
Ota et al., Microfluidic formation of lipid bilayer array for membrane transport analysis, 2008, IEEE 21st International Conference on Micro Electro Mechanical Systems (Year: 2008).*
Peetla et al., Biophysical interactions with model lipid membranes: applications in drug discovery and drug delivery, May 2009, Molecular Pharmaceutics, vol. 6, Issue 5, pp. 1264-1276 (Year: 2009).*
Salvador et al., Buffers May Adversely Affect Model Lipid Membranes: A Cautionary Tale, Oct. 2009, Biochemistry, vol. 48, pp. 11149-11151 (Year: 2009).*
Zagnoni, Miniaturised technologies for the development of artificial lipid bilayer systems, Mar. 2012, Lab on a Chip, vol. 12, pp. 1026-1039 (Year: 2012).*
Wantanabe et al., Continuous exchange of buffers over a lipid bilayer membrane formed in a glass microfluidic device, Jan. 2012, 16th International Conference on Miniaturized Systems for Chemistry and Life Sciences, pp. 395-397 (Year: 2012).*
Hotz et al., Vesicle-Templated Polymer Hollow Spheres, Feb. 1998, Langmuir, vol. 14, Issue 5, pp. 1031-1036 (Year: 1998).*
Wolcke, Julian; Ullmann, Dirk. Drug Discovery Today. 2001, 6, 637-646.
Moaddel, Ruin; Wainer, Irving W. Journal of Pharmaceutical and Biomedical Analysis. 2007, 43, 399-406.
Wiedmer, Susanne K.; Jussila, Minttu S.; Riekkola, Marja-Liisa. Trends in Analytical Chemistry. 2004, 23, 562-582.
Lundahl, Per; Yang, Qing. Journal of Chromatography. 1991, 544, 283-304.
Yang, Qing; Liu, Xue-Ying; Ajiki, Shu-Ichi; Hara, Masayuki, et al. Journal of Chromatography B. 1998, 707, 131-141.
Liu, Xue-Ying; Yang, Qing; Nakamura, Chikashi; Miyake, Jun. Journal of Chromatography B. 2001, 750, 51-60.
Krause, Eberhard; Dathe, Margitta; Wieprecht, Torsten; Bienert, Michael. Journal of Chromatography A. 1999, 849, 125-133.
Proverbio, Davide; Roos, Christian; Beyermann, Michael; Orban, Erika, et al. Biochimica et Biophysica Acta. 2013, 1828, 2182-2192.
Yang, Qing; Lundahl, Per. Biochemistry. 1995, 34, 7289-7294.
Moaddel, R.; Rosenberg, A.; Spelman, K.; Frazier, J., et al. Analytical Biochemistry. 2011, 412, 85-91.
Moaddel, Ruin; Wainer, Irving W. Analytica Chimica Acta. 2006, 564, 97-105.
Ross, Eric E.; Bondurant, Bruce; Spratt, Tony; Conboy, John C., et al. Langmuir. 2001, 17, 2305-2307.
Ross, Eric E.; Rozanski, Lynn J.; Spratt, Tony; Liu, Sanchao, et al. Langmuir. 2003, 19, 1752-1765.
Michel, Roger; Subramaniam, Varuni; McArthur, Sally L.; Bondurant, Bruce, et al. Langmuir. 2008, 24, 4901-4906.
Subramaniam, Varuni; D'Ambruoso, Gemma D.; Hall, Henry K., Jr.; Wysocki, Ronald J., Jr., et al. Langmuir. 2008, 24, 11067-11075.
Subramaniam, Varuni; Alves, Isabel D.; Salgado, Gilmar F. J.; Lau, Pick-Wei, et al. Journal of the American Chemical Society. 2004, 127, 5320-5321.
Taillardat-Bertschinger, Agnes; Carrupt, Pierre-Alain; Barbato, Francesco; Testa, Bernard. Journal of Medicinal Chemistry. 2003, 46, 655-665.
Liu, Hanian; Ong, Shaowei; Glunz, Louis; Pidgeon, Charles. Analytical Chemistry. 1995, 67, 3550-3557.
Barbato, F.; Di Martino, G.; Grumetto, L.; La Rotonda, M. I. European Journal of Pharmaceutical Sciences. 2004, 22, 261-269.
Zhang, Yanxiao; Xiao, Yingxian; Kellar, Kenneth J.; Wainer, Irving W. Analytical Biochemistry. 1998, 264, 22-25.
Beigi, Farideh; Wainer, Irving W. Analytical Chemistry. 2003, 75, 4480-4485.
Moaddel, Ruin; Wainer, Irving W. Nature Protocols. 2009, 4, 197-205.
Gottschalk, Ingo; Lagerquist, Caroline; Zuo, Shu-Sheng; Lundqvist, Andreas; Lundahl, Per. Journal of Chromatography B. 2002, 768, 31-40.
Mansfield, Elisabeth; Ross, Eric E.; Aspinwall, Craig A. Analytical Chemistry. 2007, 79, 3135-3141.
Adem, Seid M.; Mansfield, Elisabeth; Keogh, John P.; Hall, Henry K., Jr.; Aspinwall, Craig A. Analytica Chimica Acta. 2013, 772, 93-98.
Ross, Eric E.; Mansfield, Elisabeth; Aspinwall, Craig A. Journal of the American Chemical Society. 2005, 127, 16756-16757.
Lamparski, Henry; Liman, Ulrich; Barry, Judith A.; Frankel, David A., et al. Biochemistry. 1992, 31, 685-694.
Andreolini, Franca; Borra, Claudio; Novotny, Milos. Analytical Chemistry. 1987, 59, 2428-2432.
Maruska, Audrius; Pyell, Ute. Journal of Chromatography A. 1997, 782, 167-174.
Krause, Kerstin; Girod, Marco; Chankvetadze, Bezhan; Blaschke, Gottfried. Journal of Chromatography A. 1999, 837, 51-63.
Abramoff, M. D.; Magelhaes, P. J.; Am, S. J. Biophotonics International. 2004, 11, 36-42.
Gulcev, Makedonka D.; Lucy, Charles A. Analytical Chemistry. 2008, 80, 1806-1812.
Richter, Ralf P.; Berat, Remi; Brisson, Alain R. Langmuir. 2006, 22, 3497-3505.
Sarac, A. S. Progress in Polymer Science. 1999, 24, 1149-1204.
Funasaki, Noriaki; Ishikawa, Seiji; Neya, Saburo. Langmuir. 2000, 16, 5584-5587.
Baker, C. A.; Bright, L K.; Aspinwall, C. A. Anal. Chem. 2013, 85, 9078-9086.
Kasianowicz, J. J.; Robertson, J. W. F.; Chan, E. R.; Reiner, J. E.; Stanford, V. M. Annu. Rev. Anal. Chem. 2008, 1, 737-766.
Stimberg, V. C.; Bomer, J. G.; Van Uitert, I.; Van Den Berg, A.; Le Gac, S. Small 2013, 9, 1076-1085.
Hirano-Iwata, A.; Oshima, A.; Nasu, T.; Taira, T.; Kimura, Y.; Niwano, M. Supramol. Chem. 2010, 22, 406-412.
Oshima, A.; Hirano-Iwata, A.; Mozumi, H.; Ishinari, Y.; Kimura, Y.; Niwano, M. Anal. Chem. 2013, 85, 4363-4369.
Meier, W.; Graff, A.; Diederich, A.; Winterhalter, M. Phys Chem Chem Phys 2000, 2, 4559-4562.
Hirano-Iwata, A.; Aoto, K.; Oshima, A.; Taira, T.; Yamaguchi, R.-T.; Kimura, Y.; Niwano, M. Langmuir 2010, 26, 1949-1952.
Zhang, H.; Joubert, J. R.; Saavedra, S. S. Adv. Polym. Sci. 2010, 224, 1-42.
White, R. J.; Ervin, E. N.; Yang, T.; Chen, X.; Daniel, S.; Cremer, P. S.; White, H. S. J. Am. Chem. Soc. 2007, 129, 11766-11775.
Bright, L. K.; Baker, C. A.; Agasid, M. T.; Ma, L.; Aspinwall, C. A. ACS Appl. Mater. Interfaces 2013, 5, 11918-11926.
Heitz, B. A.; Jones, L W.; Hall, H. K.; Aspinwall, C. A.; Saavedra, S. S. J. Am. Chem. Soc. 2010, 132, 7086-7093.
Benz, R.; Elbert, R.; Prass, W.; Ringsdorf, H. Eur. Biophys. J. 1986, 14, 83-92.
O'Brien, D. F.; Armitage, B.; Benedicto, A.; Bennett, D. E.; Lamparski, H. G.; Lee, Y.-S.; Srisiri, W.; Sisson, T. M. Acc. Chem. Res. 1998, 31, 861-868.
Daly, S. M.; Heffernan, L. A.; Barger, W. R.; Shenoy, D. K. Langmuir 2005, 22, 1215-1222.
Jeon, T. J.; Malmstadt, N.; Schmidt, J. J. J. Am. Chem. Soc. 2006, 128, 42-43.
Montal, M.; Mueller, P. Proc. Nat. Acad. Sci. USA 1972, 69, 3561-3566.
Plant, A. L. Langmuir 1999, 15, 5128-5135.
Gallagher, E. S.; Adem, S. M.; Bright, L. K.; Calderon, I. A. C.; Mansfield, E.; Aspinwall, C. A. Electrophoresis 2014, 35, 1099-1105.
Glaser, R. W.; Leikin, S. L.; Chernomordik, L. V.; Pastushenko, V. F.; Sokirko, A. I. Biochim. Biophys. Acta 1988, 940, 275-287.
Chernomordik, L. V.; Sukharev, S. I.; Abidor, I. G.; Chizmadzhev, Y. A. Bioelectrochem. Bioenerg. 1982, 9, 149-155.
Lundbaek, J. A. J. Gen. Physiol. 2008, 131, 421-429.
Rudnev, V. S.; Ermishkin, L. N.; Fonina, L.A.; Rovin, Y. G. Biochim. Biophys. Acta 1981, 642, 196-202.
Montal, et al. "Formation of Bimolecular Membranes from Lipid Monolayers and a Study of Their Electrical Properties." Proceedings of the National Academy of Sciences [online], Dec. 1972

(56) References Cited

OTHER PUBLICATIONS

[Retrieved on Sep. 23, 2015], vol. 69, No. 12, pp. 3561-3566, Retrieved from the Internet: <URL: http://www.pnas.org/content/69/12/3561.short>.

Joubert, James R.; Smith, Kathryn A.; Johnson, Erin; Keogh, John P., et al. "Stable, Ligand-Doped, Poly(bis-SorbPC) Lipid Bilayer Arrays for Protein Binding and Detection," ACS Applied Materials & Interfaces, vol. 1, No. 6, 1310-1315, 2009.

Liang, Boying; Ju, Yue; Joubert, James R.; Kaleta, Erin J.; et al. "Label-free detection and identification of protein ligands captured by receptors in a polymerized planar lipid bilayer using MALDI-TOF MS," Anal Bioanal Chem, (2015) 407:2777-2789.

Gallagher, Elyssia S.; Adem, Seid M.; Baker, Christopher A.; Ratnayaka, Saliya N.; et al. "Highly stabilized, polymer-lipid membranes prepared on silica microparticles as stationary phases for capillary chromatography," Journal of Chromatography A, (2015).

Cheng, Zhiliang and Aspinwall, Craig A.. "Nanometre-sized molecular oxygen sensors prepared from polymer stabilized phospholipid vesicles," Analyst, 2006, 131,236-243.

Roberts, David L.; Ma, Yaning; Bowles, Steven E.; Janczak, Colleen M.; et al. "Polymer-Stabilized Phospholipid Vesicles with a Controllable, pH-Dependent Disassembly Mechanism," Langmuir 2009, 25, 1908-1910.

Gallagher, Elyssia S.; Mansfield, Elisabeth; Aspinwall, Craig A.. "Stabilized phospholipid membranes in chromatography: toward membrane protein-functionalized stationary phases," Anal Bioanal Chem (2014) 406:2223-2229.

Alberts B, Johnson A, Lewis J, et al. Molecular Biology of the Cell. 4th edition. New York: Garland Science; 2002. National Center for Biotechnology Information; website; accessed on Jun. 18, 2014; http://www.ncbi.nlm.nih.gov/books/NBK26871/.

* cited by examiner

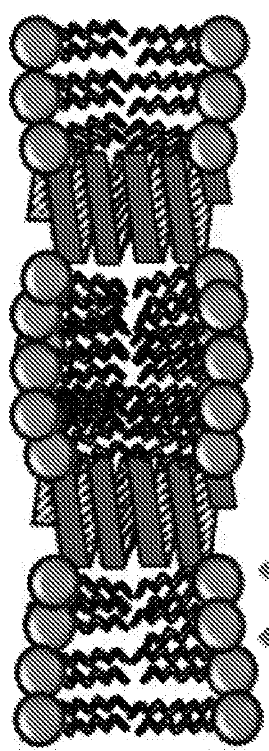
FIG. 4A
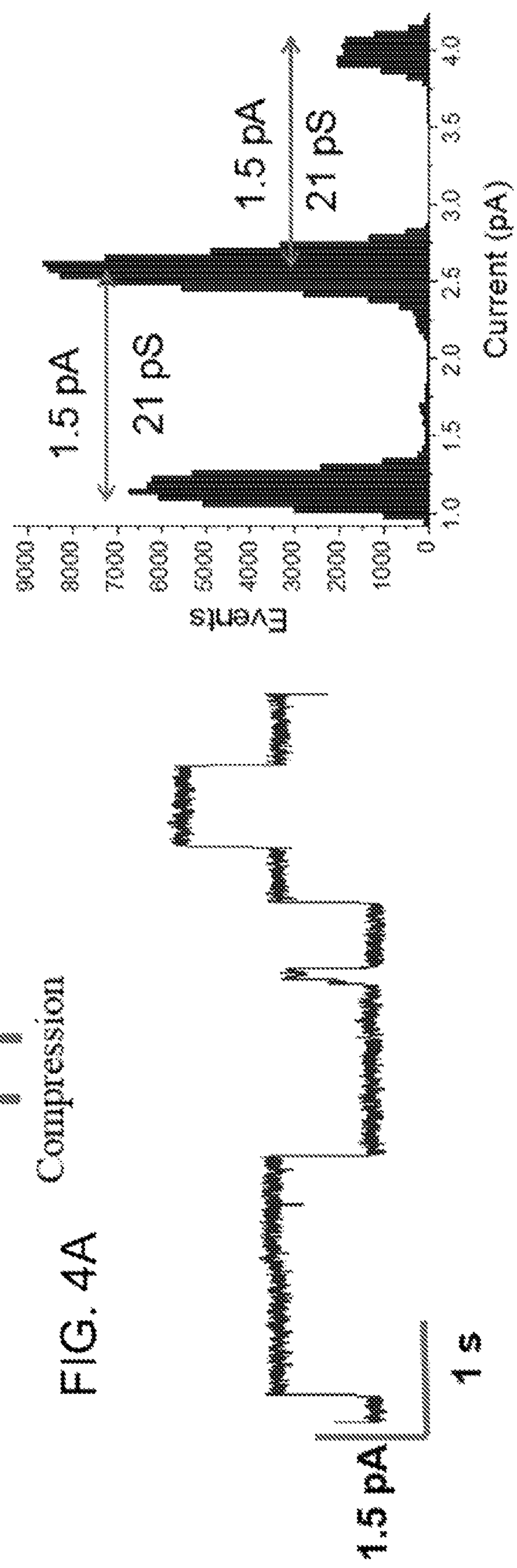
FIG. 4B
FIG. 4C

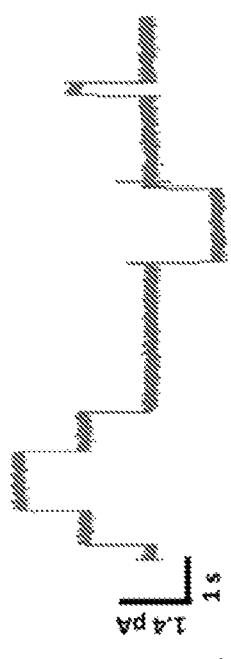
FIG. 5A
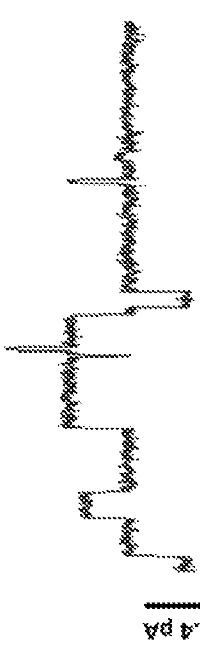
FIG. 5B
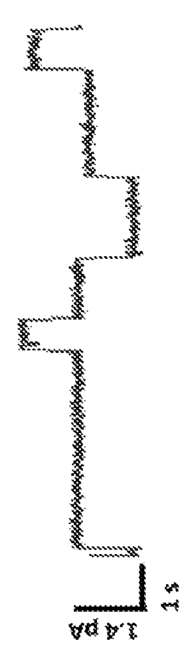
FIG. 5C
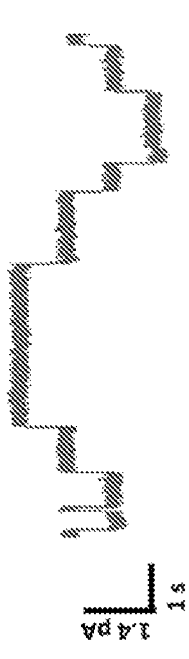
FIG. 5D
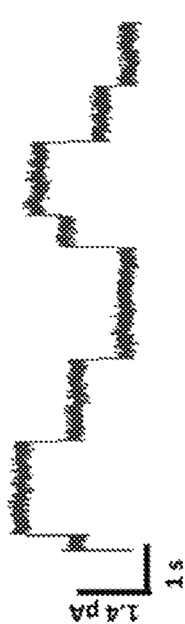
FIG. 5E
FIG. 5F
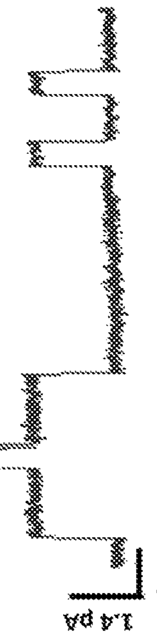
FIG. 5G
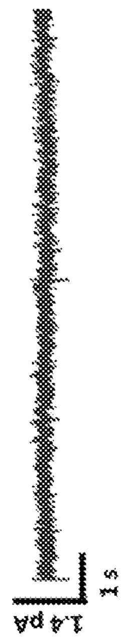
FIG. 5H

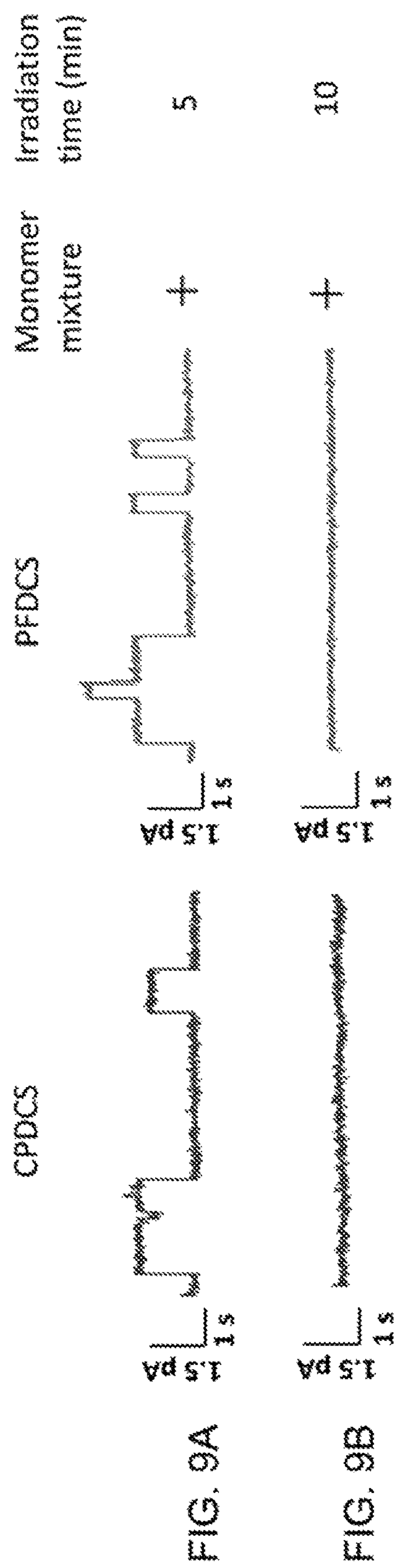
FIG. 9A
FIG. 9B
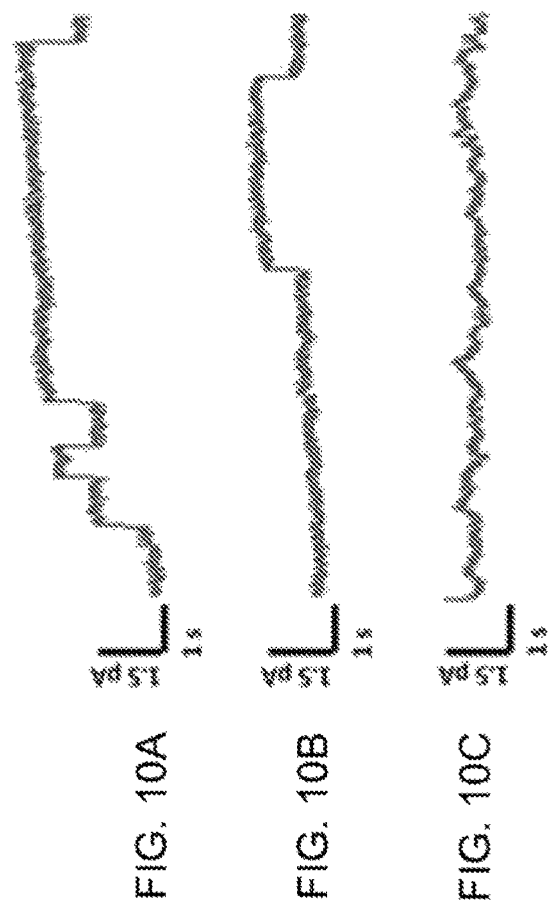
FIG. 10A
FIG. 10B
FIG. 10C

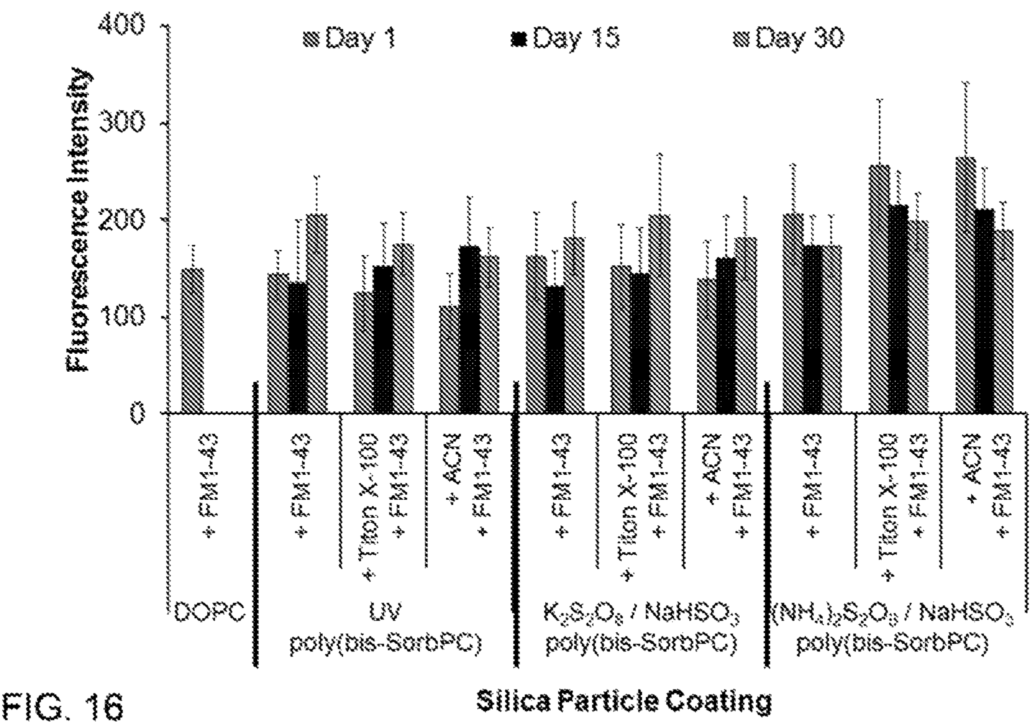
FIG. 16
FIG. 17A
FIG. 17B
FIG. 17C
FIG. 17D
FIG. 17E
FIG. 17F
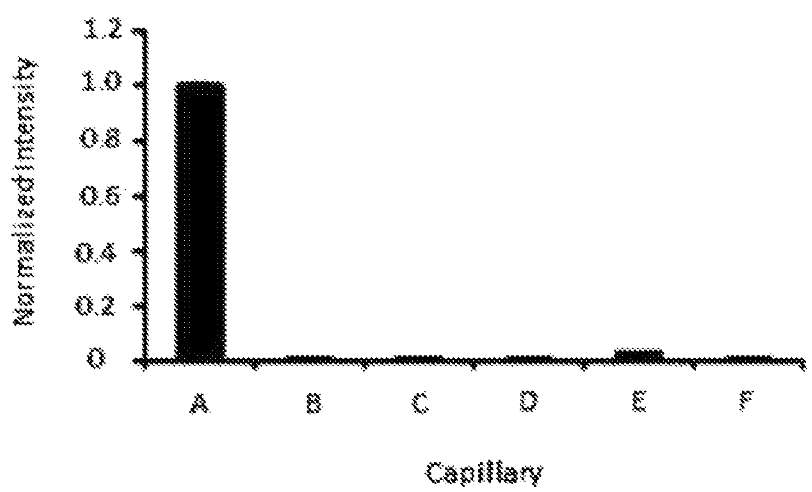
FIG. 17G

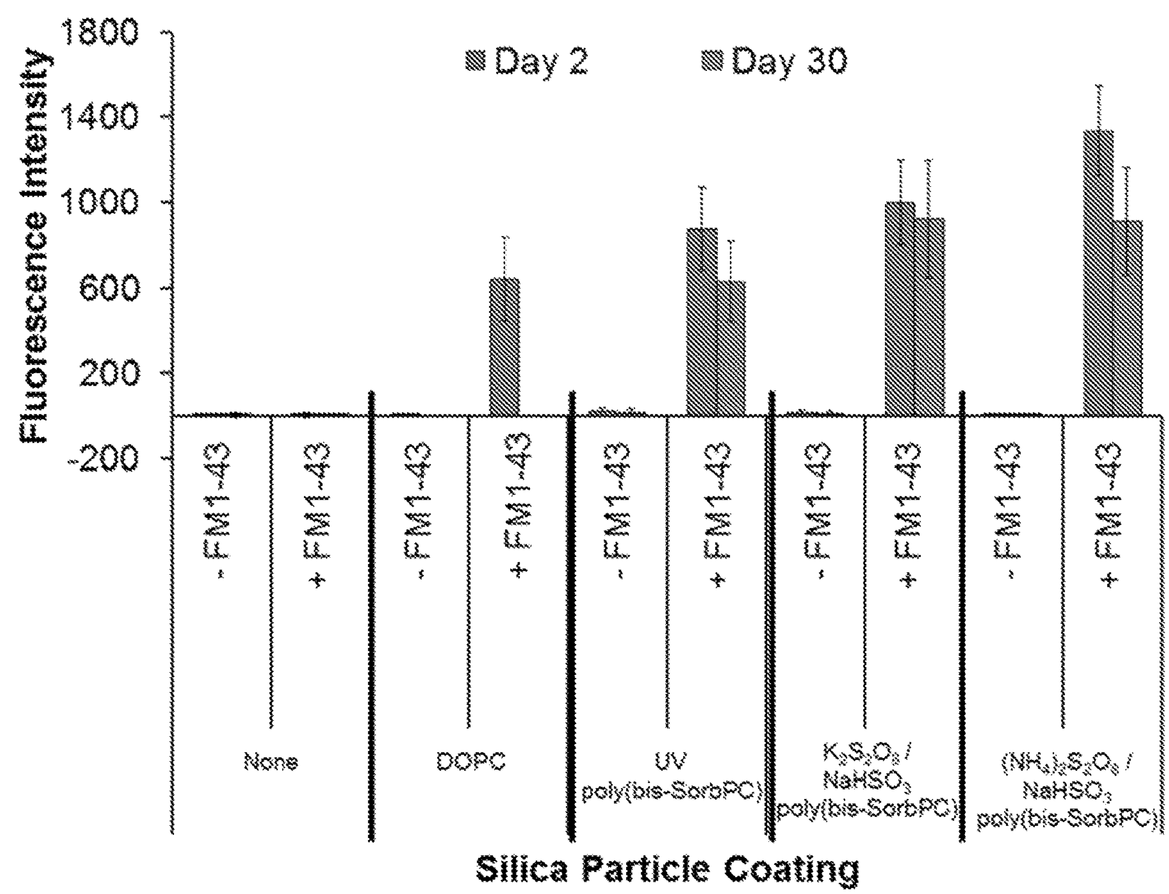
FIG. 19
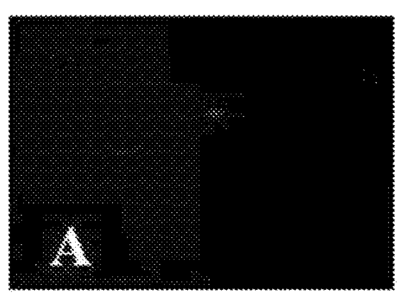
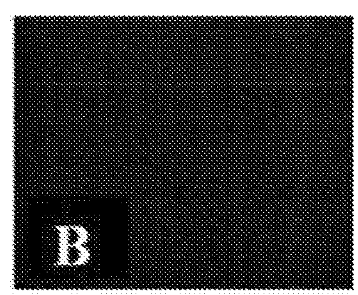
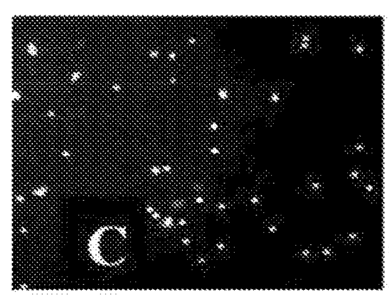
FIG. 20A FIG. 20B FIG. 20C

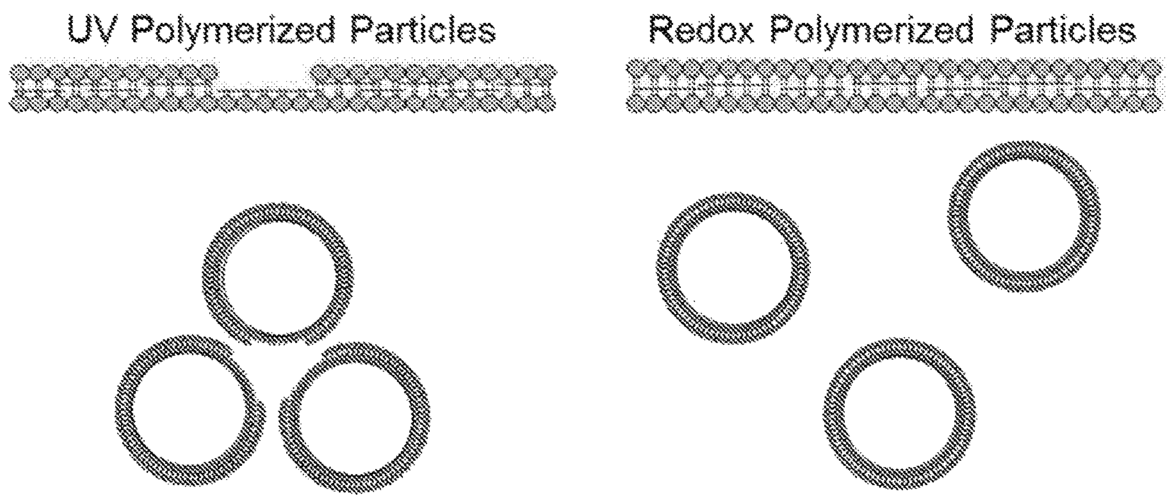
FIG. 21A
FIG. 21B
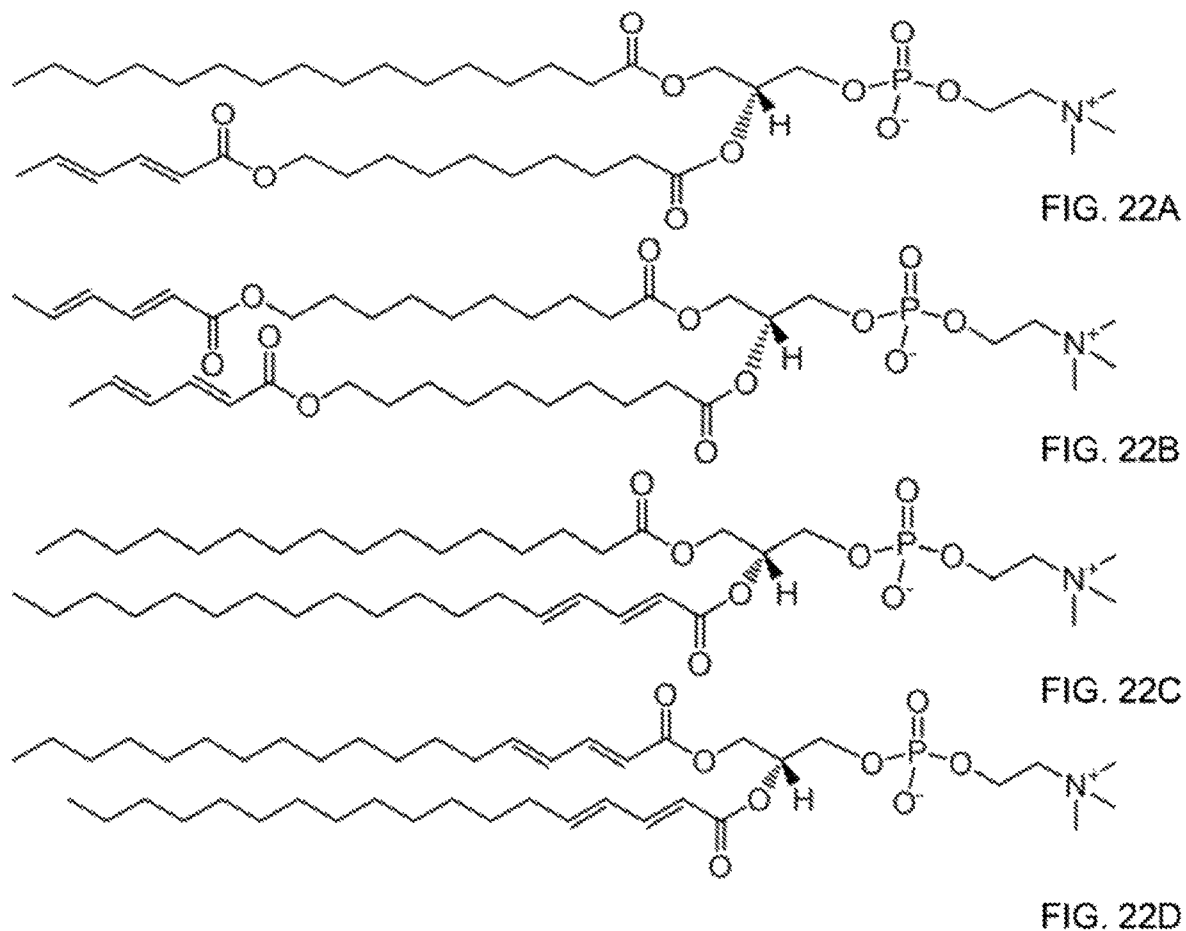
FIG. 22A
FIG. 22B
FIG. 22C
FIG. 22D

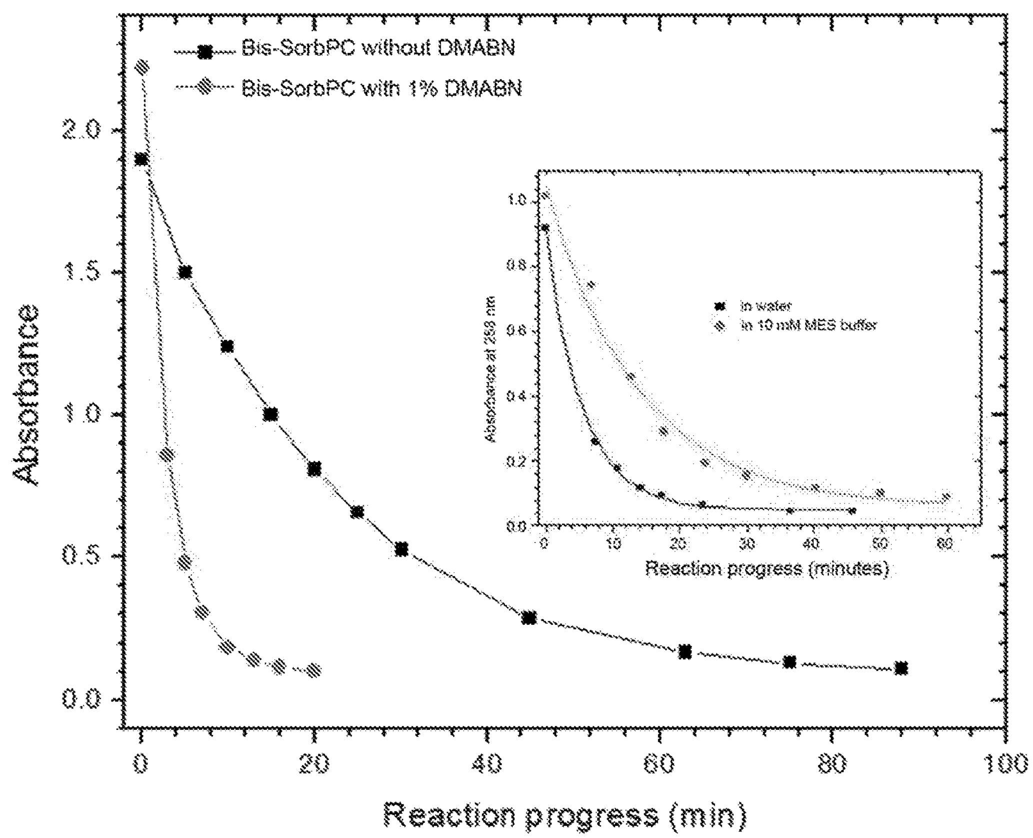
FIG. 23A
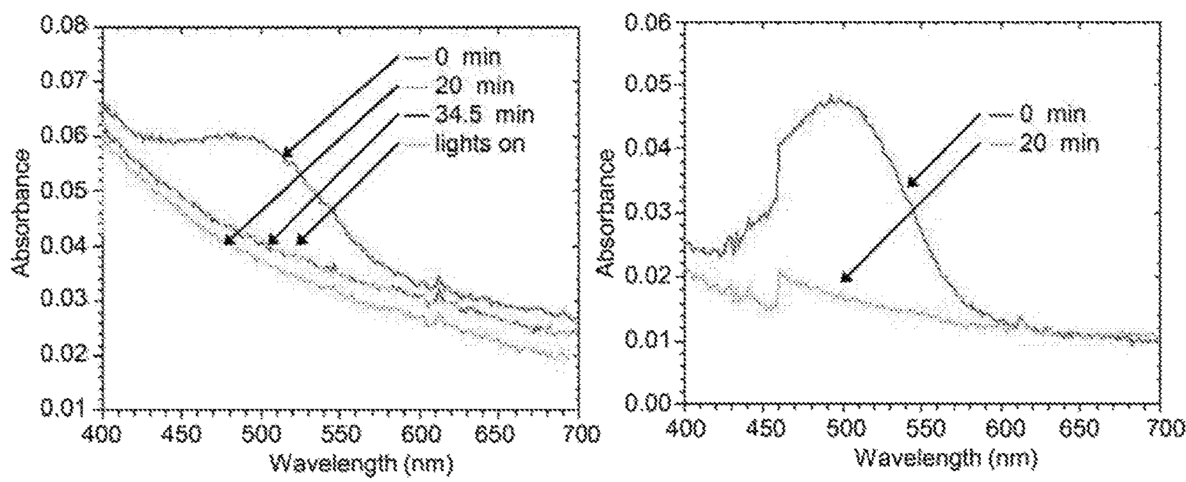
FIG. 23B
FIG. 23C

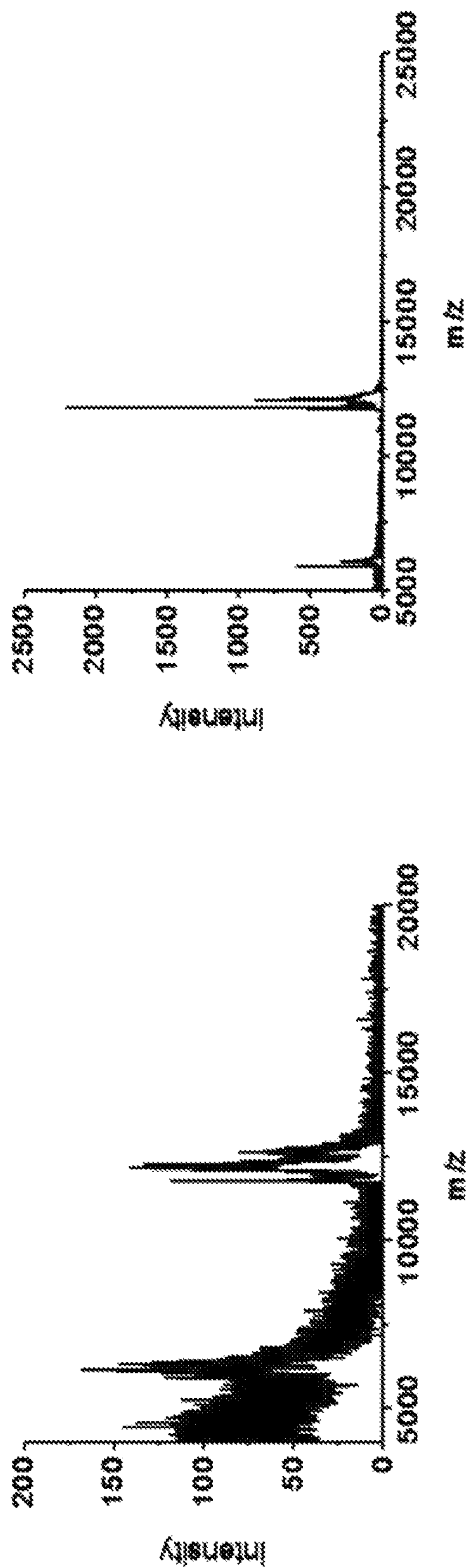
FIG. 44B
FIG. 44A
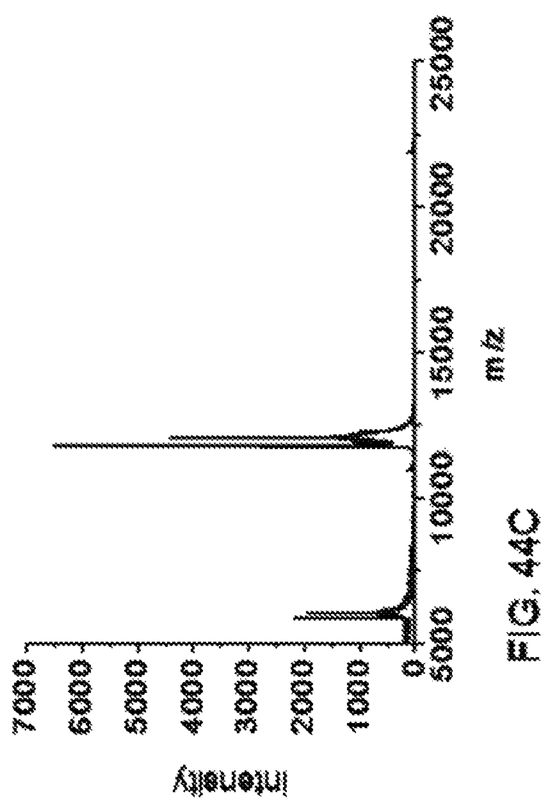
FIG. 44C

SYSTEMS AND METHODS OF PREPARING STABILIZED LIPID ASSEMBLIES

CROSS REFERENCE

This application claims priority to U.S. Provisional Patent Application No. 62/018,794 filed Jun. 30, 2014 and U.S. Provisional Patent Application No. 62/018,822 filed Jun. 30, 2014, the specifications of which are incorporated herein in their entirety by reference.

GOVERNMENT SUPPORT

This invention was made with government support under Grant Nos. T32 GM008804, RO1 GM095763 and RO1 EB007047 awarded by NIH and CHE0518702, awarded by NSF. The government has certain rights in the invention.

FIELD OF THE INVENTION

The present invention relates to systems and methods of preparing lipid assemblies for enhancing stability, in particular, systems and methods for stabilizing synthetic and natural phospholipid membranes using direct polymerization of lipid monomers or polymer scaffolding of non-lipid monomers.

BACKGROUND OF THE INVENTION

Section 1

Suspended lipid bilayers, also known as Black lipid membranes (BLMs), are a model system used to study the function and activity of transmembrane proteins, engineered proteins, phospholipid organization, and as a key component of ion channel-based biosensors. Ion channels (IC) possess a number of desirable properties that make them useful for analytical applications, including ion selectivity, chemical or mechanical gating, inherent signal amplification, well-defined open and closed states and simple electrical readout. BLMs provide an important synthetic membrane environment to study the function and activity of ion channels and serve as key components of ion channel-functionalized analytical platforms.

Additionally, BLMs have potential in high-throughput applications, including drug screening, due to the formation of an array of BLM-IC-based biosensors. A major limitation of BLM-based platforms (i.e. ion channel-functionalized sensor platforms) is the ability to form membranes with adequate electrical, mechanical and temporal stability. BLM instability arises from the relatively weak noncovalent forces of interaction between lipid molecules in the membrane, which are insufficient to maintain the structure of BLMs under mechanical, chemical and electrical stresses. Further, the interaction forces between the lipid membrane and the underlying substrate significantly affect the temporal stability of BLMs.

The development of robust BLMs has been a major focus of research efforts. A few of the methods developed to enhance the formation and stability of BLMs include; miniaturization of aperture size, reducing the surface energy of aperture substrates, sandwiching the BLM between hydrogel layers, and chemical cross-linking by photopolymerization of reactive amphiphiles. Benz et al. pioneered the direct polymerization of lipid membranes as a method of stabilizing BLMs, and identified lipid compositions for developing synthetic ion channel-functionalized sensors (Benz, R.; Elbert, R.; Prass, W.; Ringsdorf, H. *Eur. Biophys. J.* 1986, 14, 83-92). Reactive chemical functionalities can be introduced in the structure of lipid amphiphiles during synthesis to allow cross-linking at the lipid head group, the middle or the distal end of the lipid tail, or via a linker attached to the lipid head group. The degree of cross-linking in polymeric membranes depends on the type of polymerizable lipid and method of polymerization used, and affects the fluidity and stability of the lipid membranes. While polymerization can significantly enhance the stability of BLMs, stiff, viscous polymeric membranes may inhibit the function of some ICs.

A number of approaches have been explored to address the challenge of creating stable membranes that retain fluidity. Schmidt and coworkers created stable long lived BLM platforms for single-channel measurements by encapsulating a pre-existing free-standing membrane within a gel polymerized around it in situ (Jeon, T. J.; Malmstadt, N.; Schmidt, J. J. *J. Am. Chem. Soc.* 2006, 128, 42-43). Although the lifetime of BLM was greatly enhanced, the method reduces the effective diffusion of IC into BLM by ca. 70%, thus increasing IC reconstitution time and making application of the method for sensor development impractical. BLMs have been prepared from mixtures of polymerizable and nonpolymerizable phospholipids which allowed adequate fluidity to observe normal ion channel activity. Shenoy and co-workers reported improved bilayer lifetime using a mixture of polymerizable and non-polymerizable lipids (Daly, S. M.; Heffernan, L. A.; Barger, W. R.; Shenoy, D. K. *Langmuir* 2005, 22, 1215-1222). They observed wide fluctuations in the lifetime of UV irradiated BLMs due to variation in the amount of reactive polymerizable lipids that formed the BLM. To address the challenge of membrane fluidity, Heitz et al demonstrated the preparation of highly stable BLMs from a mixture of polymerizable (bis-dienoyl phosphatidylcholine) and nonpolymerizable (1,2-diphytanoyl-sn-glycero-3-phosphocholine (DPhPC)) phospholipids, a mixture that retained sufficient fluidity for reconstitution and proper function of ion channels and allowed for observation of normal IC activity (Heitz, B. A.; Jones, I. W.; Hall, H. K.; Aspinwall, C. A.; Saavedra, S. S. *J. Am. Chem. Soc.* 2010, 132, 7086-7093). Meier et al. used a different approach to enhance the electrical stability of free standing lipid membranes, in which BLMs were formed from a mixture of nonpolymerizable lipids and nonlipid hydrophobic monomers consisting of polymerizable styrene and divinylbenzene (Meier, W.; Graff, A.; Diederich, A.; Winterhalter, M. *Phys Chem Chem Phys* 2000, 2, 4559-4562). Despite the enhanced electrical stability of BLMs after UV-initiated polymerization, the longevity of the BLMs, fluidity and compatibility with ion channel reconstitution were not investigated.

Here, the present invention features a simple and cost effective method of improving the stability of BLMs from a mixture of nonpolymerizable lipids and commercially available, hydrophobic polymerizable monomers (i.e. methacrylate monomers) that partition into the lamella region of the lipid bilayer. BLMs prepared in equimolar mixture with nonlipid, hydrophobic monomers (BMA and EDGMA) were evaluated for their electrical, mechanical and physical properties before and after UV photopolymerization. The present invention shows dramatically enhanced BLM stability and maintenance of incorporated ion channel activity.

Section 2

Phospholipid membranes play key roles in the regulation of biological function by serving as a barrier between the extracellular and intracellular environments, as well as in the evaluation of physiological and pharmaceutical modulators of biological function. Additionally, phospholipid membranes provide a suitable chemical environment for expression and solubilization of transmembrane proteins. Due to the importance of phospholipid membranes in biological function, many pharmaceutical modulators interact with the macromolecular assemblies either via direct partitioning into the membrane or through interactions with transmembrane proteins.

Current drug screening assays commonly utilize intact cells to identify novel small molecule agonists and antagonists that interact directly with membranes or, more specifically, transmembrane proteins. Unfortunately, cell-based assays suffer from irreproducibility due to variability among heterogeneous cell populations, exhibit false positives and false negatives due to non-specific interactions, and are difficult to interpret due to the complexity associated with monitoring downstream effects of signal transduction. In contrast, affinity chromatography platforms that integrate phospholipid membranes present a unique capability for identifying compounds that interact directly with the membrane or with integrated membrane proteins. Additionally, membrane-functionalized affinity platforms tend to minimize non-specific interactions.

Phospholipid membrane-functionalized affinity stationary phases have been utilized in chromatography to study partitioning and binding interactions. In immobilized liposome chromatography (ILC), liposomes are retained on a support matrix through steric, hydrophobic, covalent, avidin-biotin, or other types of specific or non-specific interactions. ILC has been primarily used to study small molecule partitioning through lipid membranes and interactions between peptides and phospholipids. Various membrane proteins have been immobilized in ILC stationary phases and used to study ligand binding; however, the liposomes are formed by non-covalent interactions, which are inherently unstable. Thus, the stationary phases have limited lifetimes, as well as reduced pressure stability, requiring low flow rates that reduce separation efficiency. Furthermore, ILC phases lack the chemical and mechanical stability to withstand variations in solution conditions (e.g. small fractions of organic solvents, varying ionic strength, etc.) and physical and mechanical insults (air bubbles, shear forces, etc.), decreasing the reproducibility of the columns and limiting their utility.

Immobilized artificial membranes (IAMs) provide an alternative chromatographic stationary phase that exhibits greater stability and reproducibility than ILCs. IAMs are prepared by covalent attachment of lipid tails to an underlying support, resulting in formation of a lipid monolayer on the particle surface. IAMs have been used to study partitioning and interactions between small molecules and phospholipids. Additionally, nicotinic acetylcholine receptors, μ and κ opioid receptors, and other membrane proteins were separately immobilized in IAMs and packed into columns. Using frontal chromatography, dissociation constants for the various membrane proteins were calculated against a series of small molecules, revealing similar trends to binding constants calculated using cell-based assays. However, there were quantitative differences, likely due to the altered conformation of membrane proteins upon interaction with the underlying silica support and the truncated lipid membrane.

Affinity chromatographic matrices for analyzing membrane proteins and molecules that interact with them would benefit from the presence of a more stable lipid structure that more accurately represents a lipid bilayer to allow incorporation of a larger number of membrane proteins, while maintaining their native conformations. Bilayer stability can be increased by a number of methods, such as incorporating cholesterol, adsorbing a protective overlayer, membrane tethering, and polymerizing phospholipid monomers. Of these methods, direct polymerization of phospholipid monomers yields the most stable structures.

Polymerizable phospholipids have been used in various analytical platforms to form stable phospholipid bilayers. As a non-limiting example, planar supported lipid bilayers (PSLBs) prepared by polymerizing bis-SorbPC (1,2-bis[10-(2',4'-hexadieoyloxy)decanoyl]-sn-glycero-2-phosphocholine) have exhibited stability against surfactants, organics, and exposure to high vacuum. Polymerized bis-SorbPC (poly(bis-SorbPC)) membranes have also been utilized in capillary zone electrophoresis as stable surface coatings for reducing the electro-osmotic flow and minimizing non-specific adsorption of proteins. These polymerized surface coatings were stable to surfactant solutions, shear forces, applied electric fields, and dry storage. Additionally, Rhodopsin, a transmembrane protein, was incorporated into PSLBs prepared from poly(bis-SorbPC) and retained its activity in the stabilized bilayer. When combined, these data support further investigation of polymeric lipid bilayers for enhancing stability of phospholipid-based stationary phases and the utility of the resulting polymeric lipid stationary phases for chromatographic separations.

Though polymeric-lipid coatings have been used to minimize non-specific adsorption of proteins in a range of materials, to the knowledge of the inventors, polymeric-lipid membranes have not yet been utilized as a stationary phase material in packed columns. The present invention features a method of preparing poly(bis-SorbPC) coatings onto silica particles that were subsequently packed into capillary LC columns. The chemical, physical, and temporal stability of the polymerized-phospholipid bilayers were assessed and their utility as a lipid-based stationary phase for liquid chromatography is demonstrated.

Polymer lipid membranes can be prepared by photochemical or redox initiated polymerization of synthetic, polymerizable lipid. The resulting polymerized stationary phases exhibited enhanced stability compared to particles coated with non-polymerizable lipid bilayers when exposed to chemical and physical assaults over a period of time. However, a drawback to redox polymerization is that initiation and progression of the polymerization using conventional redox mixtures proceed only under acidic conditions, which poses a problem for proteins incorporated into the lipid bilayer membrane. For example, transmembrane proteins often get denatured, and activities of these proteins can diminish or disappear after redox polymerization with current redox mixtures. Hence there is a need for redox mixtures that provide milder conditions when used in the polymerization of lipids. The present invention features a redox mixture that allows for polymerization methods to proceed under neutral pH conditions while preserving the proteins incorporated into the polymerized lipid membrane.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY OF THE INVENTION

Section 1

Black lipid membranes (BLMs) provide a synthetic environment that facilitates measurement of ion channel activity in diverse analytical platforms. For example, the development of next-generation transmembrane protein-based biosensors relies heavily on the use of BLMs. BLMs instability resulting in rupture within hours (<4 h) of formation poses a significant challenge to biosensor development. Enhanced temporal, mechanical, and electrical stability of BLMs is needed to support the development of membrane-based biosensors and other highly stable measurement platforms.

Suspended lipid bilayers formed across glass apertures are greatly affected by the surface energy of the underlying substrate. Thus, glass pipette apertures were modified with silanes that define the surface energy of the underlying substrate, which affects the stability of the suspended lipid bilayer. The silanized microapertures typically form a hybrid bilayer membrane (HBM) with the phospholipid by adsorption through the assembly of the lipid monolayer on the hydrophobic substrate. The assembly of a lipid monolayer oriented in a tail-down configuration is due to van der Waals and hydrophobic forces of interaction between the hydrophobic lipid tails and the hydrophobic monolayer of the substrate.

When suspended across a decreased energy surface of a silanized aperture, the enhanced stability of BLMs may be due to the amphiphobic ($H_2O$/oil repellency) character induced by PFDCS modifiers on the surface of aperture substrates. The force of interaction between the lipid membrane and the substrate ($F_{MS}$) enhanced the electrical and mechanical stability of the BLMs by 5 and >25 fold respectively in comparison to conventional 3-cyanopropyldimethylchlorosilane (CPDCS) pipette apertures.

Despite the substantial increase in the stability of BLMs that were suspended across decreased energy surfaces of apertures, the inherent weak hydrophobic force of interaction between the self-assembled lipid molecules ($F_H$) and electrostatic forces ($F_E$) limits the average lifetime of the BLMs to ca 8±1 h. To overcome the weak hydrophobic forces, small polymerizable hydrophobic monomers (butylmethacrylate (BMA) and ethylene glycol dimethacrylate (EGDMA) were introduced into the BLMs. Diethoxyacetophenone (DEAP) was used to initiate the chemical cross-linking of the monomers by UV activation. The extent of cross-linking in the monomer doped BLMs was monitored by measuring the electrical and physical properties of the membranes before and after UV irradiation.

One embodiment of the subject disclosure features chemically modified aperture surfaces and chemical cross-linking within the lipid membrane to dramatically improve BLM stability. Glass microapertures were modified using PFDCS. The amphiphobic property ($H_2O$/oil repellency) of the perfluorinated surfaces facilitated the rapid formation of highly stable BLMs. Perfluorinated patch pipettes showed decreased background capacitance and ionic conduction by 83% and 77% respectively, compared to unmodified pipettes. The reduced background current led to 48% noise reduction compared to conventional pipettes.

Another embodiment features photopolymerization of EGDMA and BMA partitioned into lipid membranes composed of 1, 2-diphytanoyl-sn-glycero-3-phosphocholine (DPhPC) to create a cross-linked polymer scaffold in the bilayer lamella for further improving BLM stability. The commercially available methacrylate monomers provide a simple, low cost, and broadly accessible approach for preparing highly stabilized BLMs used for ion channel analytical platforms. As a non-limiting example, when prepared on silane-modified glass microapertures, the resulting polymer scaffold-stabilized (PSS)-BLMs exhibited significantly improved lifetimes of 23±9 to 40±14 h and >10-fold increase in mechanical stability, with breakdown potentials >2000 mV attainable, depending on surface modification and polymer cross-link density. Additionally, the polymer scaffold exerted minimal perturbations to membrane electrical integrity as indicated by mean conductance measurements. When gramicidin A and α-hemolysin were reconstituted into PSS-BLMs, the ion channels retained function comparable to conventional BLMs.

Overall, cross-linked BLMs suspended on perfluorinated apertures exhibited significantly improved lifetimes (>24 h), 25-fold increase in mechanical stability, 50% increase in electrical resistance, and 53% increase in electrical stability. The present invention demonstrates key advances in the formation of stabilized BLMs and can be amenable to a wide range of receptor and ion channel functionalized platforms.

Section 2

The capability to rapidly screen complex libraries of pharmacological modulators is paramount to modern drug discovery efforts. This task is particularly challenging for agents that interact with lipid bilayers or membrane proteins due to the limited chemical, physical, and temporal stability of traditional lipid-based stationary phases in affinity chromatography. The present invention features the preparation of liquid chromatography (LC) columns using a novel stationary phase prepared from highly stable, polymeric phospholipid bilayers assembled onto silica micro-particles.

Polymer lipid membranes were prepared by photochemical or redox initiated polymerization of 1,2-bis[10-(2',4'-hexadieoyloxy)decanoyl]-sn-glycero-2-phosphocholine (bis-SorbPC), a synthetic, polymerizable lipid. The resulting polymerized bis-SorbPC (poly(bis-SorbPC)) stationary phases exhibited enhanced stability compared to particles coated with non-polymerizable lipid 1,2-dioleoyl-sn-glycero-phosphocholine (DOPC) bilayers when exposed to chemical (organic solvents and surfactants) and physical (shear forces) insults over a 30 day period. Further, poly (bis-SorbPC)-coated particles could be packed into the column using slurry packing with no degradation of the lipid bilayer, compared to unpolymerized lipid membranes where the lipid bilayer was removed during packing. Frontal chromatographic analyses of acetylsalicylic acid, benzoic acid, and salicylic acid using poly(bis-SorbPC)-coated microspheres showed increased retention times compared to bare silica microspheres ($P<0.0001$), supporting that the lipophilic molecules were retained on the polymerized phospholipid bilayer stationary phases. The capability to prepare highly stabilized phospholipid membranes that withstand typical capillary LC conditions should greatly expand the range of applications utilizing lipid membrane-functionalized separations.

The present invention features a mixture of redox initiators, comprising an initiator-buffer component and $NaHSO_3$, that is surprisingly is effective to polymerize lipid bilayer membranes, such as bis-SorbPC vesicles, at slightly acidic or near neutral pH solutions. Without wishing to limit the invention to any particular theory or mechanism, it is believed that one of the features that facilitates for this effectiveness is the use of ammonium persulfate (AP, $(NH_4)_2S_2O_8$) as the initiator-buffer component. Most importantly, the ammonium persulfate and $NaHSO_3$ redox mixture shows the ability to generate radicals at near neutral pH, surprisingly converts 90+% of monomers to polymers in about an hour, and is mild enough to prevent denaturation of transmembrane proteins, such as Rhodopsin. For example, both Rhodopsin incorporated directly and in rod outer segment (ROS) membranes with bis-SorbPC show retention of activity after the polymerization of poly(bis-SorbPC) vesicles. In addition, the poly(bis-SorbPC) vesicles polymerized with the AP/$NaHSO_3$ redox mixture show stability similar to or better than that of cross-linked polymerized lipid bilayers prepared with conventional redox mixtures such as $K_2S_2O_8$/$NaHSO_3$. Another advantageous property of the ammonium persulfate and $NaHSO_3$ redox mixture is that it does not have undesirable spectroscopic properties that mask the structural information of the protein/lipid assembly.

As far as the inventors are aware, the prior arts and conventional redox mixtures do not teach or suggest a redox mixture for polymerizing lipid monomers and having an initiator-buffer component that functions as both an initiator and buffer, that is capable of generating radical species and maintaining near neutral pH conditions, and that does not interfere with redox chemistry and protein activity. For example, the prior art generally teaches a redox mixture comprising as $K_2S_2O_8$/$NaHSO_3$, which causes acidic conditions that can denature proteins.

BRIEF DESCRIPTION OF THE DRAWINGS

The features and advantages of the present invention will become apparent from consideration of the following detailed description presented in connection with the accompanying drawings in which:

FIG. 4A shows a schematic representation of the interaction between a hydrophobic membrane protein and a lipid bilayer membrane, specifically, gramicidin A activity in conventional (unpolymerized) suspended lipid bilayers. Bilayer compression is required to facilitate gramicidin pore formation. The figure shows the deformation of the lipid bilayer owing to a thicker lipid membrane than the length of the functional dimer of gramicidin.

FIG. 4B shows gating or ion transport through gramicidin A reconstituted in a BLM. FIG. 4B shows a representative trace of gramicidin ion current in a conventional BLM with an applied potential of 70 mV at which characteristic gating activity occurs.

FIG. 4C shows an all-points histogram of the current trace shown in FIG. 4B. FIG. 4C shows quantized conductance states separated by ca. 21 pS, which is a characteristic of gramicidin ion channels in conventional BLMs.

FIG. 5A shows ion channel activity of gramicidin A reconstituted into DPhPC.

FIG. 5B shows ion channel activity of gramicidin A reconstituted into DPhPC after 5 minutes of UV irradiation.

FIG. 5C shows ion channel activity of gramicidin A reconstituted into DPhPC after 10 minutes of UV irradiation, which showed no significant change in conductance or mean open time for the ion channels (IC). The active channels observed in only pure DPhPC showed multiple conductance states with the number of active channels >4.

FIG. 5D shows ion channel activity of gramicidin A reconstituted into a monomer doped DPhPC BLM without UV irradiation. A slight decrease in conductance is observed.

FIG. 5E shows ion channel activity of gramicidin A reconstituted into a monomer doped DPhPC BLM after UV irradiation for 5 minutes. There is a mixture of low and high conductance states (11-20 pS) of the IC.

FIG. 5F shows further UV irradiation at 10 minutes of gramicidin A reconstituted into a monomer doped BLM led to 55% lost in conductance.

FIG. 5G shows UV irradiation of a monomer doped BLM for 5 minutes before incubation and reconstitution. There is no deleterious effect on the conductance of the IC.

FIG. 5H shows UV irradiation of a monomer doped BLM for 10 min before incubation and reconstitution. There is no quantized change in current due to lack of fluidity in the bilayer. The result agreed with the observed 55% decrease in conductance when the IC was reconstituted in the bilayer before UV irradiation for 10 min. The significant decrease in conductance suggests decreasing fluidity in the membrane, thus affecting the free diffusion of IC monomers in bilayer leaflet.

FIG. 7A shows a glass pipette aligned orthogonal to a glass bead. FIG. 7B shows the pipette barely touching the glass bead. FIG. 7C shows mild heating of the glass bead fuses glass to the pipette. FIG. 7D shows a fused opening of the glass pipette aligned vertically with the glass bead to facilitate fire polishing. FIG. 7E shows the pipette that is fire polished to a desired diameter. FIG. 7F shows a schematic of CPDCS- or PFDCS-modified glass pipette aperture with lower surface energy that allows for a lipid monolayer to deposit on opposite sides of aperture to form a BLM.

FIG. 8D shows gramicidin activity in methacrylate-doped BLMs (MA-BLMs). FIG. 8E shows gramicidin activity in PSS-BLMs formed via 5 min of UV irradiation. FIG. 8F shows PSS-BLMs formed via 10 min of UV irradiation.

FIGS. 9A-9B show representative single-channel recordings of gramicidin A incubated in pre-formed PSS-BLMs suspended across CPDCS-(blue) and PFDCS-(red) modified apertures. FIG. 9A shows gramicidin retains proper function when reconstituted in pre-formed PSS-BLMs polymerized via 5 min of UV irradiation. FIG. 9B shows incubation of gramicidin in pre-formed PSS-BLMs via 10 min of UV irradiation with no evidence of ion channel reconstitution.

FIGS. 10A-10C show gramicidin A activity in pre-formed PSS-BLMs. FIG. 10A shows that ion channel activity is maintained 5 h after reconstitution with a slight drift in baseline and peak current. FIG. 10B shows activity of ion channel decreases after 7 h and FIG. 10C shows loss of channel activity after 9 h of reconstitution.

FIG. 16 shows long-term stability of lipid bilayer coatings on silica particles measured by fluorescence microscopy using FM1-43 as a membrane stain. UV, $K_2S_2O_8/NaHSO_3$, and $(NH_4)2S_2O_8/NaHSO_3$ refer to the method used for polymerization of bis-SorbPC. Particles were exposed to surfactant (triton X-100) or organic solvent (ACN), washed, and stained with FM1-43 before imaging. For all poly(bis-SorbPC)-coated particles the maintained fluorescence after exposure to chemical insults over a 30 day period illustrates that the polymerized bilayer coatings are temporally stable. Particles were stored dispersed in PBS at 4° C. between timepoints.

FIGS. 17A-17F show fluorescent images of capillaries (75 μm i.d., 360 μm o.d.) packed with UV poly(bis-SorbPC)-coated particles (A, B), bare silica particles (C, D), and DOPC-coated particles (E, F). Capillaries were imaged with (A, C, E) or without (B, D, F) FM1-43.

FIG. 17G shows mean fluorescence intensity data for columns A-F. The fluorescent intensities illustrate that the poly(bis-SorbPC) bilayer coatings are retained on the particles after packing, whereas the DOPC bilayers are degraded, likely due to the shear forces associated with packing columns.

FIG. 19 shows long-term stability of lipid bilayer coatings on silica particles measured by flow cytometry using FM1-43 as a membrane stain. UV, $K_2S_2O_8/NaHSO_3$, and $(NH_4)2S_2O_8/NaHSO_3$ refer to the method used for polymerization of bis-SorbPC. Particles were exposed to surfactant (triton X-100) or organic solvent (ACN), washed, and stained with FM1-43 before flow cytometry. For all poly(bis-SorbPC)-coated particles the maintained fluorescence after exposure to chemical insults over a 30 day period illustrates that the polymerized bilayer coatings are temporally stable. Particles were stored dispersed in PBS at 4° C. between timepoints.

FIGS. 20A-20C show UV poly(bis-SorbPC)-coated silica particles (5 μm) that were slurry packed into an HPLC microbore guard column (2 cm×1 mm) at 560 psi. A gradient of 25-40% acetonitrile at 2900 psi (Shimadzu BCM-20A controller and LC-8A pumps) was applied to the column. The particles were removed from the column and incubated in the presence or absence of FM1-43 before fluorescence imaging, which utilized a microscope with a 20×/0.5 N.A. objective. Fluorescence images of bare silica particles treated with FM1-43 (A) and UV poly(bis-SorbPC)-coated particles without FM1-43 (B) showed no significant fluorescence. However, UV poly(bis-SorbPC)-coated particles treated with FM1-43 (C) were highly fluorescent, indicating that the polymerized bilayers were stable when exposed to high pressure and organic solvents. This data illustrates the physical and chemical stability of the poly(bis-SorbPC) bilayers following polymerization.

FIGS. 21A-21B show schematic depictions illustrating why particles aggregate after UV polymerization (A), but not after redox polymerization (B).

FIGS. 22A-22D show non-limiting examples of structures of dienoyl-containing polymerizable lipids such as mono-SorbPC (A), bis-SorbPC (B), mono-DenPC (C), and bis-DenPC (D).

FIG. 23 shows spectral changes that occur during polymerization of bis-SorbPC vesicles. The vesicle solutions were illuminated with a Xe arc lamp through a UG-1 band pass filter. FIG. 23A shows vesicles prepared in water with and without the 4-(dimethylamino) benzophenone (DMABN) photoinitiator. The absorbance was monitored at 258 nm.

The insert shows the polymerization of vesicles with DMABN prepared in water vs. MES buffer. The monomer conversion rate with the buffer is slower than in water. FIG. 23B shows bis-SorbPC with ROS membranes before and after the polymerization with DMABN. Rhodopsin activity, measured by the absorbance band at 500 nm, disappeared after the polymerization. FIG. 23C shows Rhodopsin reconstituted into bis-SorbPC with DMABN before and after the polymerization. The activity disappeared similar to the disappearance shown in FIG. 23B. FIGS. 23B and 23C were prepared in pH 5.5 MES buffer. All these polymerizations were done at 28° C.

FIG. 32 shows matrix assisted laser desorption ionization time-of-flight mass spectrometry (MALDI-TOF MS) spectra of.

FIG. 38 shows MALDI-TOF MS spectra of toxins incubated with poly(bis-SorbPC) PSLBs lacking gangliosides.

FIG. 39 shows MALDI-TOF MS spectra in the 500-3000 m/z range of FIG. 39A) HCCA matrix spotted on a poly (bis-SorbPC) PSLB containing 1% GM1 and 20% GD1a.

FIG. 40 shows MALDI-TOF MS spectra in the 5-20 kDa m/z range of FIG. 40A) SA matrix spotted on a poly(bis-SorbPC) PSLB containing 1% GM1 and 20% GD1a.

FIG. 44 shows MALDI-TOF MS spectra of poly(bis-SorbPC) PSLBs that were incubated with 1 μM PTB. The PSLBs contained (FIG. 44A) 10 mol % GD1a, (FIG. 44B) 20 mol % GD1a, and (FIG. 44C) 40 mol % GD1a. PTB was captured on poly(bis-SorbPC) PSLBs containing 10 mol %, 20 mol %, or 40 mol % GD1a from a 1 μM solution and subjected to MALDI-TOF MS analysis. Resulting spectra are shown in FIG. 44. At 10 mol % GD1a, the intensities of the PTB peaks were too weak for the subunits to be reproducibly resolved. At 20 mol % and 40 mol %, the peak intensities and resolution were adequate so 20 mol % was used in the experiments.

DESCRIPTION OF PREFERRED EMBODIMENTS

Figure 1:
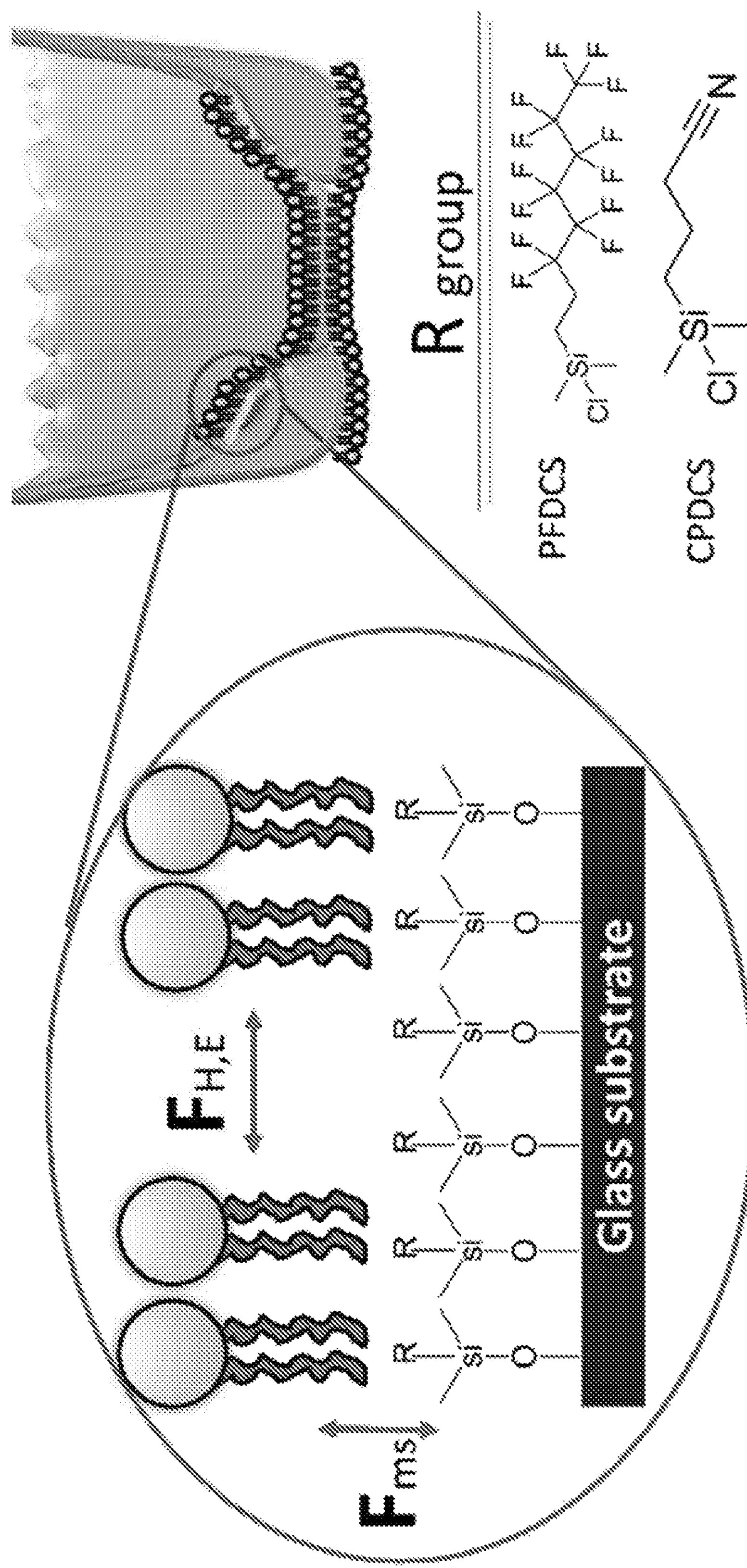
FIG. 1 shows a schematic of hybrid bilayer membrane formed by the adsorption of a lipid monolayer membrane on a silanized glass pipette aperture. The R group of the surface silane-modifier represents PFDCS or CPDCS used in the experiment. The modifiers define the surface energy of the underlying substrate which in turn affects the stability of the suspended lipid bilayer. Low energy surface modifiers such as PFDCS greatly improved the stability of BLMs due to the amphiphobic (oil/water repellency) character induced on the surface of the aperture thereby improving the force of interaction between the lipid membrane and the substrate ($F_{ms}$). The schematic also depicts the inherent weak force of interaction such as hydrophobic forces ($F_H$) and electrostatic forces ($F_E$) between the lipid molecules that limit the temporal stability of BLMs.

The following is a list of chemical abbreviations as used herein:

(tridecafluoro 1, 1, 2, 2-tetrahydrooctyl)dimethylchlorosilane (PFDCS);
(heptadecafluoro 1, 1, 2, 2-tetrahydrodecyl)dimethylchlorosilane (PFDDCS);
(tridecafluoro 1, 1, 2, 2-tetrahydrooctyl)trichlorosilane (PFTCS);
3-cyanopropyldimethylchlorosilane (CPDCS);
aminopropyldimethylethoxyosilane (APDES);
3,3,3-trifluoropropyl-dimethylchlorosilane (FPDCS);
ethyldimethylchlorosilane (EDCS);
n-octyl-dimethylchlorosilane (ODCS);
1,2-bis(octadeca-2,4-dienoyl)-sn-glycero-3-phosphocholine (bis-DenPC)
1,2-diphytanoyl-sn-glycero-3-phosphocholine (DPhPC);
4-(2-hydroxyethyl)-1-piperazineethanesulfonic acid (HEPES);
butylmethacrylate (BMA);
ethylene glycol dimethacrylate (EGDMA);
4-(dimethylamino) benzophenone (DMABN)
diethoxyacetophenone (DEAF);
Anhydrous acetonitrile (ACN);
α-hemolysin (α-HL);
Cholera toxin B (CTB);
Heat-labile enterotoxin B (LTB);
Pertussis toxin B oligomer (PTB)

As used herein, the term "buffer" is defined as a chemical species that can resist pH change upon the addition of an acidic or basic component in a solution by neutralizing small amounts of the added component, thus maintaining a relatively stable pH of the solution.

As used herein, the term "initiator" is defined as a chemical species that can start a reaction. For example, in a polymerization reaction, an initiator can generate radical species that can subsequently react with monomers to form intermediate compounds capable of linking successively with other monomers to form a polymeric compound.

As known to one of ordinary skill in the art, redox polymerization is defined as the use of an oxidizing and a reducing agent for oxidation-reduction reactions to produce radicals that can be used to initiate polymerization.

As used herein, the term "lipid", or alternatively, "lipid monomer", and any of their derivatives, i.e. phospholipid, is defined as an organic molecule that is amphiphilic, or having a polar end and a non-polar end. The general structure of a lipid monomer is a polar head group attached to two hydrocarbon chains, or tails, which are usually fatty acids. The structural and amphiphilic properties of the lipids cause them to spontaneously assemble into supramolecular structures in aqueous solutions, of which a lipid bilayer is one example. As used herein, the term "lipid bilayer" or "lipid bilayer membrane" is defined as two thin molecular sheets, each sheet comprising lipid monomers. As used herein, the term "lipid leaflet" is defined as one of the molecular sheets, or monolayer, of the lipid bilayer. As used herein, the term "vesicle" is defined as a spherical lipid bilayer.

As used herein, there term "membrane protein" is defined as a protein that is inserted into the membrane. In one embodiment, a "transmembrane protein" is a protein that is embedded in the lipid membrane and spans from one side of the membrane through to the other side of the membrane. Alternatively, another embodiment of a membrane protein is a protein that contains a hydrophobic portion that inserts into, but does not span, the membrane.

Section 1

Referring now to FIGS. 1-14, the present invention features a suspended lipid system comprising a supporting substrate having a substrate surface and an aperture and modified lipid membrane. The modified lipid membrane can comprise a plurality of lipid monomers and a plurality of polymerized, hydrophobic non-lipid monomers. The modified lipid membrane may be disposed on the substrate such that the lipid monomers form a lipid bilayer suspended across the aperture, and the non-lipid monomers may be disposed in the lipid bilayer. For instance, the non-lipid monomers may be adsorbed on the lipid bilayer, or disposed in the lipid monomer head and/or tail.

Another embodiment of the present invention features a suspended lipid system comprising a supporting substrate having a substrate surface and an aperture, and a modified lipid membrane. In one embodiment, an energy modifying layer is disposed on the substrate surface at or near the aperture to effect a lowering of a surface energy of the substrate surface. The modified lipid membrane may comprise a plurality of lipid monomers and a plurality of polymerized, hydrophobic non-lipid monomers comprising a methacrylate and a cross-linking agent. The modified lipid membrane may be disposed on the substrate such that the lipid monomers form a lipid bilayer suspended across the aperture and the energy modifying layer is disposed between the lipid monomers and the substrate surface. Preferably, the non-lipid monomers are disposed in or on the lipid bilayer and are polymerized at a near neutral pH by redox polymerization using a redox polymerization mixture comprising an initiator-buffer component and $NaHSO_3$.

The present invention may further feature a method of enhancing stability of a suspended lipid membrane. The method may comprise providing a supporting substrate having a substrate surface and an aperture, depositing non-polymerizable lipid monomers on the supporting substrate such that the lipid monomers form a lipid bilayer suspended across the aperture and the energy modifying layer is disposed between the lipid monomers and the substrate surface, inserting polymerizable, hydrophobic non-lipid monomers in the lipid bilayer to form a modified lipid membrane, and polymerizing the non-lipid monomers to stabilize the modified lipid membrane. In some embodiments, the method may further comprise depositing an energy modifying layer on the substrate surface at or near the aperture prior to the depositing non-polymerizable lipid monomers on the supporting substrate in order lower a surface energy of the substrate surface. In some embodiments, the non-lipid monomers are polymerized by UV irradiation, visible irradiation, gamma irradiation, redox polymerization, or thermal polymerization may be used to polymerize the non-lipid monomers. In other embodiments, the method may further comprise inserting photoinitiators, such as DEAP, prior to polymerizing the non-lipid monomers by UV or visible irradiation. In still other embodiments, a redox polymerizing mixture is used to polymerize the non-lipid monomers by redox polymerization.

Another embodiment of the present invention features a method of enhancing stability of a suspended lipid membrane comprising depositing an energy modifying layer on a substrate surface at or near an aperture of a supporting substrate such that the energy modifying layer lowers a surface energy of the substrate surface, depositing non-polymerizable lipid monomers on the supporting substrate such that the lipid monomers form a lipid bilayer suspended across the aperture and the energy modifying layer is disposed between the lipid monomers and the substrate surface, inserting polymerizable, hydrophobic non-lipid monomers comprising a methacrylate and a cross-linking agent in the lipid bilayer to form a modified lipid membrane, and polymerizing the non-lipid monomers using a redox polymerization mixture to stabilize the modified lipid membrane. Preferably, the redox polymerization mixtures comprise an initiator-buffer component and $NaHSO_3$ that allows for the redox polymerization to occur at a near neutral pH.

In some embodiments, the lipid bilayer can be suspended across the aperture such that a first lipid leaflet and a second lipid leaflet of the lipid bilayer are both disposed above or below the aperture. In other embodiments, the lipid bilayer can be suspended across the aperture such that a first lipid leaflet of the lipid bilayer is disposed above the aperture and a second lipid leaflet of the lipid bilayer is disposed below the aperture. In other embodiments, the non-lipid monomers are disposed in or on (i.e. deposited into or coated onto) a first lipid leaflet of the lipid bilayer, a second lipid leaflet of the lipid bilayer, or both. In some embodiments, the non-lipid monomers are disposed on the polar head groups of the lipids, the hydrocarbon tails of the lipids or both.

In some embodiments, the supporting substrate may be constructed from a material selected from a group consisting of a glass, a polymeric material, an epoxy, a metal oxide, or any other suitable material. Non-limiting examples of the supporting substrates include glass pipettes or solid sheets. The supporting substrate may be planar or curved.

One embodiment of the invention may feature a supporting substrate with an inherently low surface energy. For example, the surface of supporting substrate may have a surface energy of less than about 40 $mJ/m^2$ or less than about 60 $mJ/m^2$.

In other embodiments, an energy modifying layer may be disposed on the substrate surface at or near the aperture such that the energy modifying layer is disposed between the lipid monomers and the substrate surface. The energy modifying layer may be directly deposited on the substrate surface to form a coating. Preferably, the energy modifying layer can lower a surface energy of the substrate surface. In some embodiments, the energy modifying layer lowers the surface energy of the supporting substrate to less than about 40 $mJ/m^2$. In other embodiments, the energy modifying layer lowers the surface energy of the supporting substrate to less than about 60 $mJ/m^2$. In still further embodiments, the energy modifying layer lowers the surface energy of the supporting substrate to less than about 80 mJ/$m^2$.

In some embodiments, the energy layer modifying is a silane-modified layer. For example, the silane-modified layer may comprise an alkylated silane. Non-limiting examples of alkylated silanes includes (tridecafluoro 1, 1, 2, 2-tetrahydrooctyl)dimethylchlorosilane (PFDCS), (heptadecafluoro 1, 1, 2, 2-tetrahydrodecyl)dimethylchlorosilane (PFDDCS), (trideca-fluoro 1, 1, 2, 2-tetrahydrooctyl)trichlorosilane (PFTCS), 3-cyanopropyldimethyl-chlorosilane (CPDCS), aminopropyldimethylethoxyosilane (APDES), 3,3,3-trifluoro-propyldimethylchlorosilane (FPDCS), ethyldimethylchlorosilane (EDCS), or n-octyl-dimethylchlorosilane (ODCS). In some embodiments, the silane-modified layer comprises any chemically related substance capable of lowering the surface energy of the substrate.

In some embodiments, the lipid monomers can be polymerizable lipids or non-plymerizable lipids. For example, the lipid monomers may be polymerizable bis-SorbPC (1,2-bis [10-(2',4'-hexadieoyloxy)decanoyl]-sn-glycero-2-phosphocholine), non-polymerizable 1,2-diphytanoyl-sn-glycero-3-phosphocholine monomers, cell membrane fragments, naturally occurring lipids, or synthetic lipids.

In other embodiments, the plurality of polymerized, hydrophobic non-lipid monomers may comprise a methacrylate and a cross-linking agent. Exemplary methacrylates include aliphatic methacrylates and aromatic methacrylates. The aliphatic methacrylate may be alkyl substituted. For example, the alkyl substitution can be $C_4$-$C_{10}$. The aromatic methacrylate may be a benzyl methacrylate, a napthyl methacrylate, or any other aromatic methacrylate. In some embodiments, the cross-linking agent is a dimethacrylate, such as ethylene glycol dimethacrylate and derivatives thereof.

In some embodiments, the non-lipid monomers can be polymerized by UV irradiation, visible irradiation, gamma irradiation, redox polymerization, or thermal polymerization. When the non-lipid monomers are polymerized by UV or visible irradiation, the modified lipid membrane may further comprise photoinitiators. Preferably, the photoinitiators are lipophaic, such as DEAP. In some embodiments, the duration of UV irradiation or visible irradiation is sufficient to photopolymerize the non-lipid monomers. In preferred embodiments, the duration of irradiation is between about 5 to 10 minutes. In some embodiments, the duration of UV irradiation is between about 1 to 5 minutes. In other embodiments, the duration of UV irradiation is between about 5 to 15 minutes.

In some embodiments, the modified lipid membrane has an enhanced electrical stability. For example, a breakdown voltage of the modified lipid membrane is at least 1,000 mV. In other embodiments, a breakdown voltage of the modified lipid membrane is at least 1,250 mV. In still other embodiments, a breakdown voltage of the modified lipid membrane is at least 1,500 mV or at least 1,750 mV.

In other embodiments, the modified lipid membrane has an enhanced mechanical stability. For instance, the membrane is sufficiently flexible to support functional ion channels. In still other embodiments, the modified lipid membrane has an enhanced temporal stability. For example, the modified lipid membrane has a temporal stability of at least 8 hours, at least 10 hours, at least 15 hours, at least 24 hours, at least 36 hours, or at least 48 hours.

In some embodiments, the non-lipid monomers are polymerized by redox polymerization. A redox polymerization mixture comprising an initiator-buffer component and $NaHSO_3$ may be used for redox polymerization. In some embodiments, the redox polymerization mixture comprises any redox mixture that polymerizes the non-lipid monomers, i.e. a mixture having a reductant and an oxidant. In preferred embodiments, the initiator-buffer component comprises ammonium persulfate. Suitable mole ratios of ammonium persulfate, $NaHSO_3$, and lipids can include about 10-500 AP: 10-500 $NaHSO_3$:1 lipid, about 50-400 AP:50-400 $NaHSO_3$: 1 lipid, or about 100-300 AP:100-300 $NaHSO_3$: 1 lipid.

Preferably, the redox polymerization mixtures allows for the reaction to occur at a near neutral pH and to maintain a constant pH. In some embodiments, the redox polymerization occurs at a pH between about 5 to 9. In other embodiments, the redox polymerization occurs at a pH between about 5.5 to 7.5. In still other embodiments, the redox polymerization occurs at a pH between about 6 to 7.

A kit for a preparing a suspended lipid membrane having enhanced stability is provided in the present invention. The kit may comprise a supporting substrate having a substrate surface and an aperture, a plurality of non-polymerizable lipid monomers, a plurality of polymerizable, hydrophobic non-lipid monomers comprising a methacrylate and a cross-linking agent, and a redox polymerization mixture comprising an initiator-buffer component and $NaHSO_3$. To use the kit to prepare the suspended lipid membrane, the non-polymerizable lipid monomers are deposited on the supporting substrate such that the lipid monomers form a lipid bilayer suspended across the aperture, and the polymerizable, hydrophobic non-lipid monomers are disposed in the lipid bilayer. Preferably, the non-lipid monomers are polymerized by redox polymerization at a near neutral pH using the redox polymerization mixture to form a modified lipid membrane.

In some embodiments, the supporting substrate has an inherently low surface energy. In other embodiments the kit may further comprising an energy modifying compound that can be deposited on the substrate surface at or near the aperture to form an energy modifying layer. The energy modifying layer is disposed between the lipid monomers and the substrate surface in order to lowers a surface energy of the substrate surface and to increase stability of the modified lipid membrane. The energy modifying compound may comprise a silane, such as an alkylated silane. Exemplary alkylated silannes include (tridecafluoro 1, 1, 2, 2-tetrahydrooctyl)dimethylchlorosilane (PFDCS), (heptadecafluoro 1, 1, 2, 2-tetrahydrodecyl)dimethylchlorosilane (PFDDCS) (tridecafluoro 1, 1, 2, 2-tetrahydrooctyl)trichlorosilane (PFTCS), ethyldimethylchlorosilane (EDCS), aminopropyldimethylethoxyosilane (APDES), 3,3,3-trifluoropropyl-dimethylchlorosilane (FPDCS), ethyldimethylchlorosilane (EDCS), or n-octyl-dimethylchlorosilane (ODCS).

EXPERIMENTAL

Reagents and Materials

Gramicidin A, ethylene glycol dimethacrylate (EGDMA), KCl, 4-(2-hydroxyethyl)-1-piperazineethanesulfonic acid (HEPES) and α-hemolysin (α-HL) were purchased from Sigma-Aldrich (St. Louis, Mo.). Gramicidin A was diluted to 10 μg/mL in ethanol. Tridecafluoro 1, 1, 2, 2-tetrahydrodimethylchlorosilane (PFDCS) was purchased from Gelest, Inc. (Morrisville, Pa.). 3-cyanopropyldimethylchlorosilane (CPDCS) was purchased from TCI America, Inc. (Portland, Oreg.). Anhydrous acetonitrile (ACN) and NaCl were purchased from EMD Chemical Inc. (Gibbstown, N.J.). Ethanol was purchased from Decon Laboratories (King of Prussia, Pa.). Butyl methacrylate (BMA) was purchased from Alfa Aesar (Ward Hill, Mass.) and diethoxyacetophenone (DEAP) was purchased from Acros Organics (Pittsburgh, Pa.). 1, 2-diphytanoyl-sn-glycero-3-phosphocholine (DPhPC) lipid in chloroform was purchased from Avanti Polar Lipids, Inc. (Alabaster, Ala.). Nanopure water was obtained from a Barnstead EasyPure UV/UF purifier with resistivity of 18.3 MΩ cm.

Pipette Aperture Fabrication and Surface Modification

Borosilicate capillaries (1.5 outer diameter and 1.1 mm inner diameter) were purchased from World Precision Instruments, (Sarasota, Fla.) and were fabricated into pipette apertures with 25-30 μm diameter using a P-97 micropipette puller (Sutter Instruments, Novato, Calif.) and fire polished with a model MF-900 microforge (Narishige, East Meadow, N.Y.) for BLM formation. A schematic of the pipette fabrication process is shown in FIG. 7. Glass pipette apertures were silane functionalized using a solution phase method reported previously. Briefly, glass pipettes were filled and submerged in 0.1 M $HNO_3$ for 30 min followed by rinsing with $H_2O$ at least 3 times. The pipettes were rinsed with acetone and dried on a hot plate at 80-100° C. for 5 min or in an oven at 70° C. for 15-30 min. The pipettes were filled with and then submerged in 2% v/v silane solution in either ACN (for CPDCS) or toluene (for PFDCS) for 6-12 h. Pipettes functionalized with CPDCS were rinsed with ACN while PFDCS-modified pipettes were rinsed with toluene. Finally, the resulting CPDCS- or PFDCS-functionalized pipettes were rinsed with ethanol and $H_2O$. Only those silane-modified glass pipette apertures that showed a high success rate (>80%) in the formation of BLMs, as monitored by repetitive formation and voltage-induced breakdown, were selected for use in further experiments.

Formation and Characterization of BLMs

DPhPC dissolved in n-decane to a final concentration of 20 mg/mL was used to form BLMs by the painting method. Briefly, stock lipids suspended in chloroform were dried using compressed Ar followed by overnight vacuum. Conventional (unpolymerized) BLMs were prepared with this solution. Methacrylate-doped BLMs (MA-BLMs) describe BLMs prepared using a mixture of lipids, methacrylate monomers and photoinitiators in the absence of UV photopolymerization. PSS-BLMs describe MA-BLMs that were subsequently photopolymerized. For MA-BLMs and PSS-BLMs, DPhPC solutions were prepared with BMA, EGDMA and DEAP as follows. Initially, radical inhibitors were removed from BMA and EGDMA using an alumina column ($Al_2O_3$, 50-200 μm, 60 Å, Acros). The monomers were then combined in 1:1:1 ratios with DEAP to yield a solution referred to as a monomer mixture, followed by addition of one equivalent of lyophilized DPhPC to yield and overall mixture of 1:1:1:1 composition of BMA:EGDMA:DEAP:DPhPC. The lipid/monomer mixture was vortexed for 30 s prior to the addition of n-decane.

BLMs were formed by addition of 2 μL of lipid or lipid/monomer mixture solution dissolved in n-decane to the pipette tip and dried with $N_2$ gas. Pipettes were back filled with recording buffer (1 M KCl, 5 mM HEPES, pH 7.4) and mounted on the head stage of a patch clamp amplifier (EPC-10, HEKA Electronics, Bellmore, N.Y.). The bath chamber was filled with recording buffer and connected to the reference electrode via a salt bridge. The lipid or methacrylate-doped lipid solution was painted by gently sweeping a plastic micropipette tip across the silanized pipette aperture submerged in the recording buffer.

Formation of BLMs or MA-BLMs across silanized pipette apertures was monitored by the spontaneous increase in electrical resistance from open pipette resistance (50-100 KΩ) to >2 GΩ. Further, the formation of BLM or MA-BLMs was verified by applying an increasing potential from 0 to 2000 mV in 10 mV increments of 50 ms duration. Additionally, the appearance of transient pores in BLMs under applied electrical fields was used to indicate the existence of BLMs prior to UV irradiation, although care was taken not to allow complete rupture of the BLM upon observation of transient pores. Subsequently, MA-BLMs were polymerized, forming PSS-BLMs, by UV irradiation using a pen lamp (UVP, Upland, Calif., Model 90-0012-01) at a distance of 3-5 cm from the BLM.

The biophysical properties of conventional, MA- and PSS-BLMs were characterized by the reconstitution and measurement of gramicidin A or α-HL activity. A 0.5 μL aliquot of stock gramicidin peptide (10 μg/mL) in ethanol was added to 500 μL bath solution to a final concentration of 10 ng/mL and allowed to incubate with the BLMs. The activity of gramicidin was monitored with a potential of 70 mV applied across the BLMs. Quantized changes in current were typically observed within 2 min of adding gramicidin to the bath solution. Two μl of α-HL (0.5 mg/mL in recording buffer) was added to bath solution containing 500 μl of recording buffer and the insertion of IC measured a bias potential of +40 mV across the BLM.

Conductance Measurement

The conductance of conventional BLMs, MA-BLMs and PSS-BLMs was measured by applying a square wave of increasing potential from −100 to +100 mV in 10 mV increments of 50 ms duration. The potential was held for 10 ms at 0 mV before and after applying each pulse. The average of the steady state current between 30 to 50 ms (following capacitive decay) was plotted versus the applied potential. The conductance is reported as the slope of the current versus potential plot and normalized for pipette aperture area, as a first approximation of BLM area. A minimum of three pipettes each was used for evaluating BLMs suspended across CPDCS or PFDCS-modified pipette apertures. For each pipette, a minimum of three BLMs was analyzed to determine the mean conductance.

Assessment of BLM Stability

The stability of conventional, MA and PSS-BLMs was quantified by measuring breakdown voltage ($V_B$), longevity and air-water transfer count (AWT). $V_B$ is the potential at which the BLM undergoes irreversible rupture, and is measured by applying an increasing potential from 0 to 2000 mV in 10 mV increments of 50 ms duration and observing the potential at which a large, non-linear increase in current occurs. The mean $V_B$ indicates the electrical stability of BLMs. AWT refers to the number of times a BLM survives transport across the air-water interface before it ruptures. To assess AWT, the aperture was removed from aqueous buffer and maintained in air for 1 s, prior to re-submersion in buffer. Each cycle of removal and return to buffer is indicated as one AWT. Longevity was measured as the average time required for the bilayer to undergo rupture under the application of a ±5 mV 20 Hz square-wave.

Statistical Analysis

All data is presented as mean±standard deviation. For each measurement, a minimum of three BLM replicates on at least three different pipettes were collected. For each BLM stability metric analyzed, outlying data was assessed using the Q test at the 90% confidence level. All statistical comparisons were performed using Student's t-test at the 95% confidence interval.

Single-channel recordings with corresponding all-points histograms and mean open times were analyzed using TAC (X4.3.3) and TACfit X4.3.3 (Bruxton). The fit duration histogram for open probability and construction uses the Sigworth and Sine transformations.

Redox Polymerization of Bis-DenPC

The following is a non-limiting example of redox polymerization of bis-DenPC (10 mg/mL)

Bis-DenPC stored in benzene was dried over argon gas and lyophilized overnight. The resultant solid was suspended in n-decane to a final concentration of 10 mg/mL. About 0.5 μL of this solution was then painted across a glass pipette aperture (ca. 30 μm diameter) that had been silanized with a perfluorinated silane, forming a black lipid membrane (BLM).

A redox initiation solution containing $NaHSO_3$ and $(NH_4)_2S_2O_8$ was prepared in buffer solution containing 1M KCL and 5 mM HEPES (pH 7.4). Redox initiation solutions were prepared separately and mixed before perfusing into the bath solution into which the BLM was immersed. BLM polymerization was performed using a mole ratio of lipid (bis-DenPC):$NaHSO_3$:$(NH_4)_2 5_2 O_8$=1:300:300)

Redox Polymerization of DPhPC BLMs Doped with Methacrylate Monomers

The following is a non-limiting example of redox polymerization of DPhPC BLMs doped with methacrylate monomers.

DPhPC dissolved in chloroform was dried over argon gas and lyophilized overnight followed by suspension in n-decane to a final concentration of 20 mg/mL.

Doping Polymerizable Monomers into BLMs

Figure 13:
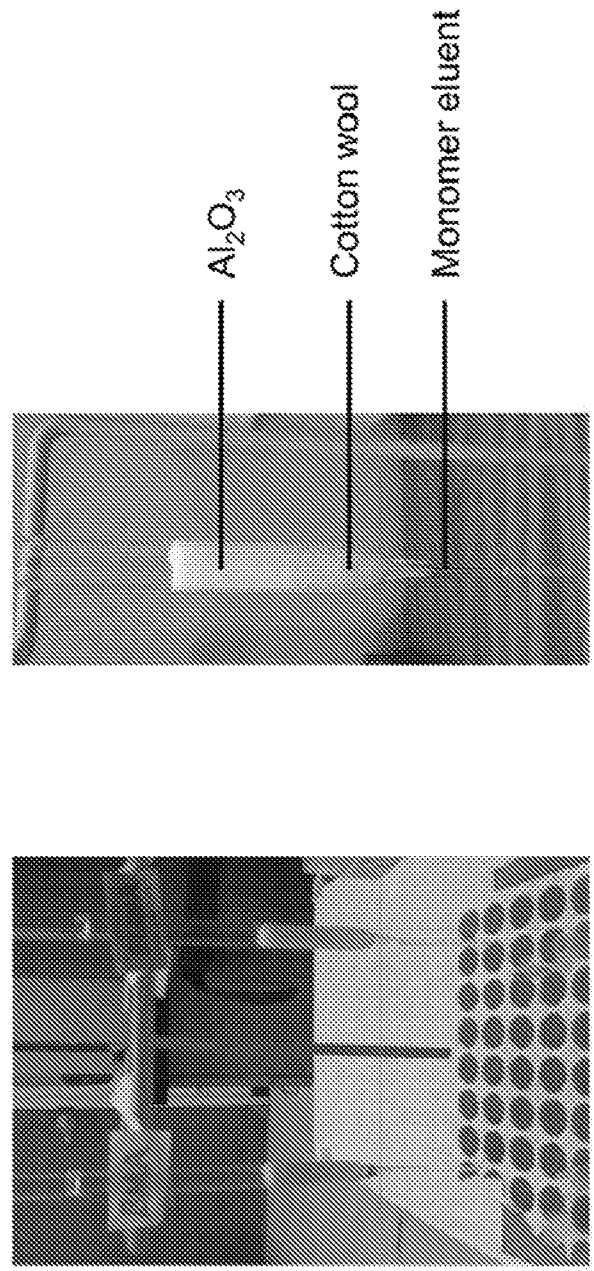
FIG. 13 shows an exemplary lab arrangement for removal of inhibitor species to make active BMA and EDGMA monomers using aluminum oxide.

Butyl methacrylate (BMA), ethylene glycol dimethacrylate (EGDMA) and the initiator diethoxy acetophenone (DEAP) in a 1:1:1 ratio were doped into the DPhPC BLM. All experiments were performed under yellow light (low pressure sodium lamp). As shown in FIG. 13, prior to use, the monomers were made reactive by removing the polymerization inhibitor using aluminium oxide ($Al_2O_3$, 50-200 μm, 60 A). For a 1:1 mole ratio of DPhPC:monomers, the monomers (BMA, EGDMA, and DEAP) were first added to the dried lipid and vortexed for ca. 30 s. The mixture of lipid and monomers were then suspended in n-decane to a final concentration of 20 mg/mL and finally vortexed for ca. 1 min before use. The vial containing the mixture was wrapped in aluminum foil to prevent exposure to light.

Table 1 provides exemplary mole and volume amounts of DPhPC lipid and monomers used for preparation of BLMs containing poly(methacrylate) networks.

| | BMA | EGDMA | DEEP | DPhPC |
|---|---|---|---|---|
| Mole (μmol) | 1.2 | 1.2 | 1.2 | 1.2 |
| Volume (μL) | 0.2 | 0.23 | 0.24 | 40 |
| Mole fraction % | 25 | 25 | 25 | 25 |

Redox Polymerization of Methacrylate Doped BLMs

Using newly fabricated and silanized glass pipettes, methacrylate doped BLMs were formed via a tip-dip or a painting method. The fabricated pipette was filled with buffer solution (1 M KCl and 5 mM HEPES, pH 7.4) and mounted onto the head stage of a patch clamp amplifier.

After formation of methacrylate doped BLMs, redox reagents containing equal moles of $NaHSO_3$:$(NH4)_2S_2O_8$ were prepared separately. An exemplary mole ratio of lipid (DPhPC):$NaHSO_3$:$(NH_4)_2S_2O_8$ is 1:300:300. To perform redox polymerization, 500 μL each of $NaHSO_3$ and $(NH_4)_2S_2O_8$ were mixed together to give a total volume of 1000 μL, which was sufficient to displace the recording buffer in the bath reaction chamber. The methacrylate doped BLM was allowed to react for 5 to 10 min. After reaction, the bath solution was exchanged 5× with 1M KCl and 5 mM HEPES, pH 7.4 buffer.

Table 2 shows a non-limiting example of concentrations of lipid and redox reagents that may be used.

| | DPhPC | $NaHSO_3$ | $(NH_4)_2S_2O_8$ |
|---|---|---|---|
| Mole (mol) in 0.5 μL of methacrylate/lipid mixture | $6 \times 10^{-9}$ | $1.8 \times 10^{-6}$ | $1.8 \times 10^{-6}$ |
| Concentration (mg/mL) | 20 | 0.36 | 0.82 |
| Volume used (μL) | 0.5 | 500 | 500 |

Table 3 shows an exemplary comparison of breakdown voltages for a DPhPC control and a redox polymerized monomer mixture.

| Sample | | Breakdown mV |
|---|---|---|
| DPhPC Control | | 984 ± 210 |
| Monomer Mixture | 0 min | 394 ± 73, n = 11 |
| (Redox) | 15 min | >2000, n = 2 |

Insertion of Ion Channel

Figure 14:
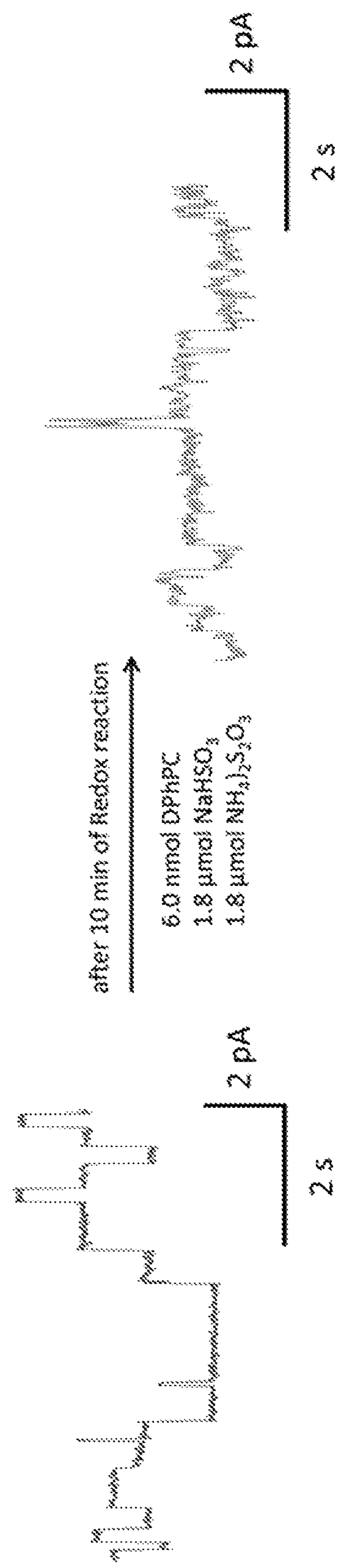
FIG. 14 shows the single channel activity of gramicidin A in methacrylate-doped BLMs before and after redox polymerization using a redox initiation solution containing $NaHSO_3$ and $(NH_4)_2S_2O_8$. The conductance and activity of ion channel drastically decreased after 10 min of redox reaction.

About 0.5 μL of Gramicidin A (0.5 mg/mL) was added close to the tip of pipette containing methacrylate doped BLMs to allow for insertion. Insertion was observed after a few minutes from the addition of gramicidin. Single channel activities with multiple states were observed after application of a holding potential of 70 mV. Next, the bath solution was exchange with redox buffer and allowed to react for 10 min, after which the conductance drastically decreased due to extended cross-linking in the methacrylate monomers, as shown in FIG. 14.

Results and Discussion

The lifetime, electrical and physical properties of monomer doped BLMs were investigated to probe the effect of various degrees of cross-linking in BLMs on the properties of IC proteins. FIG. 1 shows a schematic of a BLM suspended across a microaperture functionalized with either CPDCS or PFDCS. Glass pipette aperture surfaces were first functionalized with either CPDCS or PFDCS to lower the surface energy, which is necessary to yield the tails-down lipid configuration required to form BLMs. Thus, the resulting membrane orientation across the modified glass pipette aperture is analogous to the folding of two lipid monolayers from opposite sides across Teflon apertures.

Decreased substrate surface energy enhances BLM stability by improving the force of interaction between the lipid membrane and the substrate ($F_{ms}$)—However, the weak van der Waals forces ($F_V$) and electrostatic forces ($F_E$) of interactions between adjacent lipid molecules limit the temporal, electrical, and mechanical stability of BLMs. For example, when BLMs are suspended across silane-functionalized glass apertures with decreased surface energy, the inherently weak forces of interaction between the lipid molecules in the self-assembled bilayer (FIG. 1, $F_{V,E}$) limit the average longevity of the BLMs formed on CPDCS- and PFDCS-modified apertures to 2±1 h and 8±1 h, respectively (Tables 4 and 5). To overcome these limitations, the fabrication of a polymer scaffold within BLMs suspended across silane functionalized glass apertures to provide additional stabilizing interactions was investigated. In the present invention, BLMs were prepared on two silane-modified surfaces chosen based on the prevalence of CPDCS modifications in the BLM literature and the recently demonstrated significantly enhanced BLM lifetimes provided by PFDCS.

Table 4 shows physical and electrical properties of conventional BLMs, MA-BLMs, and PSS-BLMs on CPDCS-modified pipette apertures.

| BLM composition | UV (min) | $V_B$ (mV) | Normalized Conductance ($\times 10^{-2}$ pS $\mu m^{-2}$) | AWT | Longevity (h) |
|---|---|---|---|---|---|
| Conventional | 0 | 460 ± 21 | 5.5 ± 1.7 | 4 ± 3 | 2 ± 1 |
| BLMs | 15 | 575 ± 124 | 6.0 ± 3.0 | 6 ± 4 | 2 ± 1 |
| MA-BLMs | 0 | 493 ± 59 | 8.7 ± 0.5 | 14 ± 13 | 2 ± 2 |
| PSS-BLMs | 5 | 615 ± 107 | 10.7 ± 1.9 | >50 | 23 ± 9 |
| | 10 | >2000 | 9.1 ± 0.8 | >50 | 28 ± 16 |

Table 5 shows physical and electrical properties of conventional BLMs, MA-BLMs, and PSS-BLMs on PFDCS-modified pipette apertures.

| BLM composition | UV (min) | $V_B$ (mV) | Normalized conductance ($\times 10^{-2}$ pS $\mu m^{-2}$) | AWT | Longevity (h) |
|---|---|---|---|---|---|
| Conventional | 0 | 984 ± 210 | 9.00 ± 2.00 | >50 | 8 ± 1 |
| BLMs | 15 | 980 ± 254 | 8.49 ± 0.91 | >50 | 8 ± 1 |
| MA-BLMs | 0 | 520 ± 119 | 4.95 ± 0.57 | 32 ± 11 | 6 ± 1 |
| PSS-BLMs | 5 | 1033 ± 182 | 4.81 ± 0.14 | 36 ± 13 | 26 ± 13 |
| | 10 | >2000 | 6.93 ± 1.08 | >50 | 40 ± 14 |

Figure 2A:
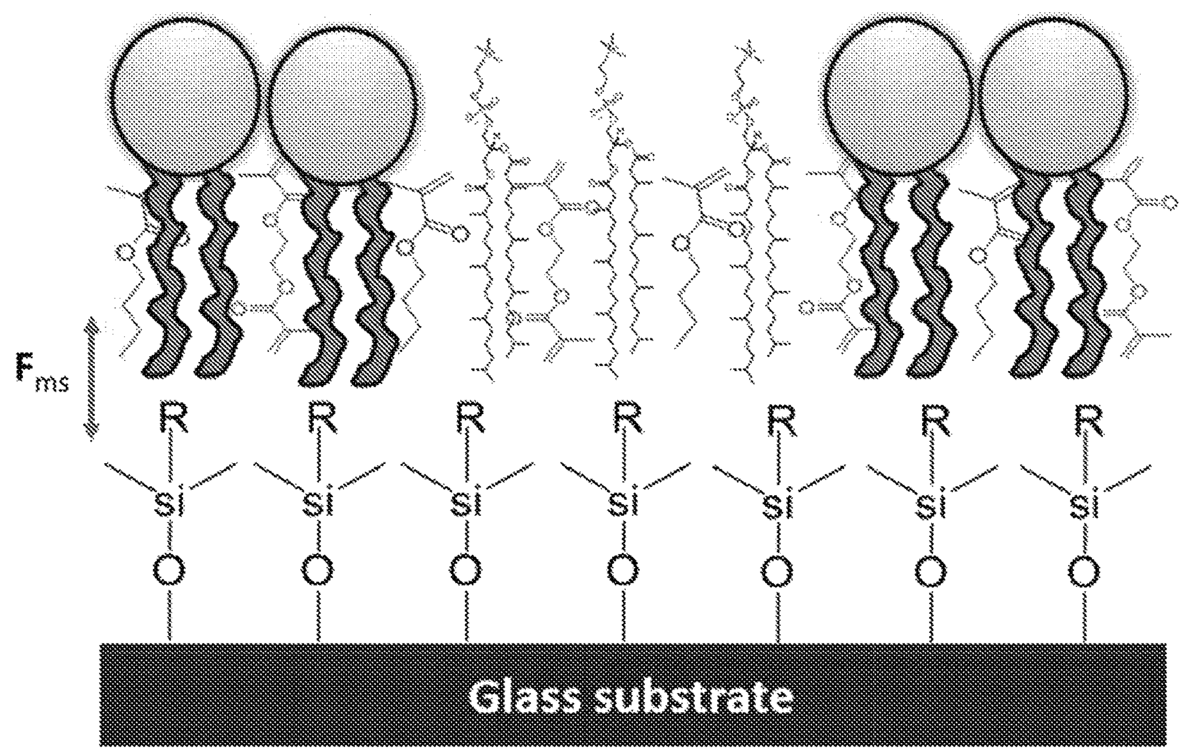
FIG. 2A shows a schematic of small hydrophobic monomers introduced into the lamella region of the lipid membrane.
Figure 2B:
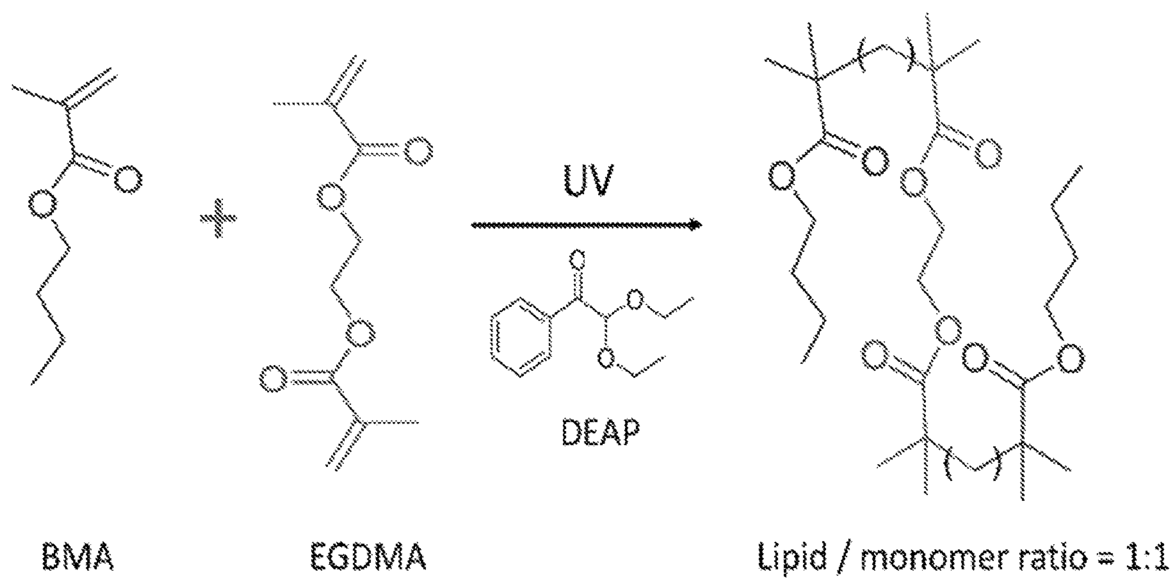
FIG. 2B shows a chemical cross-linking of monomers that occurs when the initiator (DEAP) is activated upon UV-irradiation. The cross-linking creates a polymer network in the membrane that is much stronger than the inherently weak hydrophobic force of interaction between lipid molecules.

To further improve the stability of BLMs for applications requiring high mechanical and temporal stability, the integration of a polymer network into the lamella region of the BLM was evaluated. A methacrylate polymer scaffold prepared from BMA and EGDMA was utilized. The BMA forms linear polymer chains that are cross-linked by the EGDMA to improve the polymer stability. Without wishing to limit the present invention to a particular theory or mechanism, while the resulting polymer does not covalently link the DPhPC monomers that form the BLM, it is hypothesized that the enhanced structural stability provided by the polymer network would enhance BLM lifetime and mechanical stability. The resulting BLM architecture is referred to herein as a polymer scaffold-stabilized BLM (PSS-BLM). FIG. 2 shows an exemplary schematic of the proposed monomer arrangement in the lamellar region of monomer doped BLMs, which is analogous to the packing of methacrylate monomers in the bilayer of lipid vesicles. The extent of stabilization achieved by PSS-BLMs was determined by measuring the electrical and physical properties of conventional BLMs and MA-BLMs before and after UV irradiation.

Physical and Electrical Properties of PSS-BLMs

To evaluate the physical and electrical properties of PSS-BLMs, the air-water transfer (AWT), $V_B$, and longevity were measured as metrics of the physical, electrical, and temporal stability, respectively. A higher value of AWT and $V_B$ indicates enhanced mechanical and electrical stability of the specific BLM composition.

The successful formation of a BLM was indicated when $V_B$ was observed in the range of 0-1000 mV, prior to polymerization, as opposed to a high resistance blockage in the pipet which cannot be broken down in this range. The mean $V_B$ observed for conventional BLMs suspended across CPDCS-modified pipette apertures was 460±21 mV. Furthermore, electrical, physical, and temporal stability were statistically similar before and after 15 min of UV irradiation of conventional BLMs, indicating no deleterious effects of UV exposure. When the monomer mixture was incorporated into the BLM in the absence of UV-irradiation to form MA-BLMs (Table 4), similar longevity and $V_B$ were observed compared to conventional BLMs. Though inclusion of the monomer mixture increases membrane conductance, the magnitude of the change is within the normal working range of BLMs on a range of aperture substrate materials. Upon cross-linking of MA-BLMs via UV irradiation for 5 min to yield PSS-BLMs, a >10 fold increase in AWT and longevity and a 30% increase in $V_B$ were observed compared to conventional BLMs. Additional improvements in electrical stability were observed upon increasing UV irradiation time to 10 min. Importantly, the membrane conductance, a key measure of membrane integrity, was statistically similar in MA-BLMs and PSS-BLMs irrespective of UV irradiation time.

Stability metrics for conventional BLMs on PFDCS-modified apertures were statistically similar before and after 15 min of UV irradiation (Table 5). Conventional BLMs formed on PFDCS-modified apertures exhibit marked stability increases compared to those formed on CPDCS apertures due to enhanced surface/lipid interactions. Unlike on CPDCS-modified apertures, MA-BLMs formed on PFDCS-modified apertures exhibited decreased electrical and mechanical stability as indicated by $V_B$ and AWT (47% and 30% decreases, respectively) compared to conventional BLMs, though the magnitudes of these values are still comparable to BLMs formed on CPDCS-modified apertures. Thus, it is likely that the inclusion of the monomer mixture disrupts the lipid-surface interactions and yields BLM stabilities comparable to those formed on surfaces with weaker surface-lipid interactions.

Upon formation of PSS-BLMs via 5 min of UV irradiation, $V_B$ recovered to values equivalent to conventional BLMs; however, >3 fold increase in longevity was observed compared to conventional BLMs. Furthermore, a 45% reduction in membrane conductance was observed for MA-BLMs, and persisted in PSS-BLMs formed via 5 minutes of UV irradiation. When UV irradiated for 10 minutes, an increase in membrane conductance was observed, though the values were still lower than conventional BLMs prepared with this surface modification. Furthermore, $V_B$ and longevity were increased by >2- and 5-fold, respectively, compared to conventional BLMs.

Based on the aggregate of the measurements, it appears that formation of the polymer scaffold exhibits no deleterious effects on membrane stability or membrane integrity within the BLM. In fact, PSS-BLMs formed via 5 min or 10 min of UV irradiation of MA-BLMs on CPDCS- and PFDCS-modified apertures surprisingly yielded significantly improved membrane longevity and reduced membrane conductance with enhanced $V_B$ and little or no adverse effect on AWT. For membranes formed on both CPDCS and PFDCS-modified apertures, membrane conductance was unchanged when comparing MA-BLMs and PSS-BLMs formed via 5 minutes of UV irradiation. Though the conductance was increased with further irradiation time, the conductance was still lower than that obtained from a conventional BLM.

Electrical Properties of Monomer Doped BLMs

To evaluate the physical and electrical properties of monomer doped BLMs and the extent of cross-linking of monomers introduced into BLMs, the AWTs, $V_B$ and longevity were measured as a metric of the mechanical, electrical and temporal stability respectively.

Figure 3B:
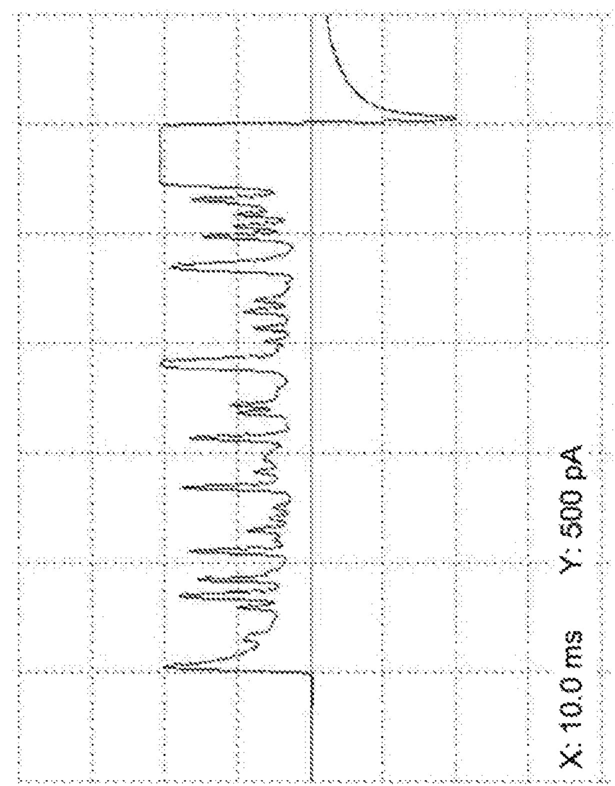
FIG. 3B shows a capacitance current trace vs. time for monomer doped BLMs suspended across PFDCS modified pipette aperture with ca. 30 μm diameter. When BLMs were doped with monomers, the transient pores increased during the application of increasing induced electric field.
Figure 3A:
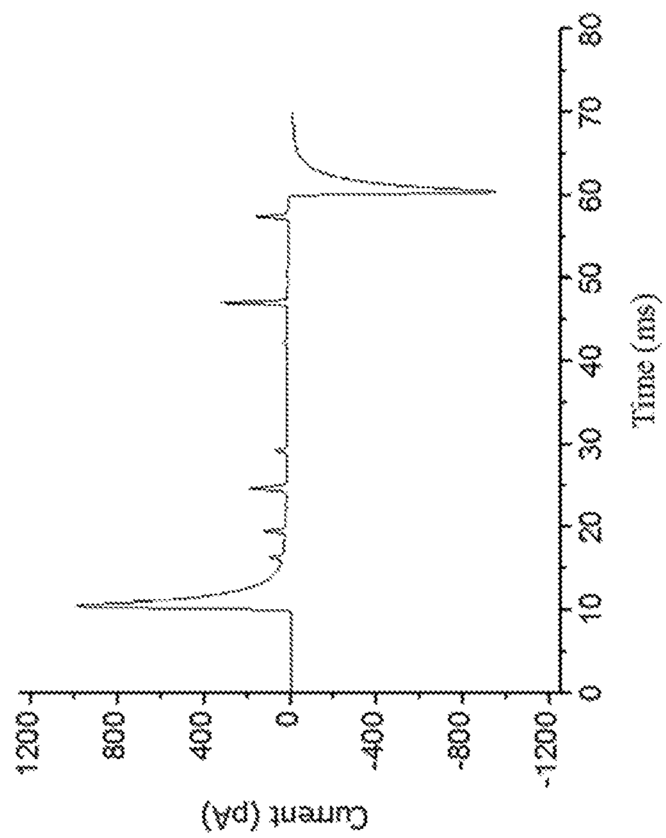
FIG. 3A shows a capacitance current trace vs. time for DPhPC BLMs suspended across a PFDCS modified pipette aperture with ca. 30 μm diameter. The transient hydrophobic pores were observed between 500-700 mV before the rupture of BLMs at >1000 mV.
Figure 6:
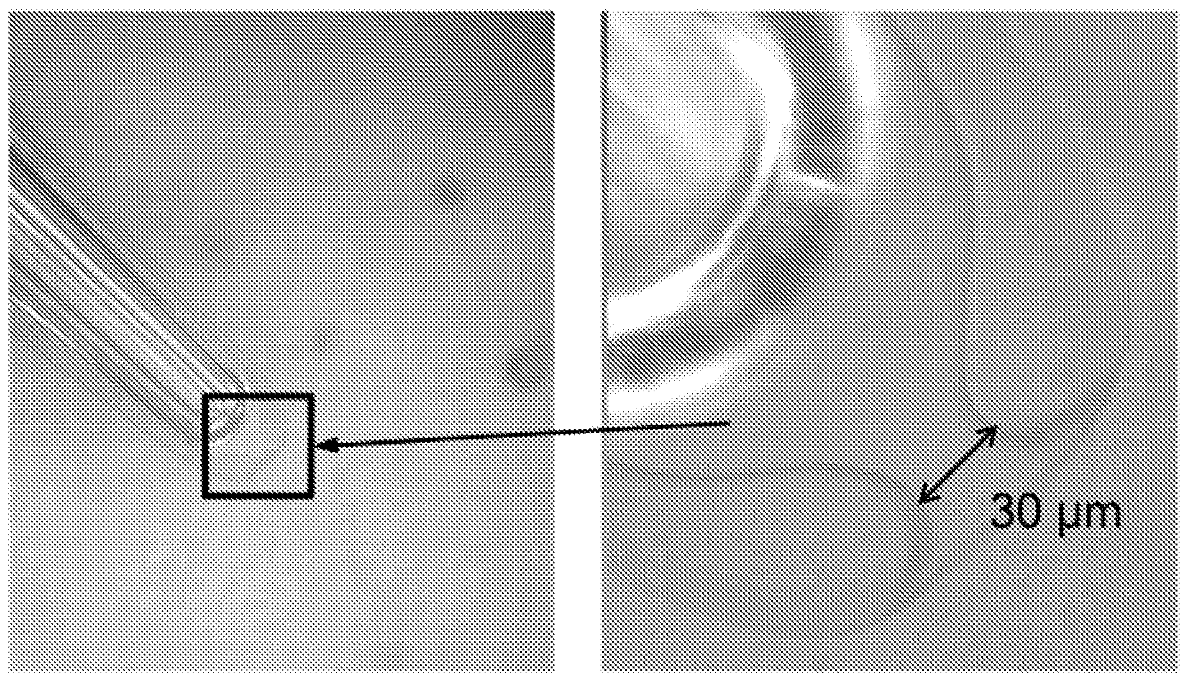
FIG. 6 shows an expanded view of a glass pipette aperture. A non-limiting example of a glass pipette aperture diameter is 30 μm.
Figure 7A:
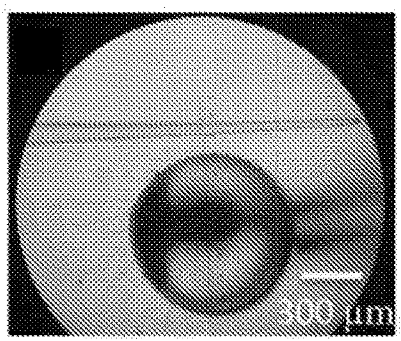
FIGS. 7A-7F show an exemplary fabrication process of pipette microapertures for suspended BLM formation.
Figure 7B:
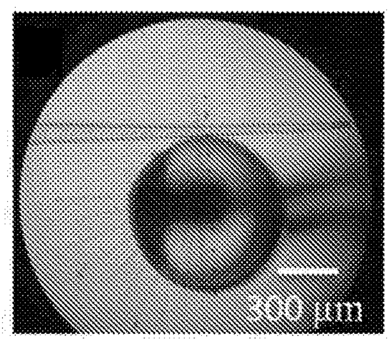
Figure 7C:
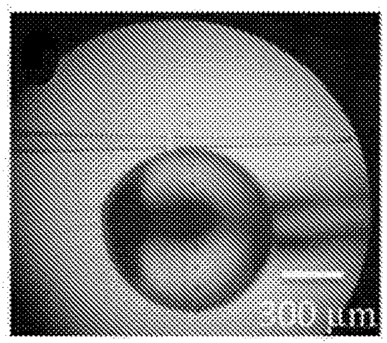
Figure 7D:
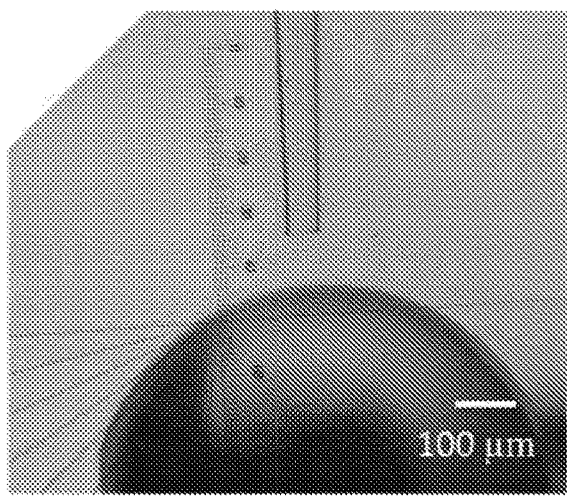
Figure 7E:
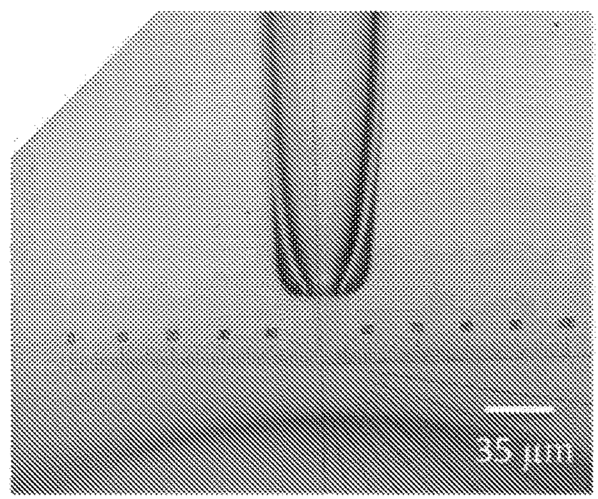
Figure 7F:
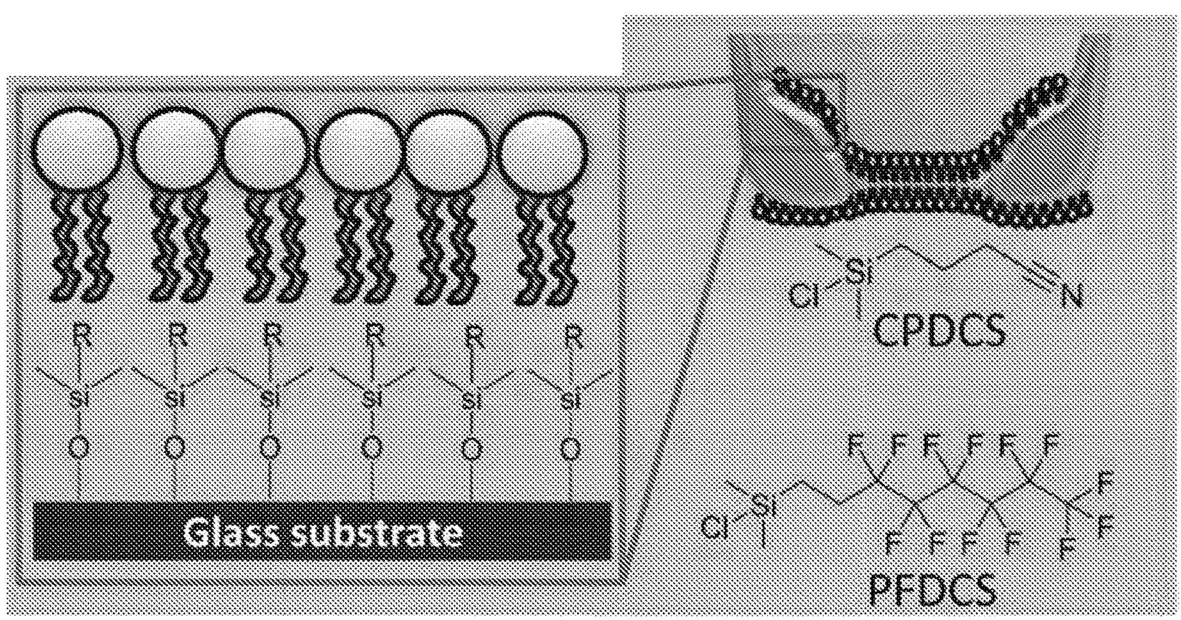

FIGS. 3A and 3B shows a capacitance current trace vs. time for BLMs and monomer doped BLMs suspended on a PFDCS modified microaperture. The presence of a suspended lipid bilayer was always verified by inducing the rupture of the membrane by increasing the potential from 0-2000 mV in 10 mV increments for a duration of 50 ms. Membranes that do not rupture at potential <2000 mV were often classified as blockages. Pipettes that do not give a high success rate in BLM formation were often discarded.

In addition to using pipettes that gave >90% success rate in the formation of BLMs, the presence of BLMs prior to UV irradiation was confirmed by the appearance of the first transient pores under induced electric field. Further, the transient pores were used to indicate an existing BLM with thickness similar to cell membranes. Subsequently, increasing pore size or number preceded the rupture of BLMs, thus the complete rupture of a BLM was prevented by quickly removing the applied electric field before irradiation of monomer doped BLMs. The transient pores were observed to occur between 500-700 mV for BLMs and 400-500 mV for monomer doped BLMs suspended across perfluorinated apertures. Numerous transient pores were often observed in monomer doped BLMs under applied electric field as compared to BLMs without monomers.

Irreversible breakdown of BLMs suspended across conventional pipettes was observed at 418±18 mV. However, BLMs suspended on low energy perflourinated pipette surfaces surprisingly demonstrated reversible pore formation under a progressively increasing electric field ranging from 400-600 mV and much higher irreversible breakdown potentials. Without wishing to limit the present invention to a particular theory or mechanism, the high energy barrier within the pores and the improved interaction between the hydrophobic lipid tails and the aperture substrate may prevent the irreversible rupture of BLMs within the observed potential range (400-600 mV). In other cases, high viscosity in the lipid membrane may inhibit fast growth of the pores, thereby preventing irreversible breakdown of BLMs. At high electric fields (>900 mV), an irreversible rupture of BLMs often occurred.

When BLMs were doped with monomers, the accumulation of transient pores that preceded the irreversible rupture of the membranes suspended across CPDCS and PFDCS was observed at 493±59 and 520±119 mV respectively.

Table 6 shows physical and electrical properties of monomer doped BLMs suspended on low energy (PFDCS) silane-modified pipette apertures.

| Lipid Composition | UV (min) | $V_B$ (mV) | normalized conductance ($\times 10^{-2}$ pS $\mu m^{-2}$) | AWT | Longevity (h) | Longevity (h) with IC |
|---|---|---|---|---|---|---|
| DPhPC | 0 | 984 ± 210 | 9.00 ± 2.00 | >50 | 8 ± 1 | |
| DPhPC | 15 | 980 ± 254 | 8.49 ± 0.91 | >50 | 8 ± 1 | |
| DPhPC/ monomer (1:1) | 0 | 520 ± 119 | 4.95 ± 0.57 | 32 ± 11 | 6 ± 1 | 1-4 |
| DPhPC/ monomer (1:1) | 5 | 1398 ± 552 | 4.81 ± 0.14 | 36 ± 13 | 5, 7 | 8* |
| DPhPC/ monomer (1:1) | 10 | >2000 | 6.93 ± 1.08 | >50 | >15 | N/A |

*Although BLM was still intact after 7 h, the conductance of gramicidin IC decreased. This may be due to a number of reasons such as denaturing of the peptide IC under ambient temperature, effect of buffer and bias potential on the IC. A high probability of BLM rupture was observed for increasing numbers of insertions and channel activities in non-UV irradiated scaffolds.

Table 7 shows physical and electrical properties of monomer doped BLMs suspended across (CPDCS) silane-modified pipette apertures.

| Lipid Composition | UV (min) | $V_B$ (mV) | normalized conductance ($\times 10^{-2}$ pS $\mu m^{-2}$) | AWT | Longevity (h) |
|---|---|---|---|---|---|
| DPhPC | 0 | 460 ± 21 | 5.5 ± 1.7 | 4 ± 3 | 2 ± 1 |
| DPhPC | 15 | 575 ± 124 | 6 ± 3 | 6 ± 4 | 2 ± 1 |
| DPhPC/ monomer (1:1) | 0 | 493 ± 59 | 8.7 ± 0.5 | 20 ± 23 | 1, 2, 4 |
| DPhPC/ monomer (1:1) | 5 | 615 ± 107 | 10.7 ± 1.9 | >50 | 7, >30 |
| DPhPC/ monomer (1:1) | 10 | >2000 | 9.1 ± 0.8 | >50 | 14, >18 |

The electrical stability of conventional BLMs suspended across PFDCS modified glass pipette apertures before and after 15 min of UV irradiation (984±210 vs 980±254 mV respectively) were statistically the same, suggesting that UV irradiation had no chemical effect on non-polymerizable lipids. Additionally, the conductance, the number of AWTs and longevity were statistically the same before and after 15 minutes of UV irradiation for BLMs without monomers, confirming that UV irradiation had no effect on the structural organization of BLMs. When BLMs were doped with hydrophobic monomers, the electrical stability decreased by ca. 50%, which is possibly due to the interference of free monomers on the packing density of self-assembled lipid molecules.

Interestingly, the conductance decreased by ca. 50%. for monomer doped BLMs, suggesting that the necessary arrangement of the small hydrophobic monomers in the lamella region of the bilayer without the formation of domains thereby decreases the permeability of the membranes to conducting ions. In addition, the mechanical stability or the number of AWTs slightly decreased from >50 for BLMs without monomers to 32±11 upon introduction of monomers into the bilayer. In general, the observed decrease in the electrical and mechanical stability of monomer doped BLMs, and the decrease in temporal stability from 8±1 to 6±1, suggest that further weakening of the hydrophobic interaction between lipid molecules leads to a gradual collapse of the bilayer scaffold with time.

After 5 minutes of UV irradiation of the monomer doped BLMs, the electrical stability was improved by a factor of 3 from 520±119 to 1398±552 mV, while the mechanical stability was statistically the same before and after UV irradiation (32±11 to 36±13 respectively). The large standard deviation reported on the electrical stability of monomer doped BLMs after UV irradiation may be due to the variation in the amount of hydrophobic monomers that undergo cross-linking in the lipid bilayer in each individual experiment. There was no significant change in the conductance before and after 5 minutes of UV irradiation due to insufficient cross-linking in the BLM scaffold. Although the change in the conductance and mechanical stability of monomer doped BLMs before and after UV irradiation was indistinguishable, the observed increase in the electrical stability indicated cross-linking in BLMs through the hydrophobic monomers. Improvement in the temporal stability from 4 to >8 h also confirms cross-linking in BLMs. Further UV irradiation for 10 minutes showed a significant change in the electrical stability as observed by >4 fold increase in the breakdown voltage from 520±119 to >2000 mV before and after cross-linking. The mechanical stability of monomer doped BLMs suspended across PFDCS-modified apertures was improved by a factor of 2 after 10 minutes of UV irradiation.

Although traditional BLMs suspended across perfluorinated glass pipette apertures demonstrated enhanced electrical and mechanical stability, the introduction of small hydrophobic polymerizable monomers in BLMs further improved the electrical stability by overcoming the weak force of interaction within the lipid moieties via chemical cross-linking. The conductance of monomer doped BLMs before and after 10 min of UV irradiation increased from 4.81±0.14 to 6.93±1.08, suggesting a slight leakage in the bilayer, which is probably due to the formation of domains. Previous results demonstrated that polymeric lipid membranes that become leaky after cross-linking is cause by the lateral contraction of the lipids which leads to the formation of holes. During chemical cross-linking via UV irradiation, the bilayer undergoes a structural rearrangement. In the case where cross-linking occurs at only one end of an EGDMA monomer, instead of both ends, the lipid head groups are likely to be drawn together at the surface of the bilayer. Further, UV irradiation may trigger the reorganization of the molecules to result in either improved packing or domain formation.

Reconstitution of Protein Ion Channel into Monomer Doped BLMs

To validate the formation of lipid membranes with a bilayer thickness from a mixture of polymerizable monomers and non-polymerizable lipids, a protein was reconstituted and single-channel recording was monitored. Ion channels in cell membranes or model artificial lipid membranes serve as transducers for label-free chemical measurements of molecules and ions. Additionally, the reconstitution of protein ion channels provide an indication of successful formation of BLMs with thickness similar to cell membranes and the activity of the IC can be used to probe the lipid environment.

Robust ion channel-based biosensors and sequencing platforms necessitate high stability suspended lipid bilayers into which functional ion channels can be reconstituted. While PSS-BLMs showed significant stability improvements, the effects of UV irradiation and the presence of the polymer scaffold on the ion channel function was a major concern for the application of this technology. Gramicidin A, a channel forming peptide that requires membrane fluidity to function, was reconstituted into conventional BLMs, MA-BLMs, and PSS-BLMs to probe the relationship between methacrylate cross-linking and ion channel function.

The structure and function of Gramicidin A is one of the most well studied and described cation-selective channels. Gramicidin A forms an ion-conducting channel by the dimerization of the pentadeca peptide subunits which freely diffuse in each monolayer leaflet of a lipid bilayer. The dynamic process of formation and dissociation of transmembrane dimers of gramicidin A leads to a quantized change in current with conductance ranging from 21-24 pS. Owing to a shorter hydrophobic length of gramicidin (ca. 2.2 nm) than the hydrophobic thickness of BLM, the bilayer is locally deformed to allow dimerization of two gramicidin monomers to form pores (FIG. 4A).

Kelkar et al. reported the structure and function of gramicidin in a lipid bilayer to be dependent upon the oriented dipole moments of the four C-terminal tryptophan residues of the peptide (Kelkar, D. A.; Chattopadhyay, A. *Biochim. Biophys. Acta* 2007, 1768, 2011-2025). Thus changes in membrane properties upon PSS-BLM formation or degradation of C-terminal tryptophan residues during UV irradiation may lead to disruption of gramicidin A function.

To monitor IC insertion and activity, Gramicidin A was added to the cis side of a conventional BLM while applying a potential of 70 mV across the bilayer. Successful insertion and dimerization was indicated by quantized changes in ion current with amplitudes of ca. 1.5 pA. (FIG. 4B) for a single channel. Ion channel conductance states were calculated by dividing the mean of each distribution in the all-points histogram (FIG. 4C) by the applied potential. The resulting conductance states were separated by 21 pS, characteristic of normal gramicidin activity.

The formation of BLMs with thickness similar to cell membranes was crucial for monitoring the transport of ions across reconstituted ion channels. In the case where the thickness of BLMs exceeded that of cell membranes, measurement of IC current across the bilayer was impaired. Mueller and Montal reported the adverse effect of trapped hydrocarbon solvent within a bilayer leaflet on the insertion and activity of IC. Rovin and co-workers also demonstrated the dependence of membrane composition on the lifetime of gramicidin ion channels (Rudnev, V. S.; Ermishkin, L. N.; Fonina, L. A.; Rovin, Y. G. Biochim. Biophys. Acta 1981, 642, 196-202). Since the composition of the lipid bilayer greatly influenced the insertion, average lifetime, and gating of an ion channel, the effect of free monomers that partitioned in and out of the lipid bilayer and organic solvent within the annulus region or outside of bilayer was a major concern.

To evaluate the effect of monomer doped BLMs on the activity of ICs, gramicidin was reconstituted in DPhPC BLMs without monomers, and the IC activity was monitored before and after UV irradiation. Results in FIG. 5A-C show the reconstitution of gramicidin into DPhPC BLMs, followed by 5 minutes of UV irradiation and further irradiation at 10 minutes respectively. The conductance of IC decreased by ca. <20%, suggesting a slight photo-degradation of the tryptophan residue on gramicidin IC. There was no significant change in the mean open time of the IC after 5 and 10 minutes of UV irradiation.

Interestingly, channel activity was observed when gramicidin was reconstituted in equimolar monomer/lipid BLMs. The IC conductance in monomer doped BLMs that were not UV irradiated was reduced by 30% compared to gramicidin in DPhPC BLMs (FIG. 5D). The observed phenomenon was due to the interference of free monomer in the bilayer leaflet on the activity of gramicidin. The result also agreed well with the observed 50% decrease in electrical stability of BLMs when doped with monomers as shown in Table 8.

Table 8 shows conductance of IC under variable lipid bilayer environment.

| Ion channel activity in variable lipid environment | Conductance (pS) per active channel | Percent decrease |
|---|---|---|
| DPhPC Control | 20 | 0 |
| DPhPC with 5 min of UV | 16-18 | <20 |
| DPhPC with 10 min of UV | 16-18 | <20 |
| DPhPC/monomer (no UV) | 14 | 30 |
| IC in DPhPC/monomer before 5 min of UV | 11-20 | 0-45 |
| IC in DPhPC/monomer before 10 min of UV | 9 | 55 |
| 5 min (UV) of DPhPC/monomer before IC insertion | 20 | 0 |
| 10 min (UV) of DPhPC/monomer before IC insertion | 0 | |

FIGS. 5A-H shows the effect of chemical cross-linking in monomer doped BLMs on the reconstitution of gramicidin IC. After 5 minutes of UV irradiation, a slight recovery of the IC conductance was observed, which suggests the restriction of free monomers, thereby allowing for the diffusion of the neighboring IC due to fluidity in the bilayer. Further, UV irradiation for 10 minutes led to a 55% decrease in the conductance of IC as shown in FIG. 5F, which is due to decreased fluidity in the membrane, thereby affecting the free diffusion of IC monomers in the bilayer leaflet.

Owing to the fact that the conductance or current amplitude of gramicidin A in BLMs was not preserved after UV irradiation, the monomer doped BLMs were UV irradiated prior to IC insertion. The monomer doped BLMs were partially polymerized for 5 minutes before IC insertion. Gramicidin activity was successfully maintained in the partially polymerized monomer doped BLMs as shown in FIG. 5G, which indicates the existence of some level of fluidity in the lipid bilayer leaflets. Further, UV irradiation of the monomer doped bilayer for 10 minutes before incubation of IC resulted in no observable quantized change in current, suggesting that the decreased fluidity in BLM was due to excessive cross-linking (FIG. 5H). Overall, the incorporation of monomers into lipid leaflets extended the average lifetime of BLMs from 4 h prior to photopolymerization to >24 h after 10 minutes of UV irradiation.

FIG. 8 shows the effect of UV irradiation on gramicidin A activity in conventional, MA-BLMs and PSS-BLMs. Following insertion of active gramicidin channels, BLMs were UV irradiated immediately after the verification of ion channel activity. On both CPDCS- and PFDCS modified apertures, a decrease in mean open time was observed in conventional BLMs after UV irradiation for 5 min, but no further change was observed when UV irradiation time was increased from 5 to 10 min (Table 9). Additionally, a decrease in mean channel conductance was observed, and the effect was much larger on PFDCS-modified apertures. The observed decrease in gramicidin conductance and mean open time after UV irradiation may be attributed to photodegradation of C-terminal tryptophan, resulting in decreased activity as reported previously. Ion channel activity was observed when gramicidin was reconstituted in MA-BLMs; however, the mean conductance of gramicidin in MA-BLMs on CPDCS and PFDCS-modified apertures was reduced by 14% and 20%, respectively, compared to gramicidin in conventional BLMs. Thus, the presence of the monomer mixture has a moderate but adverse effect on gramicidin.

Table 9 shows gramicidin A activity in conventional BLMs, MA-BLMs, and PSS-BLMs.

| | | CPDCS | | PFDCS | |
|---|---|---|---|---|---|
| BLM configuration | UV Time (min) | Mean conductance (pS) | Mean open time (ms) | Mean conductance (pS) | Mean open time (ms) |
| Conventional BLMs | 0 | 21 ± 0.4 | 1067 ± 387 | 21 ± 0.6 | 1091 ± 291 |
| | 5 | 19 ± 3 | 668 ± 170 | 15 ± 2 | 625 ± 284 |
| | 10 | 17 ± 3 | 653 ± 124 | 14 ± 1 | 570 ± 197 |
| MA-BLMs | 0 | 19 ± 2 | 587 ± 313 | 17 ± 4 | 556 ± 305 |
| PSS-BLMs | 5 | 11 ± 1 | 118 ± 90 | 14 ± 2 | 586 ± 162 |
| | 10 | NA | NA | 5 ± 1.4 | NA |

NA = little or no ion channel activity observed.

Figures 8A, 8B, 8C, 8D, 8E, 8F:
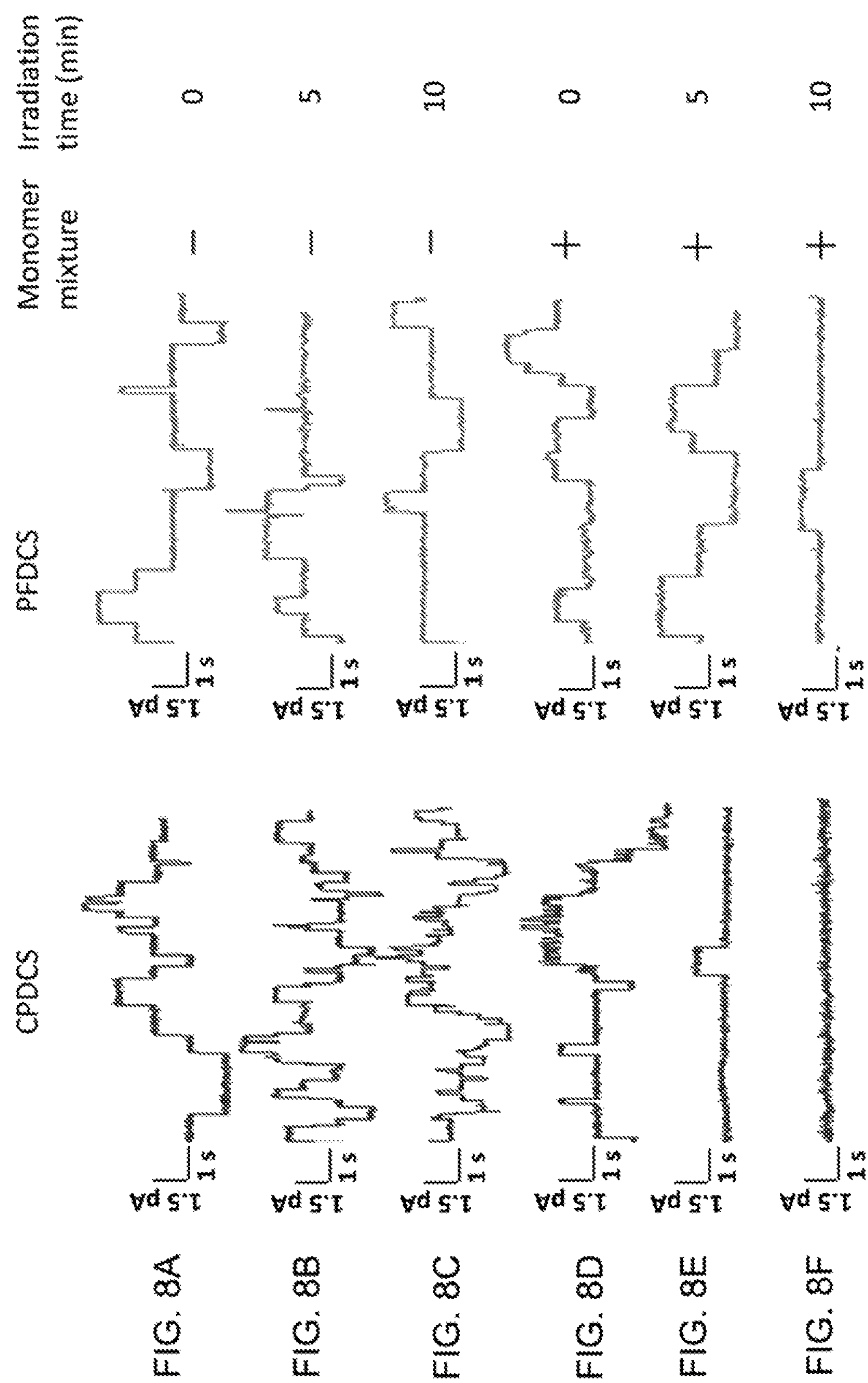
FIGS. 8A-8F show gramicidin A activity in varying BLM configurations on CPDCS-(blue) and PFDCS-(red) modified apertures. Conventional DPhPC BLMs containing gramicidin A were UV irradiated for 0 min (FIG. 8A), 5 min (FIG. 8B), and 10 min (FIG. 8C).
Figure 11A:
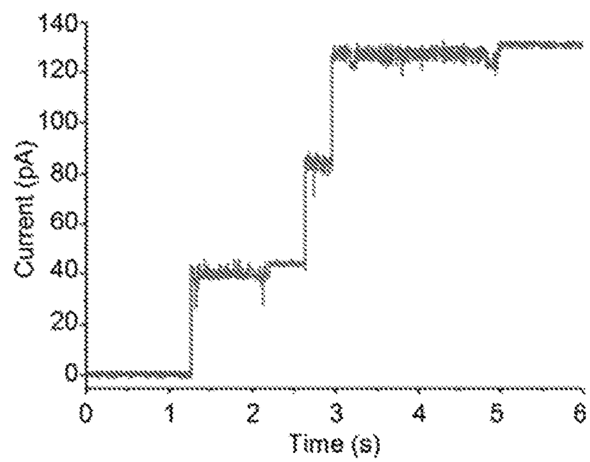
FIGS. 11A-11F show single ion channel recordings and all-points histograms of α-hemolysin (α-HL) in BLMs suspended on PFDCS-modified pipette apertures. As shown in 11A and 11B, single channel recordings and all-points histograms reveal multiple insertions of α-HL in a conventional BLM with characteristic conductance of ca. 1 nS per channel. In 11C and 11D, a single α-HL channel was allowed to insert into a MA-BLM, where the characteristic conductance of ca. 1 nS was observed. As shown in 11E and 11F, following 10 min UV-irradiation of the BLM to form a PSS-BLM, α-HL activity was unaffected by extended cross-linking within the membrane. All recordings were made at a holding potential of 40 mV.
Figure 11B:
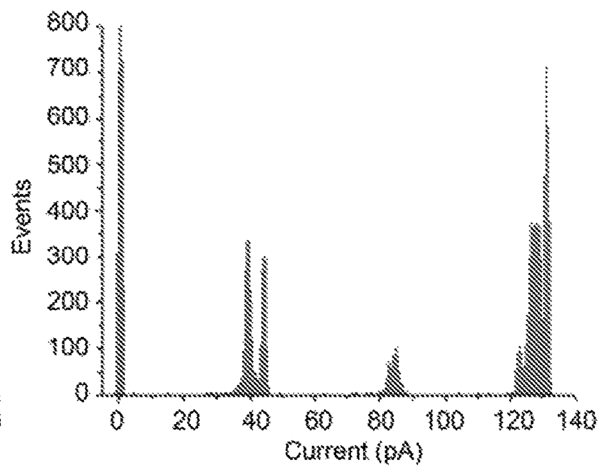
Figure 11C:
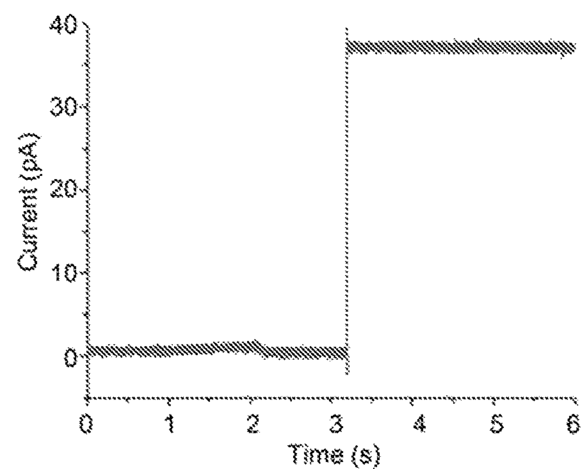
Figure 11D:
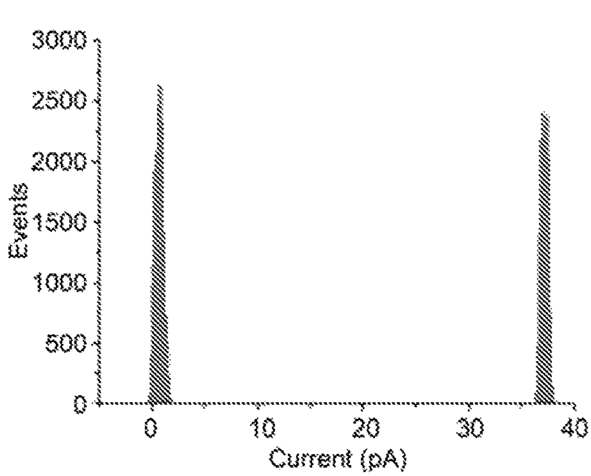
Figure 11E:
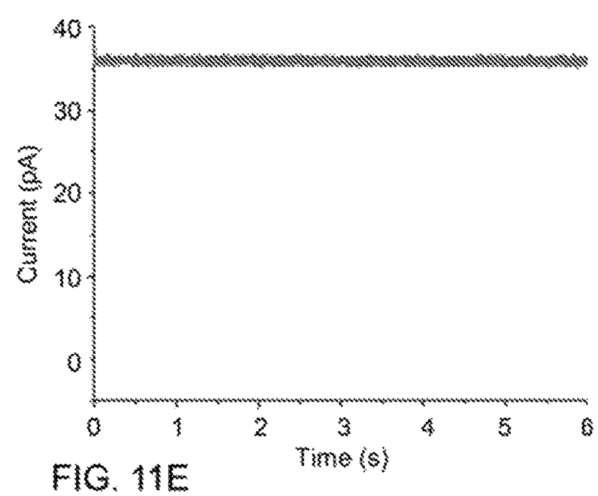
Figure 11F:
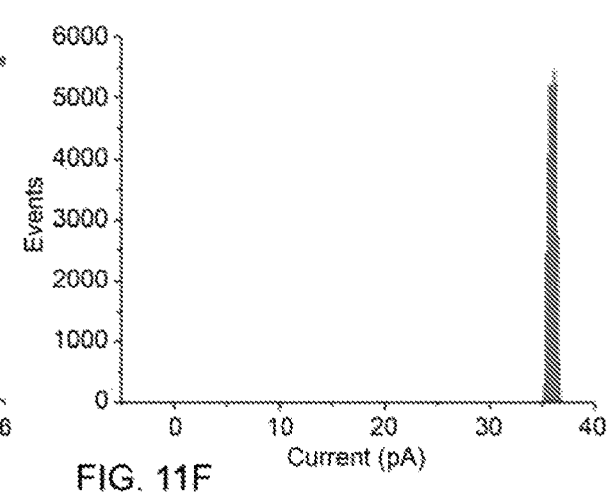
Figure 12:
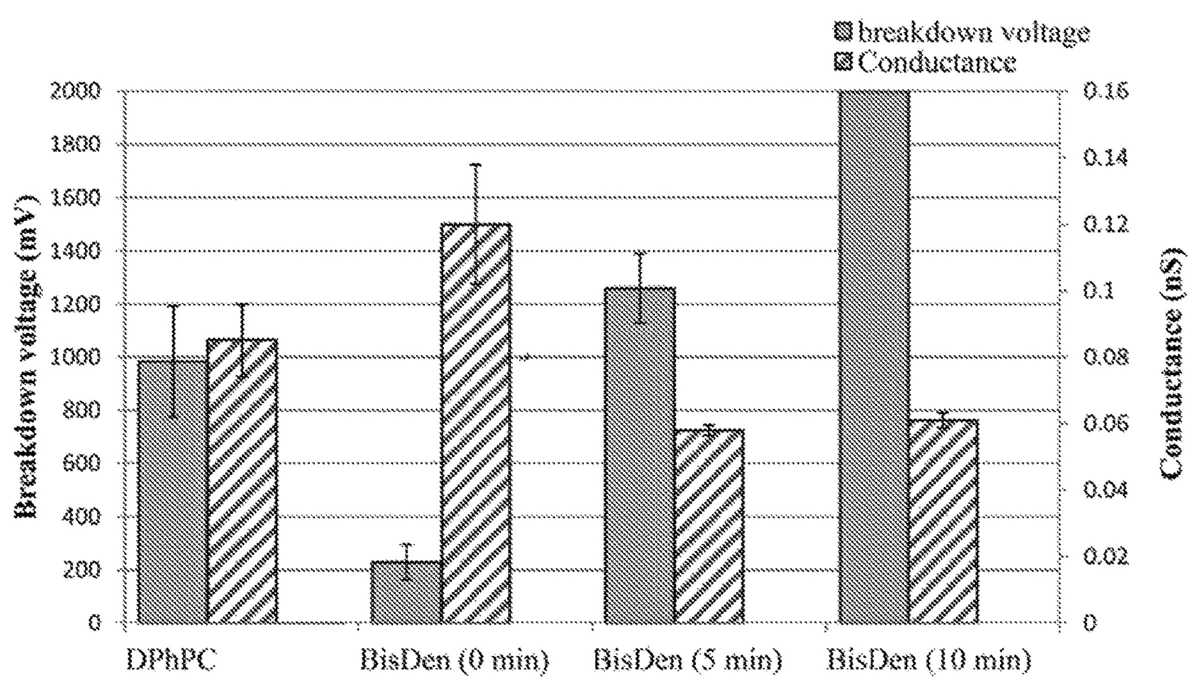
FIG. 12 is a bar graph showing the electrical stability of bis-DenPC BLMs before and after polymerization using a redox initiation solution containing $NaHSO_3$ and $(NH_4)_2S_2O_8$. The redox species react to generate radical prodcuts that initiate the polymerization reaction. Results indicate drastic increase in electrical stability indicated by breakdown voltage >2000 mV after 10 min of redox polymerization.

Upon 5 minutes of UV irradiation of MA-BLMs to form PSS-BLMs (FIG. 8E), gramicidin conductance was reduced by 48% and 35% for CPDCS- and PFDCS-modified apertures, respectively, relative to conventional BLMs. Extending UV irradiation time to 10 min resulted in the near total loss of gramicidin activity (FIG. 8F). Decreases in gramicidin conductance and mean open time upon PSS-BLM formation exceed those of UV-irradiated gramicidin in conventional BLMs, suggesting an additional mechanism of interference beyond photodegradation. It is suspected that the observed decreases in conductance are the net result of both photodegradation and reduced bilayer fluidity upon formation of the polymer scaffold. Additionally, the presence of the monomer mixture in MA-BLMs and the polymer scaffold in PSS-BLMs may alter the physical or mechanical properties of the membrane, thus attenuating the capability of the BLM to locally deform to accommodate formation of functional gramicidin conducting pores.

In an effort to circumvent the deleterious effects of UV irradiation and/or monomer mixture on gramicidin conductance, gramicidin was reconstituted into pre-formed PSS-BLMs (FIG. 9). Surprisingly, when PSS-BLMs were formed via 5 min of UV irradiation, gramicidin readily reconstituted into the stabilized bilayers (FIG. 9A) on both CPDCS- and PFDCS-modified apertures. Gramicidin conductance was only minimally affected under this condition (Table 10), with reductions of 14% and 3% for CPDCS and PFDCS-modified apertures, respectively, compared to conventional BLMs.

When PSS-BLMs were formed via 10 min of UV irradiation (FIG. 9B), no evidence of gramicidin reconstitution was observed. Combined, these results suggest that moderate UV irradiation times lead to partially polymerized methacrylate scaffolds that provide enhanced BLM stability and maintain bilayer fluidity adequate for peptide reconstitution and ion channel function. In contrast, excessive UV irradiation times (e.g., 10 min) result in more extensively polymerized scaffolds that decrease membrane fluidity and/or reduce the capability of the BLM to compress sufficiently to form functional gramicidin channels.

The observed number of functional ion channels provides an additional indication of the degree of fluidity and/or compressibility in PSS-BLMs. When gramicidin activity was observed in PSS-BLMs, no more than two active gramicidin channels were observed concurrently, compared to >6 in both conventional and MA-BLMs. Thus the probability of forming a functional dimer is decreased upon increased photopolymerization.

Table 10 shows gramicidin A activity when reconstituted in pre-formed PSS-BLMs.

| | | CPDCS | | PFDCS | |
|---|---|---|---|---|---|
| BLM configuration | UV Time (min) | Mean conductance (pS) | Mean open time (ms) | Mean conductance (pS) | Mean open time (ms) |
| PSS-BLMs | 5 | 19 ± 4 | 891 ± 147 | 20 ± 3 | 867 ± 167 |
| | 10 | NA | NA | NA | NA |

NA = no ion channel activity observed.

Importantly, gramicidin reconstituted into PSS-BLMs maintained function for 7-9 h before permanent loss of peptide function was observed, possibly due to peptide denaturation, as shown in FIG. 10 for single channel recordings. Thus, with membrane lifetimes that exceed those of reconstituted ICs, PSS-BLMs may offer a route towards IC-based biosensors that are limited not by membrane stability, but by the active lifetimes of reconstituted membrane proteins.

To broaden the application of PSS-BLM ion channel platforms, α-HL was reconstituted, a pore forming channel with characteristic conductance of ca. 1 nS into the various BLM configurations. α-HL is routinely used to prepare stochastic sensors and nucleic acid sequencing platforms, thus it represents an important application for stabilized BLMs. Table 11 summarizes the results obtained for α-HL reconstituted into differing BLM configurations. In each case, the mean conductance values for α-HL were within the accepted experimentally measured values as shown in FIG. 11, suggesting that UV irradiation or decreased membrane fluidity had no adverse effect on α-HL activity.

α-HL is a homoheptamer that requires insertion and assembly of the seven monomer units to form the functional channel. Thus, the membrane must retain sufficient fluidity to support diffusion and assembly of the channel subunits. Reconstitution of α-HL into pre-formed PSS-BLMs via 5 min of UV irradiation further confirms the existence of sufficient fluidity required for ion channel reconstitution and function, similar to that observed for gramicidin A, whereas no evidence of functional ion channel assembly was observed after extended cross-linking via 10 min of UV irradiation (Table 12). Overall, reconstitution of ion channels into pre-formed PSS-BLMs prepared via 5 min of photopolymerization show great promise for the construction of ion channel functionalized sensor technologies.

Importantly, UV-photopolymerization might also be useful to limit the number of α-HL insertions into the BLM. In typical α-HL reconstitutions, an excess of ion channel is added to the bath and immediately upon insertion of a functional channel, the bath is diluted. Thus polymerization of the PSS-BLM may provide an easily automated alternative approach for controlling ion channel insertion density, if the excessive electrical noise introduced by the UV lamp can be overcome.

Table 11 shows α-HL activity in conventional BLMs, MA-BLMs, and PSS-BLMs on PFDCS-modified pipette apertures.

| BLM Configuration | UV time (min) | Mean conductance (nS) |
|---|---|---|
| Conventional | 0 | 0.80 ± 0.32 |
| BLMs | 5 | 0.88 ± 0.11 |
| | 10 | 0.89 ± 0.090 |
| MA-BLMs | 0 | 0.95 ± 0.034 |
| PSS-BLMs | 5 | 0.92 ± 0.033 |
| | 10 | 0.93 ± 0.029 |

Table 12 shows α-HL activity reconstituted in pre-formed PSS-BLMs on PFDCS-modified pipette apertures.

| BLM Configuration | UV time (min) | Mean conductance (pS) |
|---|---|---|
| PSS-BLMs | 5 | 0.94 ± 0.068 |
| | 10 | NA |

NA = no ion channel activity observed.

Finally, it should be noted that while direct insertion of ion channels used here was readily achieved, insertion of more hydrophobic channels typically requires either surfactant dialysis or fusion of proteolysosomes.

Conclusion

The stability of lipid bilayers suspended across glass pipette apertures is dependent on the underlying surface energy of the aperture and the interactive force existing between the lipid molecules. The use of low surface energy (PFDCS) modifiers enhanced the mechanical, electrical and temporal stability of BLMs compared to conventional pipettes. The lifetime of BLMs was improved from 8 to >15 h by overcoming the weak noncovalent interactions among lipid molecules via chemical cross-linking using small hydrophobic non-lipid monomers. Monomers doped into BLMs without cross-linking decreased the stability of BLMs by 50% due to the interference of free monomers on the self-assembled lipid interactions. However, UV irradiation to convert the monomers to a polymeric network further improved the electrical stability of BLMs by a factor of 3 and >4 for 5 and 10 minute irradiations respectively.

In addition, UV irradiation of BLMs after the reconstitution of ICs resulted in the photolytic degradation of IC indicated by a decrease in current amplitude. Partial cross-linking in monomer doped BLMs for 5 minutes allowed for the insertion and free diffusion of IC without any deleterious effect on the conductance, which is due to preserved fluidity in BLMs. UV irradiation for 10 minutes resulted in the loss of fluidity in BLMs, which was confirmed by the inability to reconstitute ICs. Thus, partial polymerization was necessary to maintain fluidity and stability of BLMs, while allowing for the reconstitution of ICs. The improved IC scaffold by partial cross-linking using commercially available monomers is promising for the development of the next generation of robust, BLM-based, ion channel sensors.

Furthermore, improved stability of BLMs can be attained by chemically cross-linking methacrylate monomers within the lipid membranes to form PSS-BLMs. This approach is simpler, broadly applicable, less costly and more widely accessible compared to prior efforts utilizing reactive lipid monomers. PSS-BLMs can withstand potentials >2000 mV without experiencing dielectric breakdown and show >10 fold increase in measures of mechanical stability and >5 fold increase in BLM lifetime compared to conventional BLMs, with no deleterious effect on membrane integrity or structure. The average membrane lifetime was improved such that the lifetime of the reconstituted ion channel, gramicidin A, and not the BLM lifetime, was the fundamental limitation on sensor lifetime. PSS-BLMs offer stability advantages similar to those obtainable with polymerizable lipids but with few of the associated limitations. Thus, PSS-BLMs can offer substantial advantages for ion channel-based sensors and other BLM technologies, and may address the limitations of membrane stability on the development of these technologies.

Section 2A

Referring now to FIGS. 15-31, the present invention features a stabilized, supported lipid bilayer system. The system may comprise a supporting substrate and a stable, polymeric lipid bilayer comprising a plurality of polymerized lipid monomers. The lipid bilayer may be disposed on the supporting substrate. In one embodiment, the system may further comprise membrane proteins integrated into the lipid bilayer. In another embodiment, the system may further comprise an affinity platform. The affinity platform may be a chromatography column, such as an open-tubular capillary chromatography column or a packed-bed chromatography column.

An embodiment of the present invention may feature a stabilized, supported lipid bilayer system for use in a chromatography column comprising the chromatography column, a supporting substrate, and a stable, polymeric lipid bilayer comprising a plurality of polymerized lipid monomers and disposed on the supporting substrate. Preferably, the lipid monomers are polymerized at a near neutral pH using a redox polymerization mixture comprising $NaHSO_3$ and an initiator-buffer component. The initiator-buffer component functions to initiate redox polymerization and to buffer the redox polymerization mixture.

Another embodiment of the present invention may feature a method of producing a stabilized, supported lipid bilayer system. For example, the method may comprise obtaining a plurality of polymerizable lipid monomers, obtaining a supporting substrate, depositing the lipid monomers onto the supporting substrate such that the lipid monomers form a lipid bilayer on the supporting substrate, and polymerizing the lipid monomers to increase a stability of the lipid bilayer. Teh method may further comprise integrating membrane proteins into the lipid bilayer prior to polymerizing the lipid monomers.

In an alternative embodiment, the method may comprise obtaining a plurality of polymerizable lipid monomers, obtaining a supporting substrate, depositing the lipid monomers onto the supporting substrate to form a lipid bilayer on the supporting substrate, and polymerizing the lipid monomers to increase the stability of the lipid bilayer using a redox polymerization mixture comprising an initiator-buffer component and $NaHSO_3$. The initiator-buffer component can initiate polymerization of the lipid monomers and buffer the redox polymerization mixture to maintain a near neutral pH during polymerization of the lipid monomers. In other embodiments, the method may further comprise integrating membrane proteins into the lipid bilayer prior to polymerizing the lipid monomers. Preferably, the activity and native conformations of the proteins are maintained after polymerization of the lipid monomers.

Another embodiment of the present invention features a chromatography column packed with microparticles having a polymeric lipid bilayer disposed on a surface of each microparticle. The lipid bilayer may comprise polymerized lipid monomers.

In an alternative embodiment, the present invention features a chromatography column comprising a polymeric lipid bilayer deposited on an inner surface of the chromatography column. The chromatography column may be an open-tubular capillary column. The lipid bilayer may comprise polymerized lipid monomers disposed on (i.e. covering) at least about 50% of the inner surface of the chromatography column.

The present invention may also feature an embodiment comprising a method of preparing a packed chromatography column. The method may comprise providing a chromatography column, preparing a plurality of vesicle-coated microparticles, and packing the vesicle-coated microparticles inside the chromatography column. In an exemplary embodiment, preparing said vesicle-coated microparticles may comprise obtaining a plurality of polymerizable lipid monomers, obtaining a plurality of microparticles, depositing the lipid monomers onto each microparticle such that the lipid monomers form a lipid bilayer on a surface of each microparticle, and polymerizing the lipid monomers of each lipid bilayer using a redox polymerization mixture to form a stable, polymeric vesicle coating on each microparticle. Preferably, the redox polymerization mixture may comprise an initiator-buffer component and $NaHSO_3$. The initiator-buffer component initiates polymerization of the lipid monomers and buffers the redox polymerization mixture to maintain a near neutral pH during polymerization of the lipid monomers. In other embodiments, the method may further comprise integrating membrane proteins into the lipid bilayer prior to polymerizing the lipid monomers. The activity and native conformations of the proteins are maintained after polymerization of the lipid monomers.

The present invention may further feature a kit for preparing a stabilized, supported lipid bilayer system. The kit may comprise at least one supporting substrate, a plurality of polymerizable lipid monomers, and a redox polymerization mixture comprising an initiator-buffer component and $NaHSO_3$. To prepare the lipid bilayer system, the lipid monomers are deposited onto the supporting substrate such that the lipid monomers form a lipid bilayer on the supporting substrate and the lipid monomers are polymerized using the redox polymerization mixture to increase stability of the lipid bilayer. Preferably, the initiator-buffer component initiates polymerization of the lipid monomers and buffers the redox polymerization mixture to maintain a near neutral pH during polymerization of the lipid monomers. In some embodiments, the kit may further comprise an affinity platform. The affinity platform is a chromatography column, such as an open-tubular capillary chromatography column or a packed-bed chromatography column. In one embodiment, the supporting substrate is an inner wall of the open-tubular capillary column. In another embodiment, the supporting substrate comprises a plurality of microparticles.

In one embodiment, when the chromatography column is an open-tubular capillary chromatography column, the supporting substrate may be an inner wall of the open-tubular capillary column. In another embodiment, when the chromatography column is a packed-bed chromatography column, the supporting substrate may comprise a plurality of microparticles. In some embodiments, the supporting substrate has a planar or curved surface. In other embodiments, the lipid bilayer may be disposed on a surface of each microparticle to form a vesicle-coated microparticle.

In some embodiments, the lipid bilayer covers at least about 50% of the inner surface of the chromatography column. In some embodiments, the lipid bilayer covers at least about 60% of the inner surface of the chromatography column. In some embodiments, the lipid bilayer covers at least about 70% of the inner surface of the chromatography column. In some embodiments, the lipid bilayer covers at least about 80% of the inner surface of the chromatography column. In some embodiments, the lipid bilayer covers at least about 90% of the inner surface of the chromatography column.

In some embodiments, the chromatography column is an open-tubular capillary chromatography column or a packed-bed chromatography column. In some embodiments, the chromatography column can be any dimension.

In some embodiments, the supporting substrate is a micro-particle. In some embodiments, the supporting substrate is an inner wall of the open-tubular capillary column. In some embodiments, the supporting substrate is planar or curved. In some embodiments, the supporting substrate is a vesicle.

In some embodiments, the lipid bilayer covers at least 50% of the surface of each micro-particle. In other embodiments, the lipid bilayer covers at least 60% of the surface of each micro-particle. In still further embodiments, the lipid bilayer covers at least 70% of the surface of each micro-particle. In some embodiments, the lipid bilayer covers at least 80% of the surface of each micro-particle. For example, the lipid bilayer covers at least 90% of the surface of each micro-particle. In some embodiments, the micro-particles are silica micro-particles or metal-oxide particles.

In some embodiments, a diameter of the micro-particles is between about 0.5 μm to 40 μm. In some embodiments, a diameter of the micro-particles is between about 0.5 μm to 30 μm. In some embodiments, a diameter of the micro-particles is between about 10 μm to 30 μm. In some embodiments, a diameter of the micro-particles is between about 20 μm to 30 μm. In some embodiments, a diameter of the micro-particles is between about 30 μm to 40 μm.

In some embodiments, the lipid monomers are sorbyl- or dienoyl-containing lipid molecules, mono-functionalized lipid molecules or lipid molecules containing one or more polymerizable dienoyl groups. In some embodiments, the dienoyl-containing lipid molecule is 1,2-bis[10-(2',4'-hexadieoyloxy)decanoyl]-sn-glycero-2-phosphocholine (bis-SorbPC) or 1,2-bis(octadeca-2,4-dienoyl)-sn-glycero-3-phosphocholine (bis-DenPC). In other embodiments, the mono-functionalized lipid molecule is mono-dienoylphosphatidylcholine (mono-DenPC) or mono-sorbylphophostidylcholine (mono-SorbPC).

In some embodiments, the lipid monomers can be polymerized by UV irradiation, visible irradiation, gamma irradiation, redox polymerization, or thermal polymerization. When the lipid monomers are polymerized by UV or visible irradiation, the lipid bilayer may further comprise photoinitiators. In some embodiments, the duration of UV irradiation or visible irradiation is sufficient to photopolymerize the lipid monomers and/or the photoinitiators. In preferred embodiments, the duration of irradiation is between about 1 to 30 minutes. In some embodiments, the duration of UV irradiation is between about 5 to 30 minutes. In other embodiments, the duration of UV irradiation is between about 10 to 30 minutes, or between about 15 to 30 minutes, or between about 20 to 30 minutes.

In some embodiments, the lipid monomers are polymerized by redox polymerization. A redox polymerization mixture comprising an initiator-buffer component and $NaHSO_3$ may be used for redox polymerization. In some embodiments, the redox polymerization mixture comprises any redox mixture that polymerizes the lipid monomers, i.e. a mixture having a reductant and an oxidant. In preferred embodiments, the initiator-buffer component comprises ammonium persulfate. Suitable mole ratios of ammonium persulfate, $NaHSO_3$, and lipids can include about 10-500 AP: 10-500 $NaHSO_3$:1 lipid, about 50-400 AP: 50-400 $NaHSO_3$: 1 lipid, or about 100-300 AP: 100-300 $NaHSO_3$: 1 lipid.

Preferably, the redox polymerization mixtures allows for the reaction to occur at a near neutral pH and to maintain a constant pH. In some embodiments, the redox polymerization occurs at a pH between about 5 to 9. In other embodiments, the redox polymerization occurs at a pH between about 5.5 to 7.5. In still other embodiments, the redox polymerization occurs at a pH between about 6 to 7.

EXPERIMENTAL 1,2-bis[10-(2',4'-hexadieoyloxy)decanoyl]-sn-glycero-2-phosphocholine (bis-SorbPC, $T_m$=29° C.) was synthesized according to previous protocols. Before use, a 0.5 mL aliquot of 18 mg $mL^{-1}$ bis-SorbPC in 7:3 (v/v) MeOH:$H_2O$ was purified on a $C_{18}$ column (Shimadzu Chromegabond WR $C_{18}$, 5 μm, 250 mm×23 mm) using a 10 mL $min^{-1}$ gradient (Shimadzu BCM-20A controller and LC-8A pumps) of $H_2O$ and MeOH. The MeOH volume in the mobile phase was increased from 50-70% in the first minute, increased from 70-85% over the next 20 min, increased from 85-100% over the next 40 min, and held at 100% for 5 min. The column was then flushed with 5% MeOH and 70% MeOH. All changes in the gradient were linear. The bis-SorbPC fraction was collected (elution time=40 min), dried under vacuum, and washed 3 times with chloroform before dissolving in 500 μL chloroform. The concentration of bis-SorbPC was determined by UV absorbance at 258 nm (∈=47100 $M^{-1}$ $cm^{-1}$ in MeOH) (Model 440CCD Array UV-Vis Spectrophotometer; Spectral Instruments, Inc., Tucson, Ariz.). Purified bis-SorbPC was stored at −80° C. Sorbyl functional groups are light sensitive; thus, purification and preparation of bis-SorbPC-coated particles were performed under UV-free, yellow light.

1,2-dioleoyl-sn-glycero-3-phosphocholine (DOPC, $T_m$=−17° C.) was purchased from Avanti Polar Lipids (Alabaster, Ala.). 3 μm silica particles (10% in water) were purchased from Polysciences, Inc. (Warrington, Pa.). FM1-43 was purchased from Invitrogen (Eugene, Oreg.). $K_2S_2O_8$, $NaHSO_3$, and $(NH_4)_2S_2O_8$ were purchased from Sigma (St. Louis, Mo.). All other chemicals were purchased from Fisher (Pittsburgh, Pa.). $H_2O$ was obtained from a Barnstead EasyPure UV/UF purification system. Buffers were filtered using membranes with 0.2 μm pores before use.

The chloroform from lipid stock solutions (DOPC and bis-SorbPC) was evaporated under Ar and lipids were dried by vacuum overnight (FreeZone 6, Labconco, Kansas City, Mo.). Lipid-coated particles were prepared by vesicle fusion. Briefly, dried lipids were suspended in phosphate buffered saline (PBS), pH 7.4, to a concentration of 1 mg $mL^{-1}$. Lipid solutions were sonicated at 40% output power until clarity using a cup horn sonicator (Model W-380, Heat Systems-Ultrasonics, Inc., Newtown, Conn.) to produce small unilamellar vesicles (SUVs). Silica particles (3.0 μm diameter) were added to the SUV solution at a surface area ratio of 1 silica:6 lipid. The mixture was sonicated for 5 min and then allowed to rest for 30 min to promote vesicle fusion. Vesicle formation and fusion onto silica were performed at 35° C., above the phase transition temperature of both lipids. For some studies, 5 μm diameter silica particles were used and the lipid deposition was performed at room temperature using a UV pen lamp for 30 min at a lipid to surface area ratio of 1 silica:25 lipid.

Bis-SorbPC-coated particles were polymerized by one of three methods. Before all polymerizations, the lipid/silica solutions were degassed by bubbling $N_2$ for 10 min. UV-polymerized particles were irradiated with a 100 W Hg Arc lamp with an IR-water filter and a band pass filter (U-330, Edmund Optics, Barrington, N.Y.) for 30 min while stirring. Redox polymerizations were performed using two different methods. Bis-SorbPC-coated particles were polymerized in the presence of 65 mM $K_2S_2O_8$ and 22 mM $NaHSO_3$ for 3 h at 35° C. or at a mole ratio of 1 lipid:300 $(NH_4)_2S_2O_8$: 300 $NaHSO_3$ for 1 h at 35° C. After preparation (DOPC-coated particles) or polymerization (bis-SorbPC-coated particles) each set of particles was washed by 6 cycles of centrifugation, removal of supernatant, and suspension in fresh PBS buffer.

Particles were packed in capillaries (50 μm or 75 μm i.d.; 360 μm o.d.; Polymicro Technologies, Phoenix, Ariz.) against Microtight filter assemblies (Upchurch Scientific, Oak Harbor, Wash.). Particles were slurried in PBS and packed at 1000 psi $N_2$ until an 8 cm packed bed was formed (50 μm) or at 560 psi He (75 μm). After packing, the $N_2$ tank was turned off and the pressure was allowed to slowly decrease by bleeding out of the capillary over the next 1 h.

Aliquots of particles were treated on days 1, 2, 15, and 30 with triton X-100 or acetonitrile to monitor the stability of the lipid bilayer. Particles were aliquoted into individual tubes, centrifuged, and suspended in fresh PBS, pH 7.4, at $1.8\times10^7$ particles per 100 μL. Particles were treated with 25 μL of 50 mM triton X-100 at room temperature for 15 min or with 50% acetonitrile (v/v) and sonicated for 15 min. After incubation, particles were rinsed by 4 cycles of centrifugation, removal of supernatant, and suspension in fresh PBS to a final concentration of $1.8\times10^8$ particles $mL^{-1}$.

FM1-43 was added to a particle slurry at a final concentration of 57 nM and allowed to intercalate into the lipid bilayer before imaging. Fluorescent images of particles were acquired on a Nikon Eclipse TE300 Quantum inverted microscope using a 40×/1.30 N.A. oil objective. Fluorescent images were obtained using rhodamine filters: $\lambda_{ex}$=540/25 nm; $\lambda_{em}$=620/60 nm. Images were collected using a Quantix 57 back-illuminated CCD camera (Roper Scientific, Tucson, Ariz.) operated by MetaVue imaging software (Universal Imaging, Downingtown, Pa.). Images were analyzed using Image J. Data is presented as the mean±standard deviation (graphically represented as error bars) for n=3×100, with the intensity of 100 particles quantified for each of three batches of particles that were prepared separately.

Packed capillary columns were imaged with or without FM1-43, which was allowed to intercalate into the bilayers before excess was rinsed away. Images were acquired using the instrument described above, but with a 4×/0.13 N.A. objective. Data is presented as the mean±standard deviation for n=3×3, 3 measurements from 3 capillaries.

Flow cytometric analysis was performed using a FACScan flow cytometer (BD Biosciences, San Jose, Calif.) equipped with an air-cooled 15 mW $Ar^+$ laser tuned to 488 nm. The emission fluorescence of FM1-43 was detected and recorded through a 582/42 nm bandpass filter in the FL2 channel. Data files consisting of approximately 50,000 events gated on forward scatter versus side scatter were acquired and analyzed using CellQuest PRO software (BD Biosciences). Appropriate electronic compensation was adjusted by acquiring particle populations with and without FM1-43. Data is presented as the average±standard deviation for n=3×50,000, with 50,000 gated events quantified for each of three batches of particles that were coated and polymerized independently.

Frontal chromatography was performed using a lab-built instrument. Isocratic elution with PBS, pH 7.4, as the mobile phase utilized pressure driven flow that was applied by a Micropro Syringe Pumping System (Eldex, Napa, Calif.) connected to a Cheminert injection valve (Valco, Houston, Tex.) with a 600 nL sample loop. The eluent was pumped at 1 μL $min^{-1}$ at room temperature, resulting in 2750±50 psi when a packed column was present in the instrument. The elution profile was monitored by ultraviolet absorbance detection (Model 500 Detector, ChromTech, Apple Valley, Minn.) at 220 nm. Signal from the detector was collected with an A/D converter (NI USB-6221, National Instruments, Austin, Tex.) and software written in LabVIEW (National Instruments). All samples were prepared at a concentration of 100 μM in PBS buffer, pH 7.4. Statistical significance was determined using the two-tailed Student's t-test.

Results and Discussion

Fusing small unilamellar vesicle (SUV) with a hydrophilic, silica surface results in rapid rupture of the vesicles to form a supported bilayer. Bilayer formation via vesicle fusion results from a balance between the increase in adhesion energy and loss of curvature energy during adsorption, deformation, and rupture of the vesicles. The process is dependent on the support material, the type of lipid, the size of the vesicles, and the aqueous environment (e.g., presence of dissolved salts).

Figure 15:
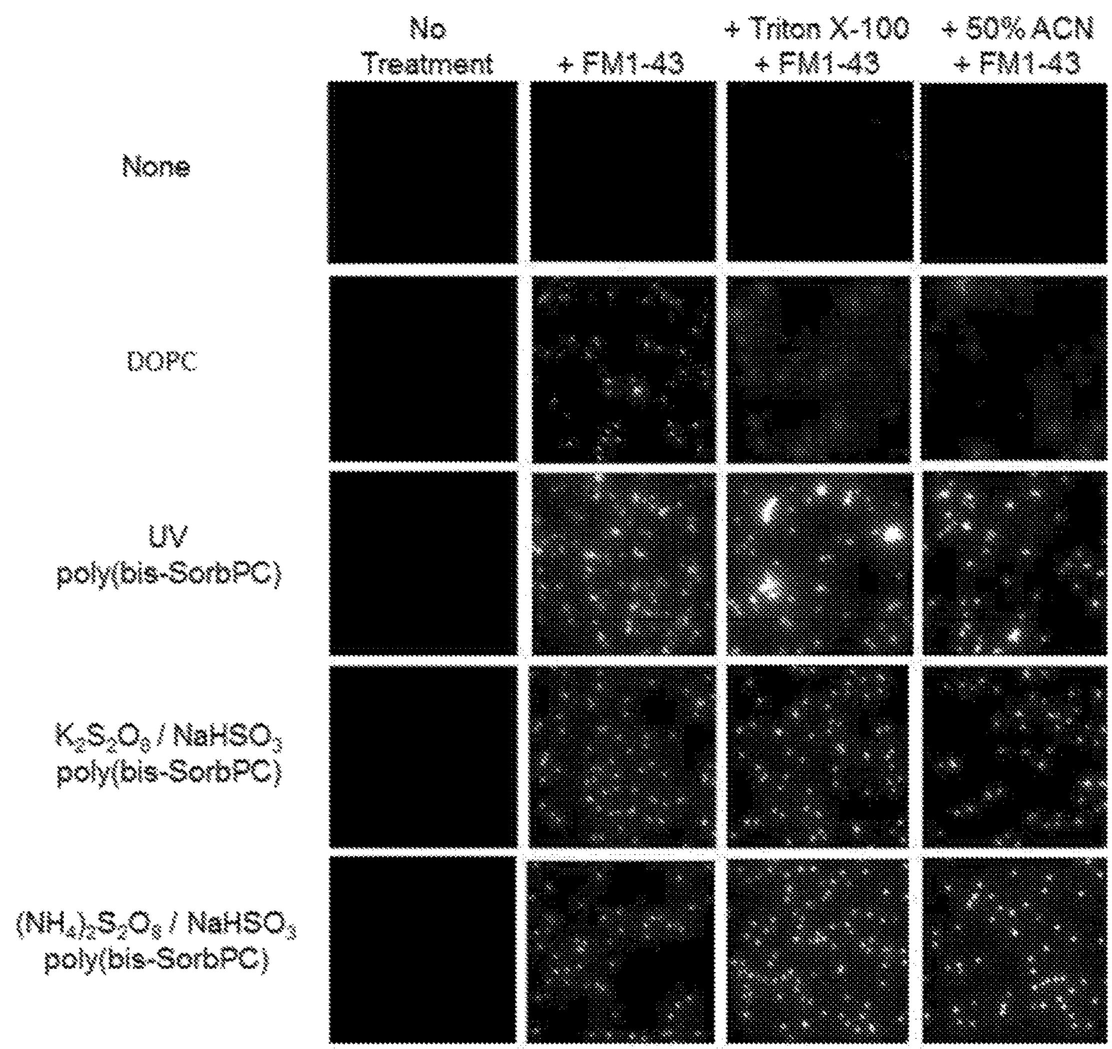
FIG. 15 shows representative fluorescence images of silica particles, DOPC-coated particles, and poly(bis-SorbPC)-coated particles, with UV, $K_2S_2O_8/NaHSO_3$, and $(NH_4)_2S_2O_8/NaHSO_3$ referring to the bis-SorbPC polymerization method. After incubation with FM1-43, DOPC-coated and poly(bis-SorbPC)-coated particles exhibit increased fluorescence, indicating the presence of lipid bilayers on the surface of the particles. After exposing the lipid-coated particles to surfactant (triton X-100) or organic solvent (acetonitrile, ACN), washing, and staining with FM1-43, only the poly(bis-SorbPC)-coated particles exhibit fluorescence, illustrating that the poly(bis-SorbPC) coatings are maintained after exposure to these insults and have greater chemical stability than unpolymerized DOPC coatings.

FIG. 15 shows fluorescent images of silica and lipid-coated silica particles after staining with a lipid indicator, FM1-43. Previous studies with FM1-43 have illustrated high levels of fluorescence after intercalation of the dye into lipid membranes. For comparison, both bis-SorbPC and DOPC, a natural lipid, were used to evaluate the stability of bilayer coatings. Natural phospholipid bilayers are unstable when exposed to common column preparation and/or separation conditions, including organic solvents, air bubbles, and shear forces; thus, the stability of lipid bilayer coatings were examined first to ensure the bilayers would be compatible with separation systems.

Silica (non-coated) particles, DOPC-coated particles, and poly(bis-SorbPC)-coated particles exhibited low fluorescence background prior to addition of FM1-43. After incubation with FM1-43, the fluorescence intensity of DOPC- and poly(bis-SorbPC)-coated particles increased, indicating the presence of lipid membranes on the surfaces of these particles. Additionally, the uniform fluorescence intensity indicates the presence of a bilayer membrane on the particle surface. To test the stability of the lipid bilayer coating, particles were exposed to surfactant (Triton X-100) or a high concentration of organic solvent (50% (v/v) ACN), washed, and then stained with FM1-43. These conditions, while more harsh than would be expected for most analyses involving lipid stationary phases, were chosen to provide a clear indication of the stability enhancements that might be obtained utilizing poly(lipid) membranes. The fluorescence intensity of DOPC-coated particles decreased significantly after exposure to surfactant or organic solvents, suggesting that the lipid bilayers were degraded. However, when poly(bis-SorbPC)-coated particles were exposed to either insult, the fluorescence intensity was retained after staining with FM1-43, indicating the enhanced bilayer stability after polymerization of the lipids.

To increase the throughput of particle characterization, flow cytometry was used to study large groups of particles since the scatter associated with each particle could be correlated with the fluorescence. Table 13 shows the mean fluorescence intensity of silica, DOPC-coated, and poly(bis-SorbPC)-coated particles in the presence and absence of FM1-43 and after treatment with surfactant or organic solvent. This data correlates well with the images presented in FIG. 15. Silica particles had low fluorescence under all conditions since lipids were not present on the particle surface. DOPC-coated particles exhibited increased fluorescence when stained with FM1-43 due to the presence of a lipid membrane; however, the bilayer coatings were unstable after exposure to surfactants or organic solvents as evidenced by the decreased fluorescence intensity following these conditions. When bis-SorbPC was polymerized using the UV or either redox initiation approach (with $K_2S_2O_8$ or $(NH_4)_2S_2O_8$ and $NaHSO_3$), the bilayer coating resulted in fluorescence when stained with FM1-43. Additionally, the fluorescence was retained after exposure to surfactants or organic solvents, illustrating the enhanced stability of the bilayer coating after polymerization.

Table 13 shows chemical stability of lipid bilayer coatings analyzed by flow cytometry.

| | Particle Fluorescence | | | |
|---|---|---|---|---|
| Silica Particle Coating | No Treatment | +FM1-43 | +Triton X-100 + FM1-43 | +50% ACN + FM1-43 |
| None | 3 ± 3 | 4 ± 4 | 8 ± 8 | 5 ± 4 |
| DOPC | 3 ± 1 | 670 ± 190 | 23 ± 19 | 46 ± 54 |
| UV poly(bis-SorbPC) | 4 ± 2 | 890 ± 100 | 630 ± 140 | 730 ± 100 |
| $K_2S_2O_8$/ $NaHSO_3$ poly(bis-SorbPC) | 3 ± 1 | 1000 ± 160 | 1100 ± 280 | 1200 ± 230 |
| $(NH_4)_2S_2O_8$/ $NaHSO_3$ poly(bis-SorbPC) | 3 ± 1 | 1300 ± 290 | 1400 ± 230 | 1400 ± 300 |

In addition to examining the stability of the bilayer coatings against common chemical insults, the long-term stability was analyzed by imaging. Particles were stained with FM1-43 prior to each experiment. Images were collected on the day of preparation, and again on days 15 and 30. Between experiments, particles were dispersed in PBS, pH 7.4, and stored at 4° C. The data in FIG. 2 shows that the poly(bis-SorbPC)-coated particles exhibited similar fluorescence intensities over the 30 day period, suggesting that the membranes were retained throughout this time frame. The polymerized bilayer coatings were also stable to surfactants and organic solvents over this duration, signifying that storage does not affect the stability of the bilayer coating. For the DOPC-coated particles, the fluorescence intensity was quantified only on the first day. Images of DOPC-coated particles collected on day 15 showed few fluorescent particles, indicating the bilayer coatings degraded during storage. The temporal stability of the poly(bis-SorbPC) membranes on silica particles was further supported by flow cytometry (FIG. 19). The long-term stability of poly(bis-SorbPC) membrane coatings suggests that columns packed with these particles could be stored for a period of time without degradation of the stationary phase or the need to regenerate the column.

The physical stability of the bilayer coatings was analyzed by imaging capillaries packed with UV poly(bis-SorbPC)-coated silica particles, DOPC-coated silica particles, or bare silica particles in the presence or absence of FM1-43 (FIG. 17). Only the capillaries packed with poly(bis-SorbPC)-coated particles showed high fluorescence intensities after exposure to FM1-43, indicating that the polymerized bilayers were stable to the shear forces required to pack capillary columns. Additionally, the capillaries packed with DOPC-coated particles exhibited diminished fluorescence compared to the poly(bis-SorbPC)-coated particles. This suggests that the unstabilized lipid bilayers were removed by the shear forces generated during packing. Additional particle images (FIG. 20) illustrate that the poly(bis-SorbPC) coatings were stable when simultaneously exposed to high pressure (2900 psi) and organic solvents (25-40% ACN). The combined chemical, temporal, and physical stability of poly(bis-SorbPC) coatings illustrates that columns prepared with this stationary phase should have higher stability than ILC columns, while maintaining both leaflets of a lipid bilayer.

The imaging and flow cytometry studies presented above show that poly(bis-SorbPC) membranes deposited on silica particles exhibit enhanced chemical and temporal stability compared to non-polymerized lipid bilayers (DOPC). However, aggregates of particles were observed after UV polymerization and these were exacerbated following membrane destabilizing conditions, e.g. surfactant or organic rinse (FIG. 15). Interestingly, when bis-SorbPC was polymerized using either redox initiation method, no aggregates were observed (FIG. 15). In general, redox polymerization is known to yield a greater degree of crosslinking between the two leaflets of the bilayer and a longer polymer network (degree of polymerization, $X_n$=40-600) compared to UV initiation ($X_n$=3-10). Thus, UV polymerized particles are more likely to be structurally altered when exposed to surfactant or organic solvent. Partial loss of lipids from the outer leaflet of the bilayer may result in exposure of the hydrophobic tails of the remaining monolayer, leading to aggregation of the UV polymerized particles to minimize hydrophobic interactions with the aqueous environment (FIG. 21 provides a schematic representation).

Figure 18A:
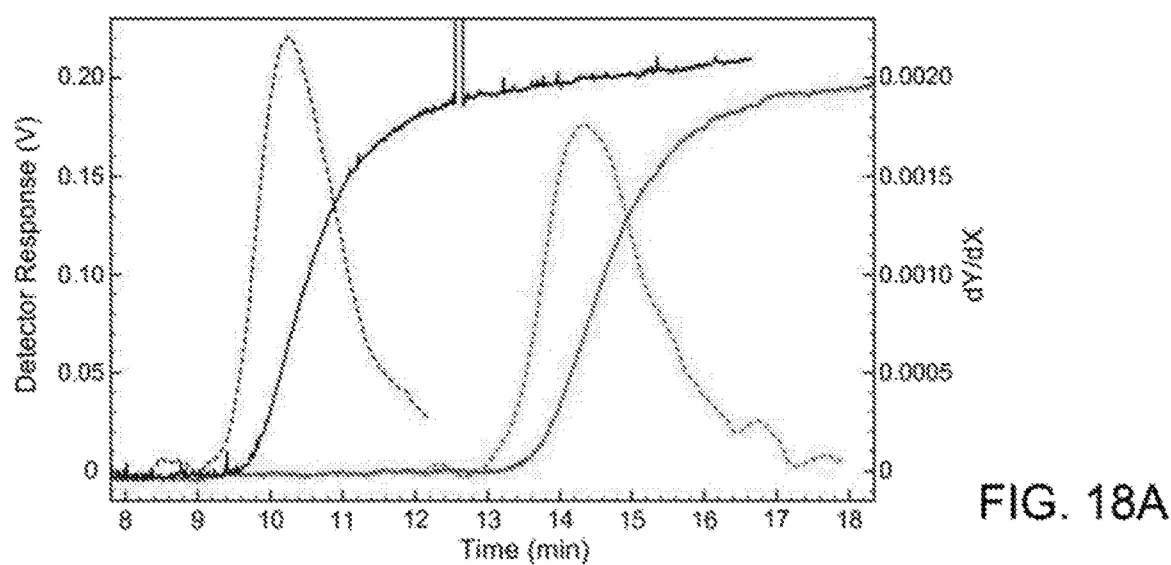
FIGS. 18A-18C show chromatographic frontal analyses of lipophilic small molecules. Frontal analyses of acetylsalicylic acid (A), benzoic acid (B), and salicylic acid (C) show increased retention on poly (bis-SorbPC) stationary phases (red) when compared to bare silica stationary phases (black). Retention times were determined from first derivative plots (dashed lines).
Figure 18B:
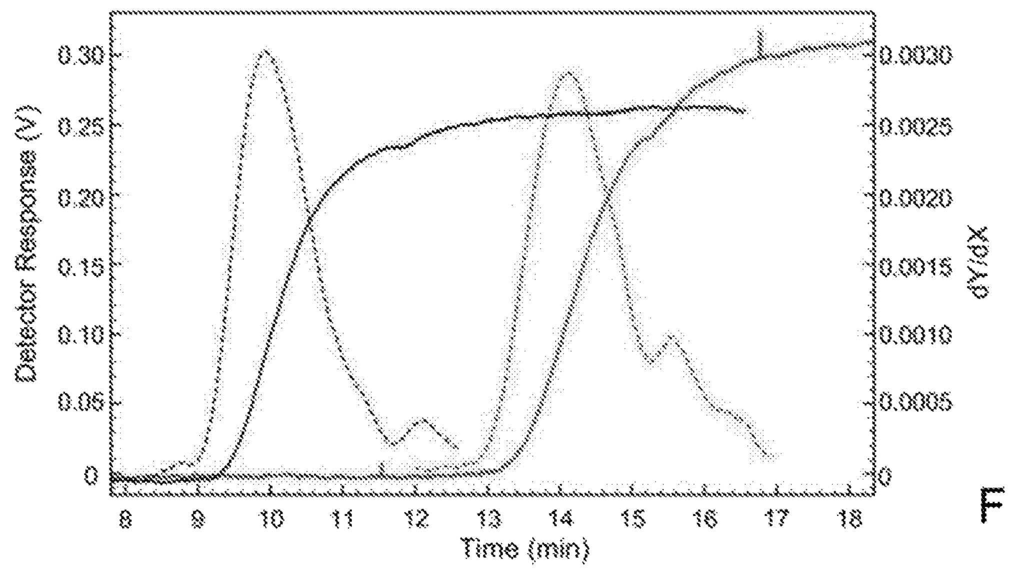
Figure 18C:
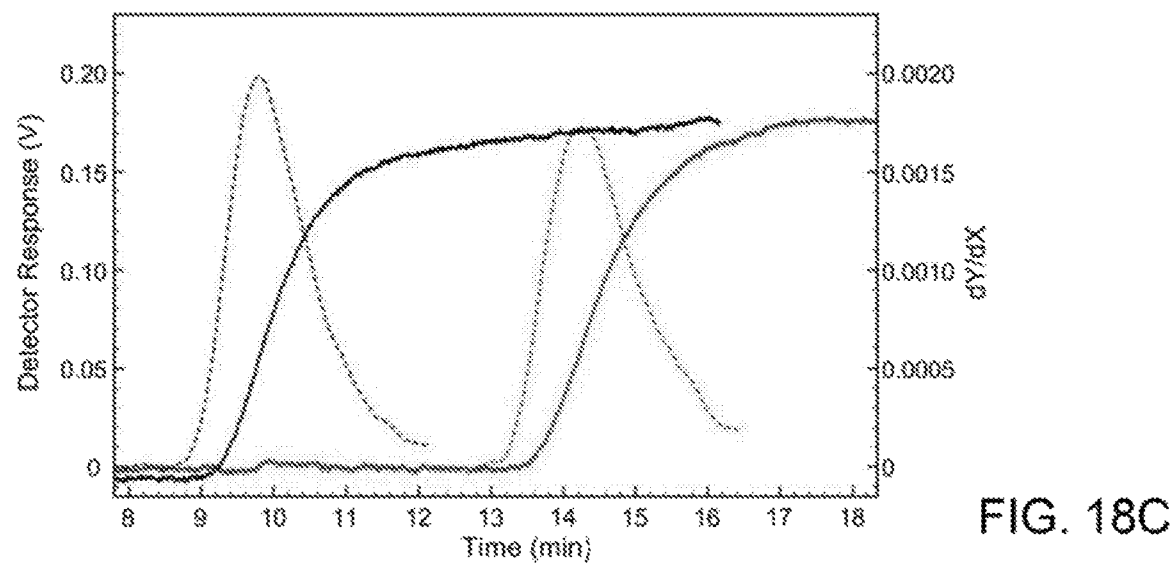

To demonstrate the efficacy of poly(bis-SorbPC)-coated silica following packing into capillary columns, frontal analyses of three lipophilic small molecules that are known to cross cell membranes were performed using capillary LC. FIG. 18 shows representative frontal chromatograms of acetylsalicylic (A), benzoic (B), and salicylic (C) acids using capillary columns packed with bare silica (black) or poly (bis-SorbPC)-coated silica (red) particles. Retention times were defined as the maximum of the distribution in the first derivative plot (dashed lines). In each case, a clear increase in retention was observed when analytes were introduced to the poly(bis-SorbPC) stationary phase compared to silica stationary phase particles, suggesting lipophilic retention. Table 14 provides mean retention times and reproducibility for the lipophilic analytes on silica and poly(bis-SorbPC)-coated stationary phases. Retention times increased with statistical significance ($P<0.0001$) on the poly(bis-SorbPC) stationary phase relative to bare silica for each analyte.

Table 14 shows frontal chromatography retention analyses.

| | Silica | | poly(bis-SorbPC) | |
|---|---|---|---|---|
| Analyte | Retention time (min) | RSD (%) | Retention time (min) | RSD (%) |
| Acetylsalicylic acid | 10.1 ± 0.2 | 1.7 | 14.6 ± 0.6 | 3.8 |
| Benzoic acid | 9.6 ± 0.2 | 1.9 | 14.1 ± 0.1 | 0.9 |
| Salicylic acid | 9.7 ± 0.1 | 1.0 | 14.3 ± 0.1 | 0.4 |

Importantly, column performance was highly reproducible. Frontal chromatograms yielded retention time relative standard deviations less than 4% for acetylsalicylic acid and less than 1% for benzoic acid and salicylic acid (n 4) over the course of 1 week, values that are on par with silica particles lacking a coating. This is particularly impressive when considering the operating pressure for each run exceeded 2700 psi. Thus not only do poly(bis-SorbPC) coated particles withstand slurry packing but also high pressures associated with the separation which would delaminate unpolymerized lipid coatings and lipid architectures. These key results provide the foundation for a new range of high pressure and thus higher throughput evaluation of mixtures for lipid membrane interactions.

Radical polymerization of bis-SorbPC and other lipids with functional groups can be achieved with redox mixtures. One of the most commonly used is the 1:1 mixture of potassium persulfate ($K_2S_2O_8$, oxidant) and sodium hydrogen sulfite ($NaHSO_3$, reductant). However, initiation and progression of the polymerization with this redox couple proceed only under acidic conditions (pH of the aqueous redox mixture is 1-2 depending on the concentration). This could be problematic for proteins incorporated into lipid vesicles. Unless milder conditions are used in the polymerization of lipids, transmembrane proteins often get denatured. For example, activity of Rhodopsin incorporated into bis-SorbPC vesicles, measured spectroscopically at 500 nm, diminished or disappeared after redox polymerization with the above redox couple. Therefore, other polymerization methods that proceed under neutral pH were investigated.

Both direct UV-induced and photo-initiated radical polymerizations were tried as alternatives. Photo-initiated radical polymerization was performed using DMABN and a UG-1 band pass filter (ca. 300-400 nm). Both UV and radical polymerization methods were applied to Rhodopsin incorporated bis-SorbPC vesicles in pH 5.5 MES buffer. Bis-SorbPC polymerization occurs in both conditions, but Rhodopsin activity also disappears concurrently (FIG. 23).

Figure 24:
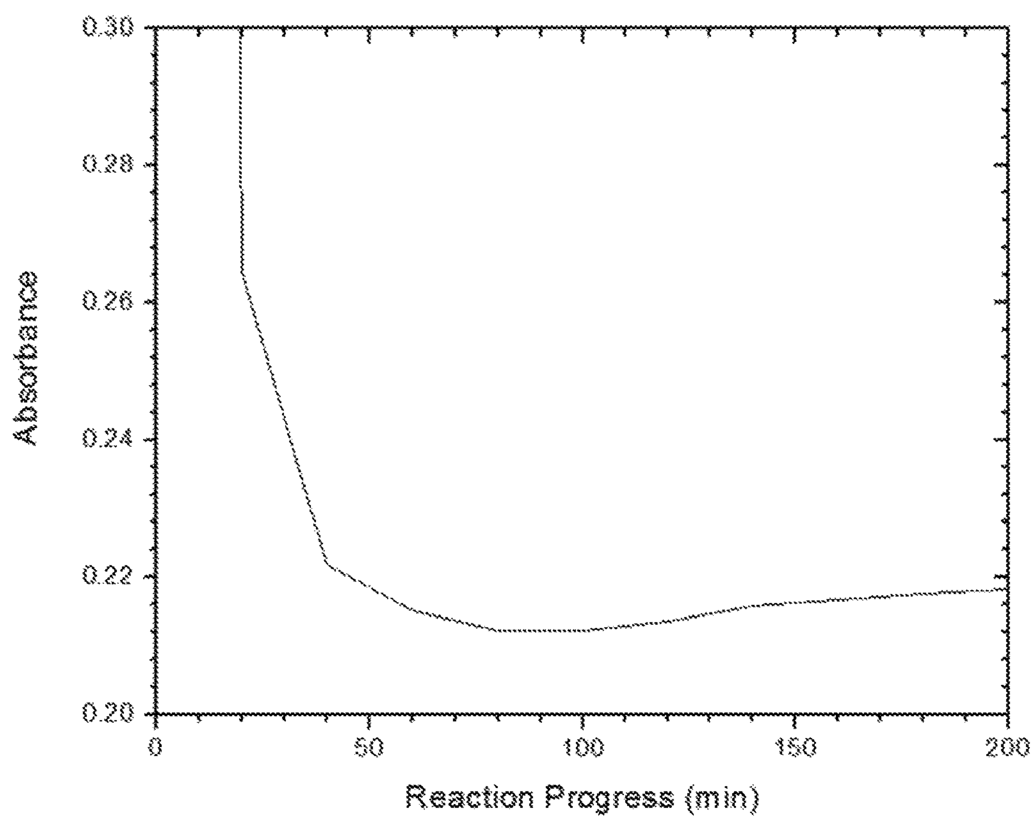
FIG. 24 shows a plot of absorbance vs. reaction progress (min) for redox polymerization of bis-SorbPC vesicles using AP and $NaHSO_3$ in pH 7 phosphate buffer, monitored at 258 nm at room temperature. The initiators to lipid ratio is 348:348:1. The initial absorbance (before polymerization is initiated) is 1.6. The percent conversion after 20, 60, 1440 min is 84, 86, and 89, respectively.
Figure 25:
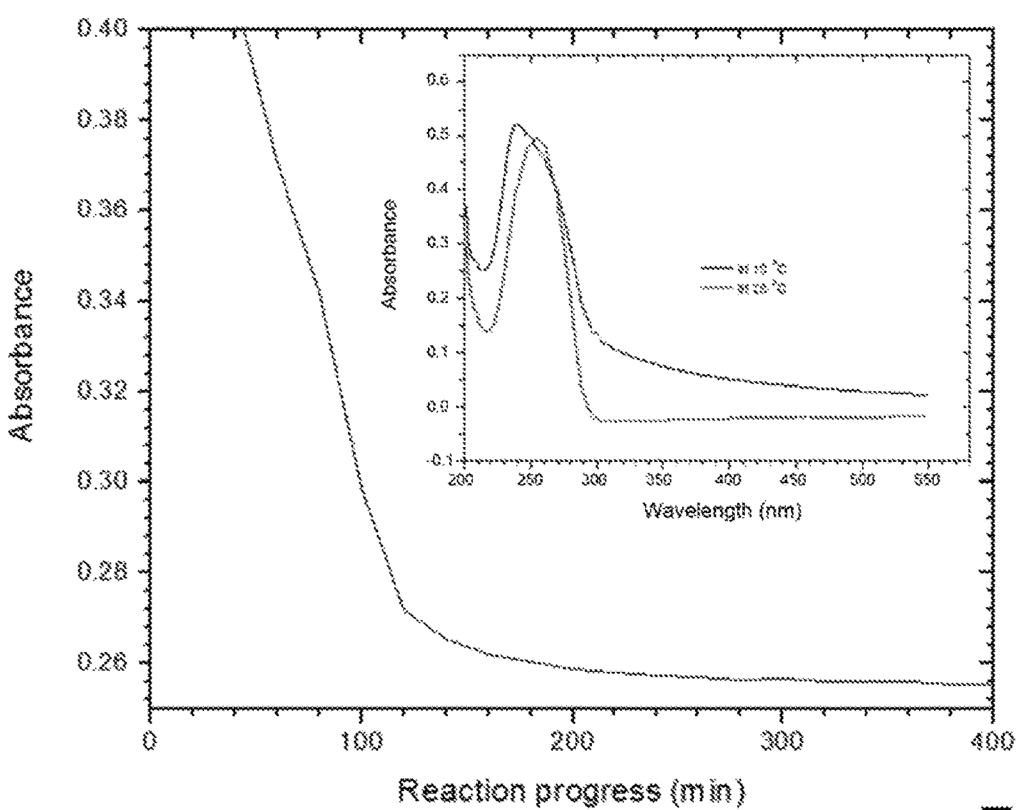
FIG. 25 shows an enlarged plot of absorbance vs. reaction time (min) for redox polymerization of bis-SorbPC using AP and $NaHSO_3$ in pH 5.5 MES buffer, monitored at 258 nm at 10° C. Other conditions are similar to FIG. 24. Insert shows the bis-SorbPC absorbance peak shape at 10° C., and after warming the reaction mixture to 28° C. These measurements were taken before adding the redox mixture.

Another alternative is to use another redox mixture that generates radicals under different pH conditions. One of those mixtures is AP and $NaHSO_3$. FIG. 24 shows that AP and $NaHSO_3$ mixture can polymerize bis-SorbPC vesicles at pH 7 phosphate buffer at room temperature. It also shows that the polymerization is largely complete in 1 hour. This experiment was performed using a large ratio of initiators to lipid (348:348:1). However, this ratio is similar to what is used in a typical acrylamide gel polymerization.

The photoactivity of Rhodopsin embedded in vesicles is usually measured in a pH 5.5 MES buffer at 10° C. Therefore, the polymerization of bis-SorbPC in these conditions using the initiators and the lipid ratio mentioned earlier is shown in FIG. 25. The progress of the polymerization is similar to that of FIG. 24. However, it is difficult to calculate the actual percent conversion of the bis-SorbPC monomer because the absorbance peak max is at 242 nm at 10° C. (and changes with the temp), rather than at 258 nm. Therefore, it is presumed that the conversion rates (initiators to lipid ratio 348:348:1) at room temperature for phosphate buffer are valid with the MES buffer.

Figure 26:
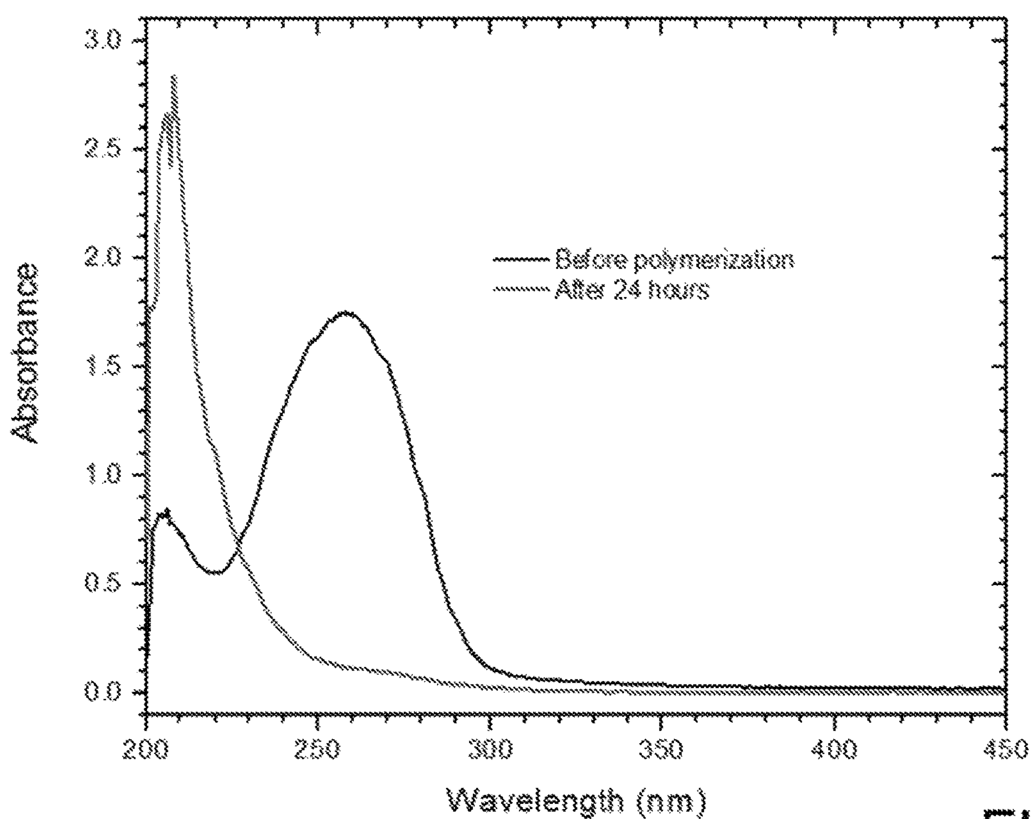
FIG. 26 shows absorbance spectra of bis-SorbPC vesicles prepared in pH 5.5 MES buffer and polymerized with the AP and $NaHSO_3$ redox mixture. The polymerization was done at 10° C., using a 100:100:1 AP:$NaHSO_3$:lipid ratio. The initial spectrum was taken before adding the redox mixture.

The effect of redox mixture on the spectroscopic properties of the vesicles prepared with MES buffer solution is shown in FIG. 26. It is possible to achieve high monomer to polymer conversion using less than the 348:348:1 initiators to lipid ratio that was used in FIG. 24. Studies based on different initiator concentrations are summarized into FIG. 27. It shows that 90% conversion can be achieved for bis-SorbPC vesicles prepared in pH 5.5 MES buffer at 10° C. using a 100:100:1 initiators to lipid ratio. Although the studies in the FIG. 27 were completed in a 24 hr period, further studies with a 100:100:1 initiators to lipid ratio suggests that the radical polymerization is essentially over after 60 min (FIG. 28). In addition, these data show that the assumption made for MES buffers about the conversion rates based on phosphate buffers is valid.

Figure 27:
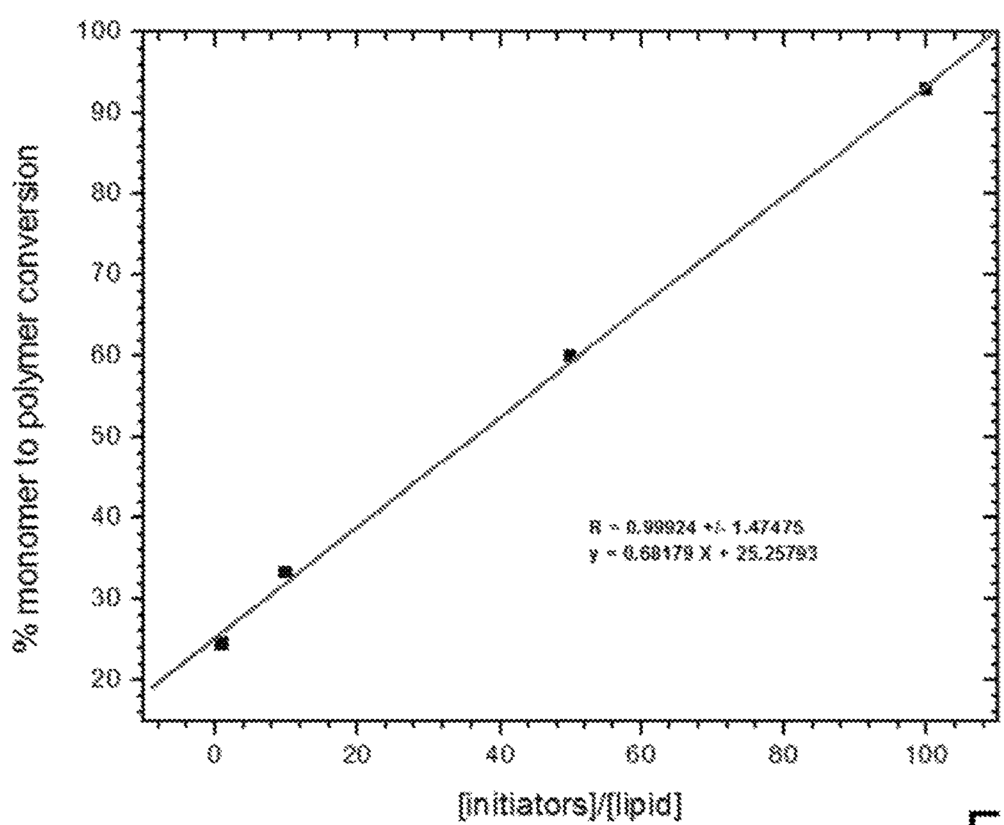
FIG. 27 shows a plot of percent monomer to polymer conversion vs. different initiator concentrations for redox polymerization of bis-SorbPC using AP and $NaHSO_3$ in pH 5.5 MES buffer, monitored at 258 nm at 10° C. The oxidant to reductant ratio was 1:1 in all cases. The polymerization was done at 10° C. for minimum of 24 hrs. The initial spectrum was taken before adding the redox mixture. The initial and the final spectral measurements were taken at room temperature.
Figure 28:
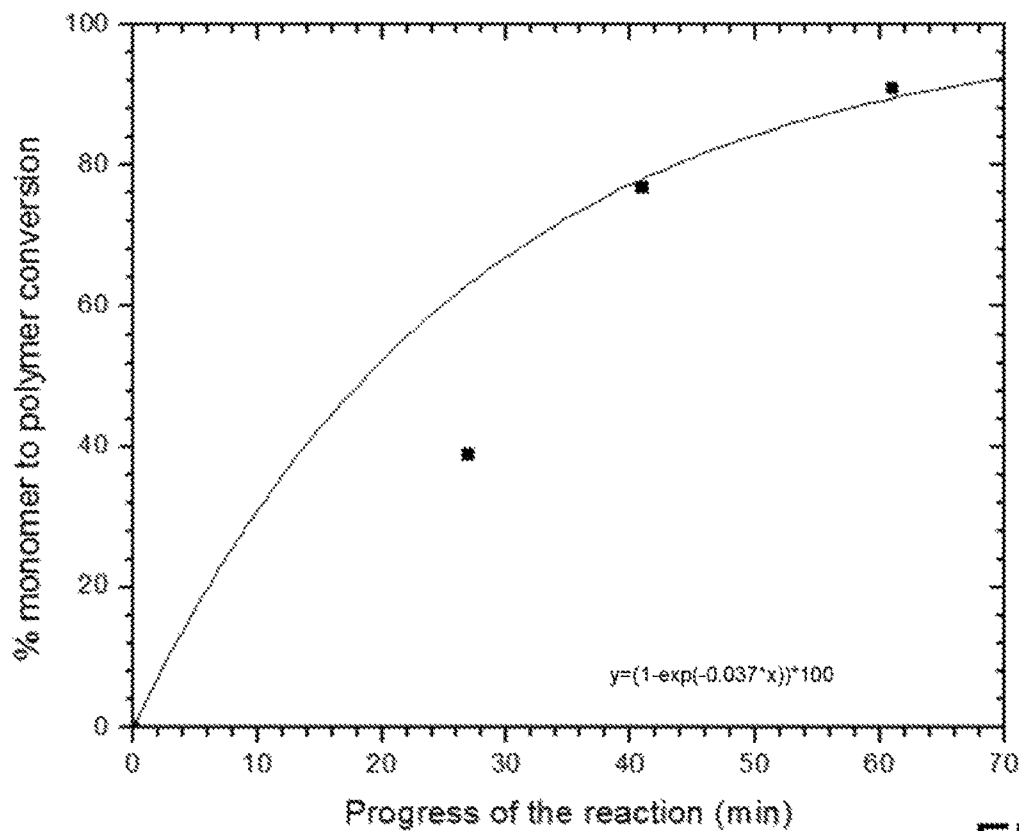
FIG. 28 shows a plot of percent monomer to polymer conversion vs. reaction time (min) for redox polymerization of bis-SorbPC using AP and $NaHSO_3$ in pH 5.5 MES buffer, monitored at 258 nm. The polymerization was done at 10° C. with 1:100:100 lipid:AP:$NaHSO_3$ molar ratios. Aliquots from the reaction mixture were taken at intervals and the absorbance was measured after dilution in methanol (MeOH) at room temperature. The initial spectrum was taken before adding the redox mixture.

Data from FIG. 27 and FIG. 28 suggest that the radical generation happens only for a short period of time, during which radicals are generated and reacted quickly, which is useful for maintaining the activity of incorporated proteins. In comparison, the $K_2S_2O_8$ and $NaHSO_3$ mixture can continually polymerize bis-SorbPC for about ca. 24 hr or more under certain conditions. In another study, small aliquots of AP and $NaHSO_3$ mixture were added to a bis-SorbPC vesicle solution at intervals and 90+% polymerization was achieved. If the sample is sensitive to high salt concentrations, this method gives another way to achieve polymerization to a high degree. In addition, it is possible to remove the salts generated by the redox mixture by dialysis, thereby keeping the salt concentration low in the reaction mixture. Without wishing to limit the present invention to any theory or mechanism, the AP and $NaHSO_3$ mixture apparently follows a different mechanism than the $K_2S_2O_8$ and $NaHSO_3$ mixture to generate radicals.

A highly crosslinked polymer results when $K_2S_2O_8$ and $NaHSO_3$ are used as the redox couple to polymerize bis-SorbPC ($X_n$=40-600). The initiation reactions between $S_2O_8^{2-}$ and $HSO_3^-$ are shown below (Scheme 1).

$$S_2O_8^{2-}+HSO_3^- \rightarrow HSO_3{*}SO_4^{*-}+SO_4^{2-}$$

$$SO_4^{*-}+H_2O \rightarrow HSO_4^-+OH^{*-} \quad (1)$$

$HSO_4^-$ ($pK_a$ 1.9) is produced as a byproduct of initiation, resulting in an acidic solution. When bis-SorbPC lipids undergo redox-initiated polymerization, the decrease in pH does not affect the lipid structure or the resulting polymer; however, if membrane proteins are to be incorporated into bis-SorbPC membranes before redox polymerization, the resulting decrease in pH may alter the native protein conformation. Thus, the inventors sought to identify conditions that would be more compatible with membrane protein-functionalized matrices.

When $(NH_4)_2S_2O_8$ was substituted for $K_2S_2O_8$ in the redox reaction, a solution with approximately neutral pH resulted. The mixture could be buffered to pH 7.4 and the solution still maintained a high degree of monomer to polymer conversion, as opposed to the previous redox couple, as indicated by the stability and lack of aggregation (FIG. 15 and FIG. 16). Though the mechanistic differences between the redox reactions were not studied, redox polymerization using $(NH_4)_2S_2O_8$ should provide solution conditions that are more compatible for incorporation of membrane proteins; thus, redox polymerizations using $(NH_4)_2S_2O_8$ and $NaHSO_3$ were employed for preparing poly(bis-SorbP) coatings for frontal chromatographic analyses.

Figure 29:
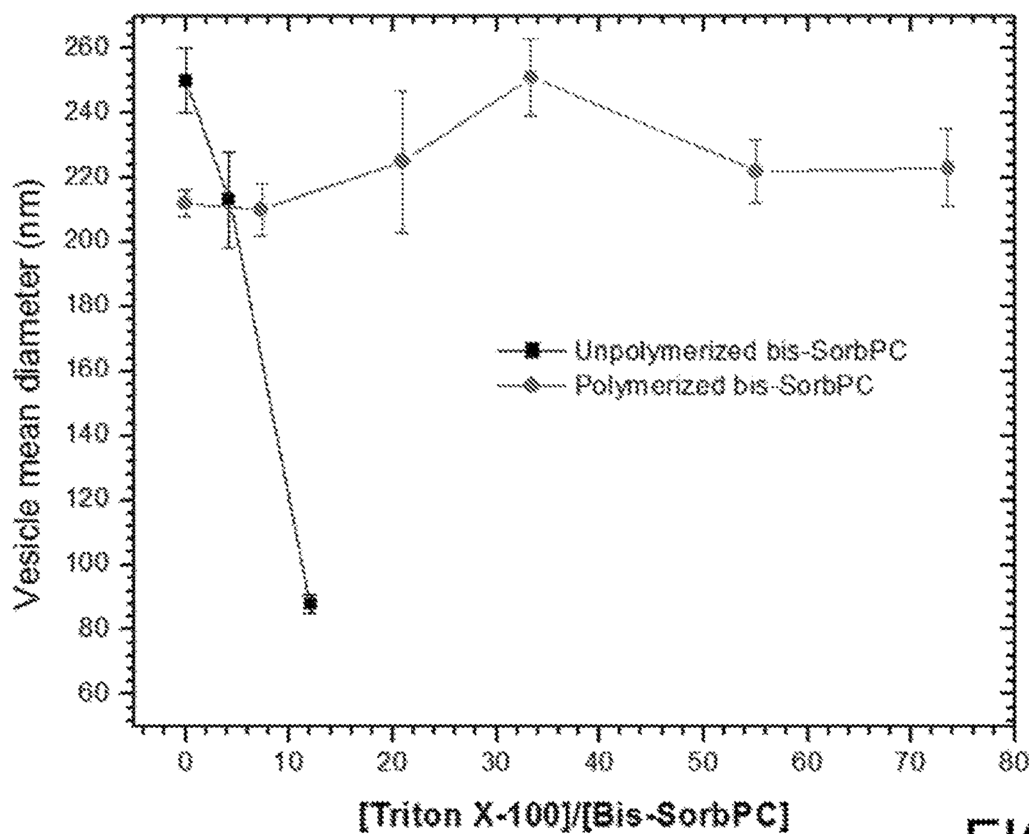
FIG. 29 shows dynamic light scattering (DLS) measurements of mean diameters of unpolymerized and redox polymerized bis-SorbPC vesicles in the presence of Triton X-100. The polymerization conditions were AP and $NaHSO_3$ in pH 5.5 MES buffer at 10° C. with a 1:100:100 lipid:AP:$NaHSO_3$ molar ratio for 105 min. Vesicles were prepared by extruding through two stacked Nuclepore polycarbonate filters (600,400, and 200 nm pore sizes 3×, 3×, and 4× sequentially) for a total of 10 times.
Figure 30:
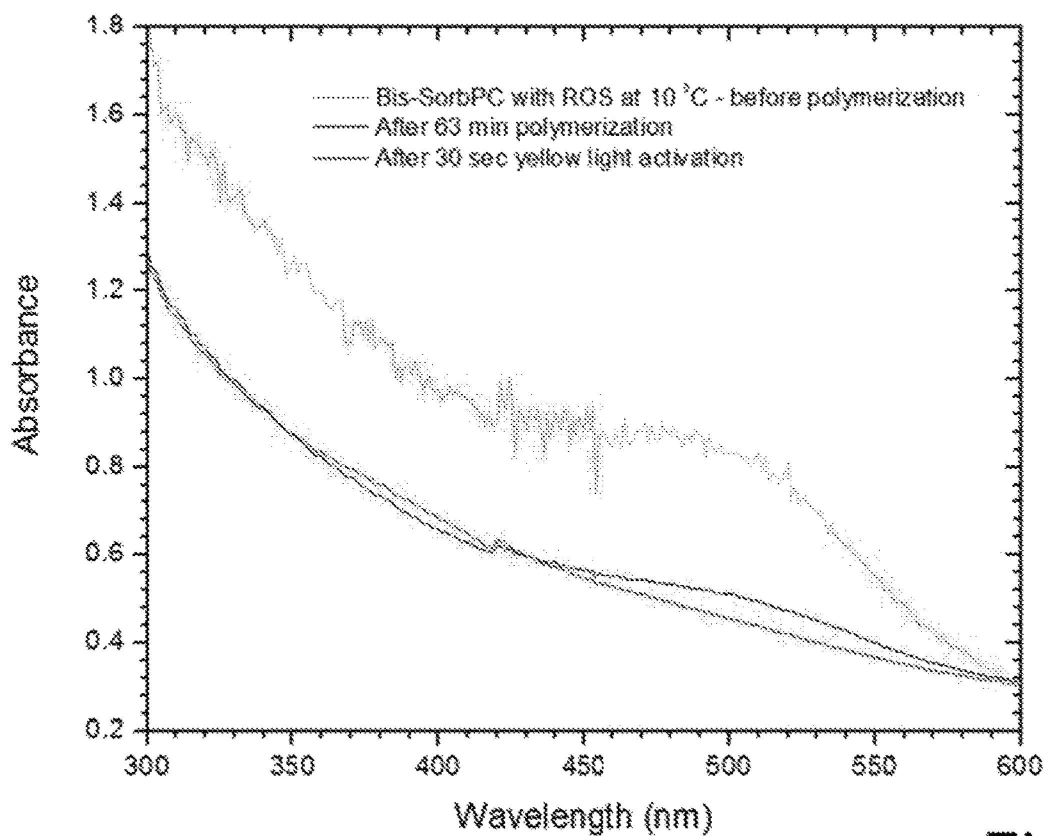
FIG. 30 shows absorbance vs. wavelength (nm) of bis-SorbPC vesicles with incorporated ROS membranes in pH 5.5 MES buffer before and after polymerization with AP and $NaHSO_3$. The polymerization was done at 10° C., with a 100:100:1 AP:$NaHSO_3$:lipid ratio for 63 min. The spectra are normalized at 600 nm for display purposes. The spectral change that occurs after yellow light activation indicates that the Rhodopsin is active in the polymerized vesicles.

Stability tests of polymerized vesicles often reveal the type of polymer formed by the polymerization method, such as whether the polymers are linear or cross-linked. One commonly used stability test is Triton X-100 insertion. FIG. 29 shows the stability of the polymerized and unpolymerized bis-SorbPC vesicles in the presence of Triton X-100. The data suggest that polymerized vesicles show the stability of cross-linked bis-SorbPC polymers while unpolymerized vesicles quickly disintegrate with increasing Triton X-100 concentration. Formation of cross-linked polymers is common in radical polymerization methods such as the one used in the present invention. However, one would expect that the rapid generation of radicals in short period of time, as suggested above, would generate multiple nuclei for the polymerization that would produce shorter polymer chains. The remarkable stabilization observed in this invention suggests that the cross-linking occurs and it may possibly be ascribed to the terminal location of the Sorbyl functional groups in bis-SorbPC, and the covalent reaction of oligomers across leaflets. In some embodiments, different sorbyl functionalized lipids, such as bis-DenPC, may be polymerized and tested.

Figure 31:
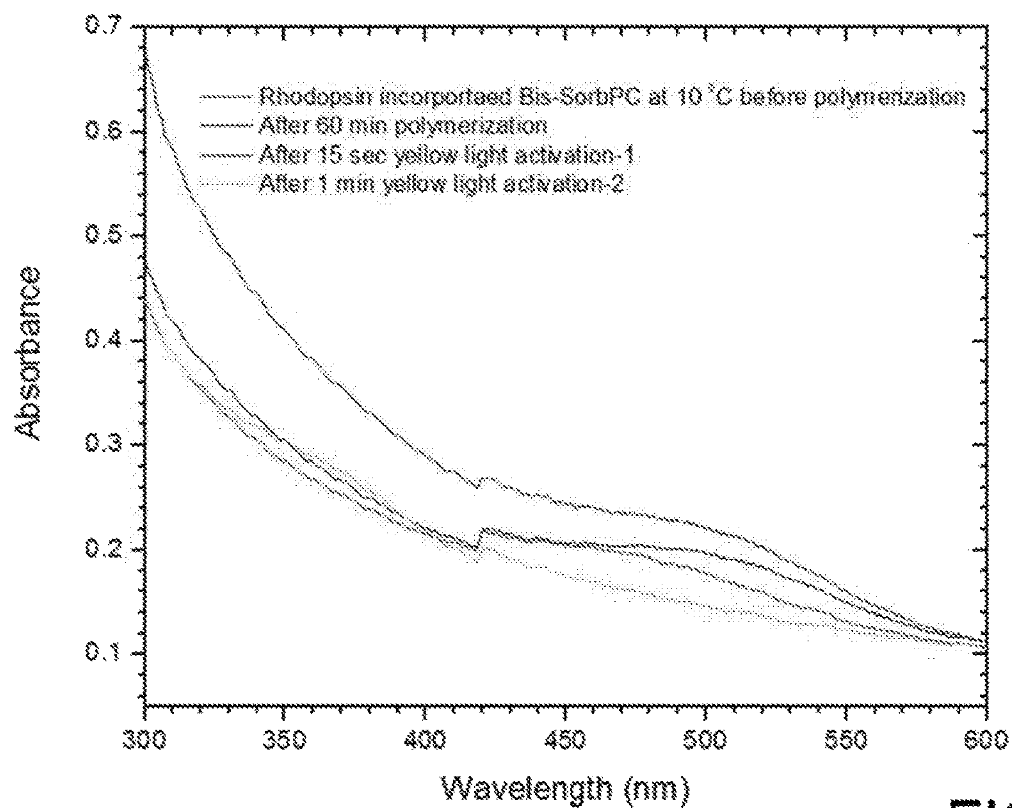
FIG. 31 shows absorbance vs. wavelength (nm) of Rhodopsin incorporated into bis-SorbPC vesicles in pH 5.5 MES buffer before and after polymerization with AP and $NaHSO_3$. The polymerization was done at 10° C., with a 100:100:1 AP:$NaHSO_3$:lipid ratio for 60 min. The spectra are normalized at 600 nm for display purposes. The spectral change that occurs after yellow light activation indicates that the Rhodopsin is active in the polymerized vesicles.

The redox mixture was applied to Rhodopsin embedded bis-SorbPC vesicles to check on whether the initiator mixture is mild enough to maintain Rhodopsin activity and also to achieve a high degree of lipid polymerization. At first, crude samples with Rhodopsin (ROS membranes) were incorporated into bis-SorbPC vesicles in MES buffer and the polymerization was performed. The results are summarized in FIG. 30. The partial retention of the peak at ca. 500 nm after the polymerization shows that Rhodopsin maintains some activity. The retention of activity was further verified by illuminating the sample with yellow light which photoactivates Rhodopsin. The polymerization method was applied to purified Rhodopsin incorporated into bis-SorbPC vesicles. The results are shown in FIG. 31. The results confirmed that Rhodopsin in robust crude samples and also purified Rhodopsin retain at least partial activity during the polymerization of bis-SorbPC with the AP and $NaHSO_3$ redox mixture. In some embodiments, the radical polymerization method may be mild enough for transmembrane proteins. In some embodiments, other polymerizable lipids, such as bis-DenPC, may be polymerized with the activity of rhodopsin retained. Another approach is to add aliquots of the initiator mixture at intervals, thereby limiting exposure of the protein to high radical and salt concentrations to enhance the retention of protein activity.

Conclusions

Poly(bis-SorbPC) coatings on silica particles exhibited increased chemical, temporal, and physical stability compared to unpolymerized phospholipid bilayer coatings (DOPC). Redox-initiated polymerization yielded bilayers with greater stability than UV poly(bis-SorbPC) coatings, which aggregated after exposure to chemical insults. Additionally, chromatographic frontal analyses of small molecule analytes showed reproducible lipophilic retention on poly (bis-SorbPC)-coated particles polymerized with AP/$NaHSO_3$, indicating that the highly stabilized lipid membrane environment of the poly(lipid) stationary phase presents an excellent platform for further development of biomimetic stationary phases. Thus, poly(bis-SorbPC) stationary phases show enhanced stability and high reproducibility compared to ILCs. The presence of a full phospholipid bilayer may also make poly(lipid) stationary phases more compatible with future incorporation of membrane proteins, presenting an excellent opportunity for new affinity chromatography approaches to study physiological and pharmaceutical modulators of phospholipid membranes and/or membrane proteins.

The AP and $NaHSO_3$ redox mixture polymerizes bis-SorbPC vesicles at slightly acidic or near neutral pH solutions at similar conversion rates to the $K_2S_2O_8$ and $NaHSO_3$ redox mixture. Polymerization at near neutral pH is a critical feature when incorporating transmembrane proteins into bilayers composed of polymerizable lipids and stabilizing these supramolecular assemblies by cross-linking polymerization. The experimental evidence suggests that the AP and $NaHSO_3$ redox mixture has all these desirable properties. In addition, the AP and $NaHSO_3$ redox mixture is mild enough to maintain the photoactivity of the model transmembrane protein, Rhodopsin, during the polymerization.

Section 2B

Referring now to FIGS. 32-44, alternative embodiments of the present invention features polymerization of lipid monomers to form a planar supported lipid bilayer (PSLB) in order to provide the stability needed for MALDI-TOF MS analysis of proteins captured by receptors embedded in the membrane. Matrix-assisted laser desorption/ionization-time of flight mass spectrometry (MALDI-TOF MS) coupled with affinity capture is a well-established method to extract biological analytes from complex samples followed by label-free detection and identification. Many bioanalytes of interest bind to membrane-associated receptors, however, the matrices and high vacuum conditions inherent to MALDI-TOF MS make it largely incompatible with the use of artificial lipid membranes with incorporated receptors as platforms for detection of captured proteins and peptides. Cross-linking polymerization of a PSLB provides the stability needed for MALDI-TOF MS analysis of proteins captured by receptors embedded in the membrane. PSLBs composed of poly(bis-SorbPC) and doped with the ganglioside receptors GM1 and GD1a were used for affinity capture of the B-subunits of cholera toxin, heat-labile enterotoxin, and pertussis toxin. The three toxins were captured simultaneously, then detected and identified by MS based on differences in their molecular weights. Poly(bis-SorbPC) PSLBs are inherently resistant to nonspecific protein adsorption, which allowed selective toxin detection to be achieved in complex matrices (bovine serum and shrimp extract). Using GM1-cholera toxin B as a model receptor-ligand pair, the minimal detectable concentration of toxin was estimated to be 4 nM. On-plate trypsin digestion of bound cholera toxin B followed by MS/MS analysis of digested peptides was performed successfully, demonstrating the feasibility of using the PSLB-based affinity capture platform for identification of unknown, membrane-associated proteins. Overall, the combination of a poly(lipid) affinity capture platform with MALDI-TOF MS detection is a viable approach for capture and proteomic characterization of membrane-associated proteins in a label-free manner.

Affinity capture coupled with matrix-assisted laser desorption/ionization-time of flight mass spectrometry (MALDI-TOF MS) is a label-free method to detect and identify a peptide or protein ligand that binds to a receptor immobilized on a solid support. In this approach, water-soluble receptors (typically antibodies) are used to extract the ligand from a complex mixture. The affinity capture surface is prepared by covalently immobilizing the receptor on a substrate surface that is compatible with MALDI-TOF MS analysis (the "direct" method), or on a solid support from which the captured analytes are subsequently desorbed and deposited on a standard MALDI plate (the "indirect" method).

In principle, affinity capture coupled with MALDI-TOF MS could be a powerful approach for characterizing ligands that target receptors embedded in artificial phospholipid membranes, which are widely used as models of natural cell membranes and recognition processes that occur at these membranes. A seminal paper by Marin et al. demonstrated a strategy for MALDI analysis of a ligand bound to a receptor incorporated into an artificial membrane. Bovine rhodopsin (Rho) was reconstituted into His-tagged lipid nanodiscs that were captured onto a self-assembled monolayer (SAM) on Au. Transducin was incubated with the Rho/nanodisc/SAM assembly and then subsequently detected using MALDI-TOF MS. However, background peaks for Rho, lipids, and the nanodisc scaffold protein were also present in the mass spectrum, which illustrates a major drawback of the nanodisc strategy—matrix deposition and laser ionization causes dissociation of the entire assembly, producing a complex background spectrum. Ideally, the assembly would be less structurally complex, and matrix deposition/laser ionization would cause only the ligand to dissociate from the receptor, leaving the rest of the molecular assembly intact.

A structurally simpler alternative is a PSLB that is deposited directly on a solid substrate. However, conventional PSLBs are typically composed of fluid-phase glycerophospholipids. The relatively weak, noncovalent interactions in the bilayer and between it and the underlying planar substrate are insufficient to maintain the PSLB structure upon exposure to air, organic solvents, and high vacuum; thus conventional PSLBs are not stable to the analysis conditions inherent to affinity capture coupled with direct MALDI-TOF MS.

PSLB stability can be greatly enhanced by polymerization of synthetic lipids bearing cross-linkable moieties, such as bis-Sorbyl phosphatidylcholine (bis-SorbPC), which suggests that a polymerized PSLB could be a functional platform for MALDI-TOF MS detection of ligands captured by incorporated receptors.

Bacterial toxins that target membrane-bound gangliosides are used to assess the suitability of polymerized PSLBs as an affinity capture surface for MALDI-TOF MS detection. Gangliosides are major membrane receptors for toxins such as cholera toxin, heat-labile enterotoxin and pertussis toxin. Poly(bis-SorbPC) PSLBs were doped with GM1, a monosialoganglioside that binds to the B-subunit of cholera toxin and heat-labile enterotoxin, and GD1a, a disialoganglioside that is a receptor for the B-subunit of pertussis toxin. The three individual ganglioside-toxin B pairs were characterized first, followed by simultaneous detection and identification of all three toxins. Cholera toxin B (CTB) and GM1 were used to assess the minimal detectable toxin concentration, as well as detectability in a complex matrix. The results show that a poly(bis-SorbPC) PSLB is stable to MALDI-TOF MS analysis conditions; the mass spectrum of the dissociated toxin is largely free of background peaks due to other components in the molecular assembly. Finally, the feasibility of on-plate trypsin digestion of CTB bound to GM1 in a PSLB, followed by MS/MS analysis of digested peptides, also was demonstrated. Overall, these results show that combining a poly(lipid) affinity capture platform with MALDI-TOF MS detection is a viable approach for identification and proteomic characterization of membrane-associated proteins in a label-free manner.

EXPERIMENTAL

GM1 and 1,2-diphytanoyl-sn-glycero-3-phosphocholine (DPhPC) were purchased from Avanti Polar Lipids (Alabaster, Ala.). GD1a was purchased from Sigma-Aldrich (St. Louis, Mo.). 1,2-bis[10-(2',4'-hexadienoloxy)decanoyl]-sn-glycero-3-phosphocholine (bis-SorbPC) was synthesized and purified by preparatory scale high performance liquid chromatography as described in Electronic Supplementary Material (SM). For safety considerations, only the binding domains of toxins were used. CTB and heat-labile enterotoxin B (LTB) were obtained from Sigma-Aldrich. Pertussis toxin B oligomer (PTB) was purchased from List Biological Laboratories, Inc (Campbell, Calif.). Water from a Barnstead Nanopure system with a minimum resistivity of 18 MΩ·cm was used. Stock toxin solutions were made by dissolving each toxin in nanopure water at 0.5 mg/mL. Phosphate buffered saline, pH 7.4 (PBS) contained the following components: 140 mM sodium chloride, 3 mM potassium chloride, 10 mM dibasic sodium phosphate, 2 mM monobasic potassium phosphate, 0.2 mM sodium azide. Silicon wafers were obtained from Wacker Chemie AG. Fetal bovine serum (FBS) was purchased from Invitrogen (Grand Island, N.Y.). Sinapinic acid was purchased from Fluka Analytical (St. Louis, Mo.) and alpha-cyano-4-hydroxycinnamic acid (HCCA) was provided by Bruker Daltonics Inc. (Auburn, Calif.). Peptide calibration standard II, containing Angiotensin II, Angiotensin I, Substance P, Bombesin, ACTH clip 1-17, ACTH clip 18-39, Somatostatin 28, Bradykinin Fragment 1-7, and Renin Substrate Tetradecapeptide porcine, was supplied by Bruker Daltonics Inc. Cytochrome c and myoglobin were purchased from Sigma-Aldrich. Trypsin Gold, mass spectrometry grade, was purchased from Promega (Madison, Wis.).

Preparation of Small Unilamellar Vesicles (SUVs) with Incorporated GM1 and GD1a.

Stock solutions of bis-SorbPC were prepared in pure chloroform. GM1 was dissolved in methanol and GD1a in 2/1 chloroform/methanol (v/v). GM1 and GD1a were mixed with bis-SorbPC at molar ratios of 1/99 and 1/4, respectively (expressed below as 1 mol % and 20 mol %, respectively). Organic solvents were evaporated from the lipid mixtures under a stream of argon, followed by vacuum drying for at least four hours. The lipids were then rehydrated with PBS to a concentration of 0.5 mg/mL, vortexed, and then sonicated in a Branson Sonicator with a cup horn at 35° C. until the solution was visibly clear (usually 30 min).

Preparation of Polymerized PSLBs.

Silicon wafers (cut to 0.8 cm×0.8 cm) were cleaned in piranha solution (7/3 concentrated $H_2SO_4/H_2O_2$) for 30 minutes and rinsed thoroughly in nanopure water. The silicon wafers were dried with a stream of nitrogen and incubated in 200 μL SUV solutions at 35° C. on a hot plate for at least 15 minutes to form PSLBs. Unfused SUVs were rinsed away with copious PBS buffer (at least 10 mL) without exposing the PSLB to air. A low-pressure mercury pen lamp with a rated intensity of 4500 $\mu W/cm^2$ at 254 nm was directed through a bandpass filter (325 nm, 140 nm FWHM; U330, Edmund Optics) for 60 minutes to polymerize bis-SorbPC. The distance between the lamp and the PSLB was 7.6 cm.

Mass Spectrometric Detection of Toxins.

The toxin solution (0.5 mL of 0.24 μM CTB, 0.24 μM LTB, and/or 1 μM PTB) was incubated with GM1- and/or GD1a-incorporated PSLBs on 0.8 cm×0.8 cm silicon wafers for 1 hour. PSLBs were then rinsed thoroughly with water and dried under a nitrogen stream. Nonspecific binding was assessed by incubating toxins with PSLBs that lacked gangliosides, followed by rinsing and drying. The MS mass calibration standard was prepared by mixing 0.5 μL of myoglobin solution (3.8 mg in 500 μL), 1.0 μL of cytochrome c solution (1.2 mg in 500 μL) and 8.5 μL of saturated sinapinic acid (SA) in 70/30/1 $H_2O$/acetonitrile/trifluoroacetic acid. The dried silicon wafers were mounted onto a MALDI plate (a microtiter plate (MTP) adapter for Prespotted AnchorChip Targets (Bruker)) using double-sided tape. The calibration standard (1 μL) was spotted on each wafer for external calibration. Three or four different spots of 1 μL SA solution were added to the remaining surface of each wafer and the solvent was allowed to evaporate under ambient conditions, crystallizing the SA. The plate was mounted in a Bruker Ultraflex III MALDI TOF/TOF mass spectrometer (Bruker Daltonics) equipped with a Smartbeam laser (Nd:YAG laser, 355 nm; spot diameter at sample=50 μm). After the laser ionization, ions were accelerated by a 20 kV electric field into the field-free flight tube and were detected in the positive ion linear detection mode. Spectra were exported as ASCII files and were processed using Origin 8 (OriginLab Corporation).

Preparation of Shrimp Extract.

About 25 g of shrimp was weighed and an equal mass of PBS buffer was added to the sample. The mixture was homogenized in a blender, then centrifuged at 3000 rpm for 1 h, and the supernatant was collected for use.

On-plate digestion and MS analysis of captured CTB. CTB was captured on a PSLB doped with GM1, as described above, and then enzymatically digested by spotting 10 μL of 0.01 μg/μL Trypsin Gold in 25 mM ammonium bicarbonate solution, pH 7.8, over the area of the PSLB that had been incubated with dissolved CTB. The digestion was carried out for 12 hours at 37° C. in a humidified chamber to prevent solvent evaporation after which the wafer was removed from the chamber and allowed to air-dry at room temperature. Different digestion times were tested and 12 hours was found to be optimal to maximize the intensities of the CTB peptide peaks for subsequent MS/MS analysis.

HCCA (20 μg) was dissolved in 250 μL of 50% acetonitrile, 2.5% trifluoroacetic acid and 47.5% nanopure water. One μL of this matrix solution was spotted onto the dried spot where the enzymatic digestion had taken place. One μL of peptide calibration standard II in HCCA solution was also spotted on the wafer. Wafers were mounted onto the MTP MALDI plate and analyzed using the MALDI TOF/TOF mass spectrometer as described above. The digested peptides were ionized, accelerated and detected in the reflectron mode for better resolution at lower mass-to-charge (m/z) ratios. After the full mass spectrum of the digested peptides was obtained, high energy (8 keV) collision induced dissociation was used to fragment the peptides to obtain sequence information (CID-LIFT mode with no added gas; background pressure is sufficient for CID as shown in the literature). Protein Prospector (University of California, San Francisco) was used to determine the theoretical m/z of the peptides generated from CTB digestion based on its amino acid sequence. The experimental peaks were compared to the theoretical peak list to make the assignments. For MS/MS spectral interpretation, b ions and y ions were compared and assigned according to the theoretical m/z values generated by Protein Prospector.

Results and Discussion

MALDI-TOF MS Detection of CTB, LTB and PTB.

Cholera toxin is composed of a dimeric A-subunit (Mr~27,400) and five identical B-subunits, and the sequence is available. Each B-subunit (Mr~11,600) contains a binding site for its membrane receptor, GM1. Heat-labile enterotoxin and cholera toxin are very similar with respect to structure, function and immunology; they also share GM1 as the cell surface receptor. Each B-subunit in LTB (Mr~12,000) is slightly larger than a CTB subunit (and the sequence is given in this reference). Pertussis toxin has an enzymatic component A protomer (S1, Mr~28,000) noncovalently bound to the B oligomer which is the binding component. Four dissimilar subunits form PTB:S2 (Mr~21,900), S3 (Mr~21,900), S4 (Mr~12,000) and S5 (Mr~11,750) in a molar ratio of 1:1:2:1, respectively.

Figure 32A:
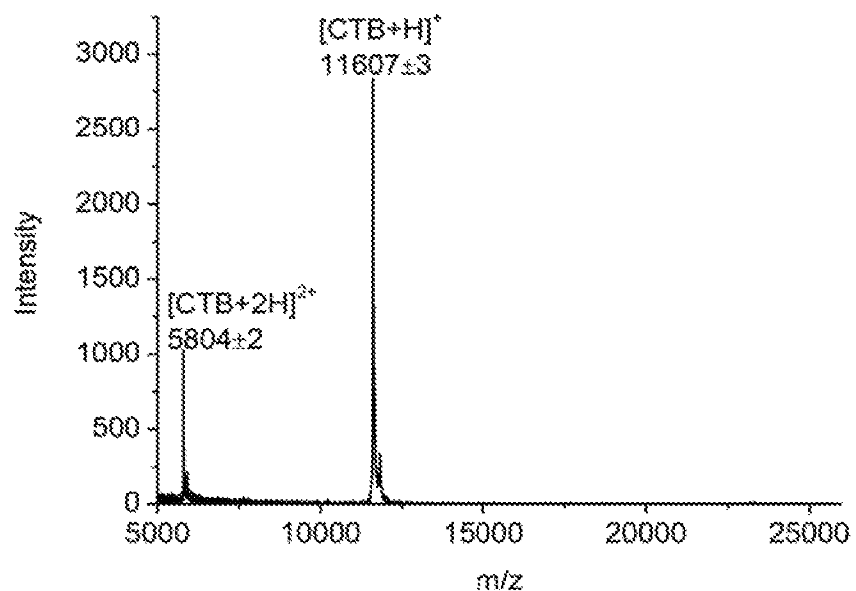
FIG. 32A) 0.24 μM CTB captured on a poly(bis-SorbPC) PSLB containing 1% GM1.
Figure 32B:
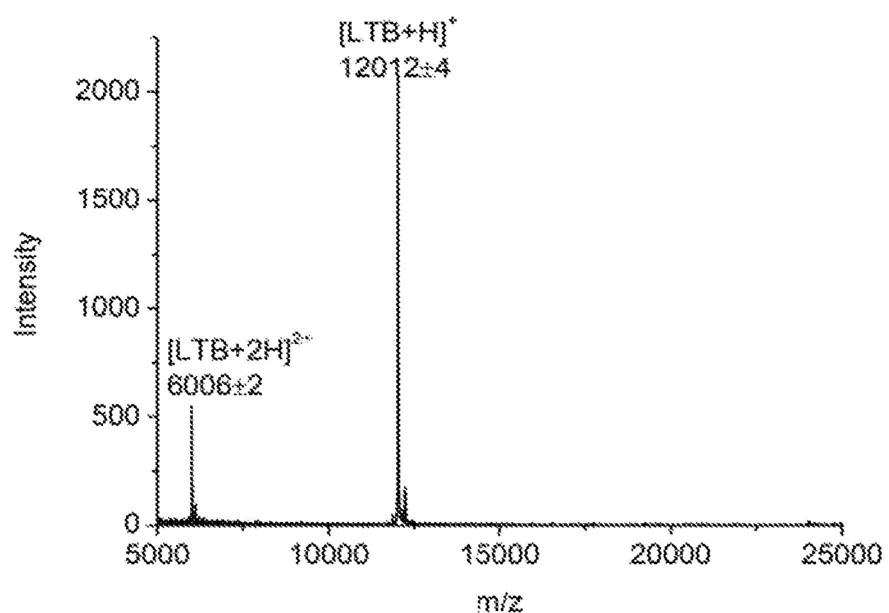
FIG. 32B) 0.24 μM LTB captured on a poly(bis-SorbPC) PSLB containing 1% GM1.

To assess the feasibility of using MALDI-TOF MS to detect toxins captured on polymerized PSLBs doped with gangliosides, initial experiments were performed using poly(bis-SorbPC) PSLBs doped with 1 mol % GM1 to capture CTB and LTB under conditions where the toxin concentration (0.24 μM) was sufficient to saturate the GM1 receptors in the PSLB (see Section 9 in SM). FIG. 32A shows a typical MALDI spectrum from a PSLB on which CTB was captured. The peak at 11,607 m/z corresponds to CTB monomer while the doubly charged monomer peak appears at 5804 m/z. Detection of the CTB monomer rather than the pentamer is most likely caused by dissociation of the B-subunits during exposure to the matrix and organic solvent. It is also possible that laser ionization disrupts the non-covalent interactions between monomers. LTB was captured and analyzed under identical conditions. A typical MALDI spectrum from a PSLB on which LTB was captured is shown in FIG. 32B; the pattern of singly and doubly charged peaks is similar to that observed for CTB. The singly charged LTB monomer peak was detected at 12,012 m/z and the doubly charged LTB monomer peak appeared at 6006 m/z.

Figure 32C:
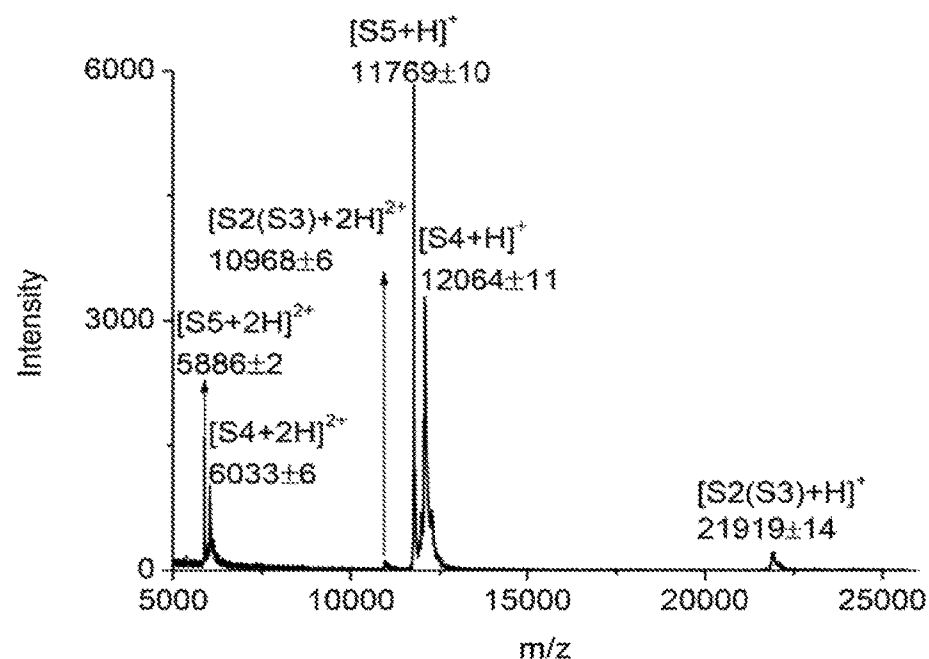
FIG. 32C) 1 μM PTB captured on a poly(bis-SorbPC) PSLB containing 20 mol % GD1a with subunits of PTB labeled as S1-S5.

Pertussis toxin B was captured on poly(bis-SorbPC) PSLBs containing 20 mol % GD1a from a 1 μM solution, which was sufficient to saturate the GD1a receptors in the PSLB. The ganglioside mol % was higher than that used for CTB and PTB based on preliminary experiments on poly(bis-SorbPC) PSLBs doped with GD1a at 10-40 mol % (see FIG. 44). At 10 mol %, the intensities of the PTB peaks were too weak to be reproducibly resolved. FIG. 32C shows a typical MALDI-TOF MS spectrum of a PSLB on which PTB was captured. Six peaks are assigned to the B-subunits described above. S4 appears as a singly charged peak at 12,064 m/z ($[S4+H]^+$) and a doubly charged peak at 6033 m/z ($[S4+2H]^{2+}$), while S5 appears as a singly charged peak at 11,769 m/z ($[S5+H]^+$) and a doubly charged peak at 5886 m/z ($[S5+2H]^{2+}$). The broad, low intensity peak at 21,919 m/z is assigned to singly charged S2 and S3 ($[S2, S3+H]^+$).

The spectra in FIGS. 32A-32C demonstrate successful capture of individual toxins on ganglioside-incorporated poly(bis-SorbPC) bilayers. Ganglioside recognition is clearly maintained after polymerization of the membrane, and the stability provided by cross-linking allows subsequent analysis by MALDI-TOF MS. The necessity for lipid polymerization was confirmed by attempting to capture CTB on a PSLB composed of 1 mol % GM1 and 99 mol % DPhPC followed by MALDI-TOF MS detection, following the same procedures used for PSLBs composed of 1 mol % GM1 and 99 mol % bis-SorbPC. No CTB peaks were detected in the mass spectrum (FIG. 37), demonstrating that a non-polymerized PSLB does not provide the stability required to conduct the MALDI MS analysis as described herein.

Background from Nonspecific Toxin Adsorption and Lipid Membrane Components.

Control experiments were performed to assess the degree of nonspecific adsorption of toxins to PSLBs because in any non-competitive bioaffinity assay, nonspecific adsorption is usually the major source of background. PSLBs composed of only poly(bis-SorbPC) (i.e., lacking gangliosides) were prepared and incubated with 0.24 μM CTB, 0.24 μM LTB, or 1 μM PTB, respectively. Nonspecific adsorption of CTB and PTB was not detectable (see FIG. 38). In the case of LTB, a small peak at ~12.0 k m/z was observed occasionally, indicating that nonspecific adsorption of LTB to poly(bis-SorbPC) is detectable (see FIG. 38B for an example). However, this peak was only observed in some trials and in those cases, the S/N was less than three. These results show that poly(bis-SorbPC) PSLBs have a high resistance to nonspecific toxin adsorption and that these membranes are highly resistant to nonspecific adsorption of other proteins.

Figure 32D:
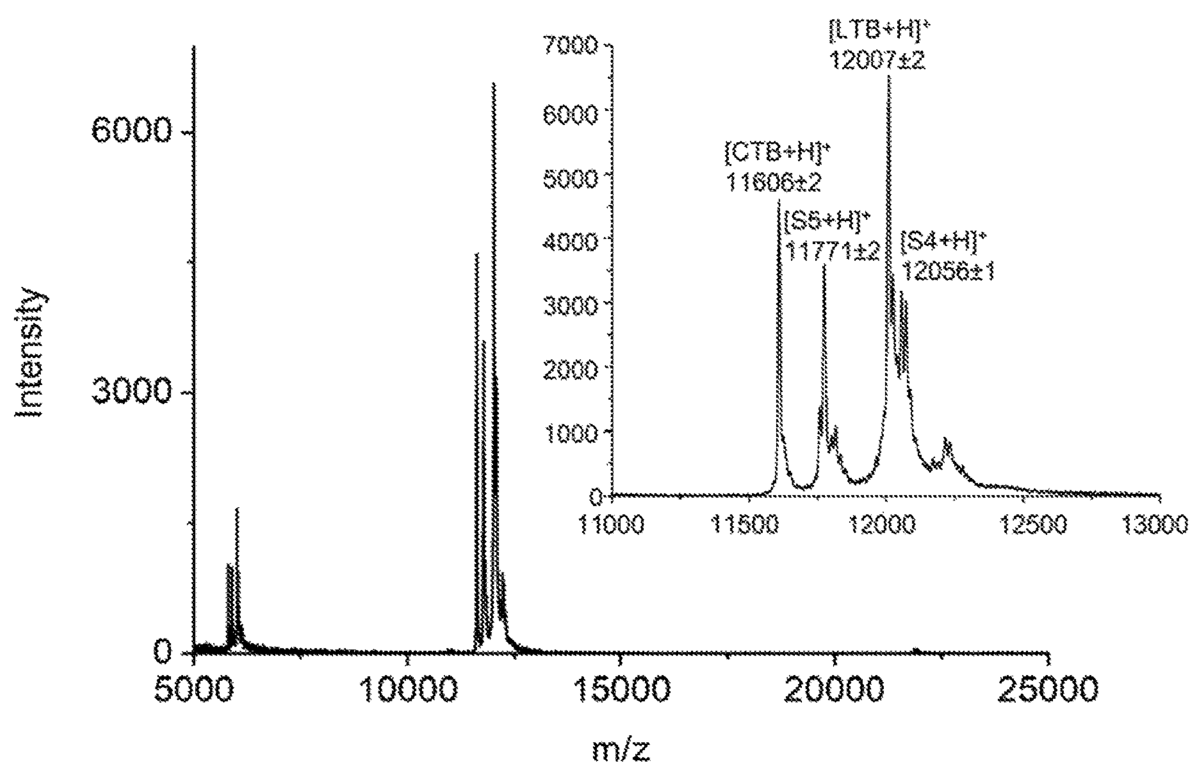
FIG. 32D) cholera toxin B (CTB), heat-labile enterotoxin B (LTB), and pertussis toxin B oligomer (PTB) captured simultaneously on a poly(bis-SorbPC) PSLB containing 1% GM1 and 20% GD1a. The inset in FIG. 32D is an enlargement of the 11000-13000 m/z range. Masses are reported as means and standard deviations that were determined from at least three independent measurements on captured toxins.
Figure 33A:
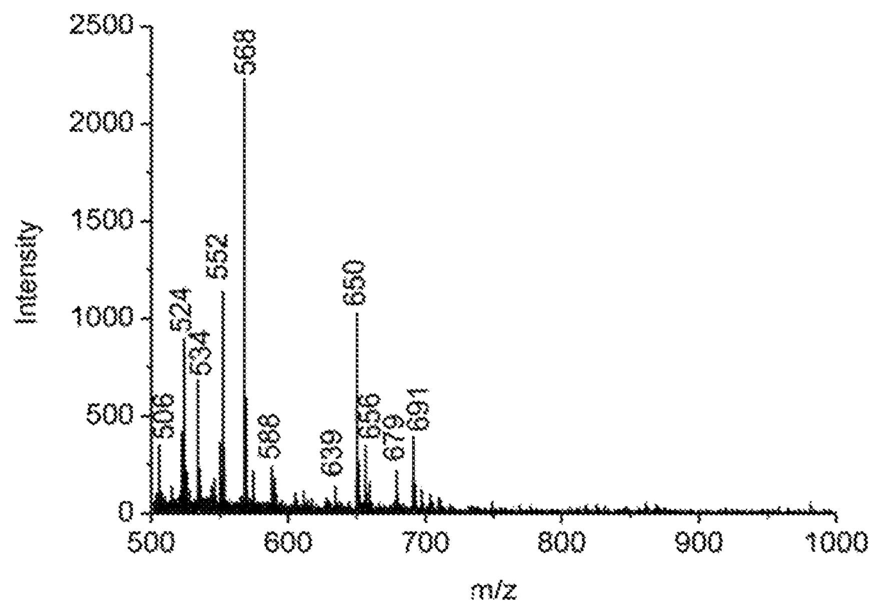
FIG. 33 shows MALDI-TOF MS spectra in the 500-1000 m/z range of FIG. 33A) HCCA spotted on a poly(bis-SorbPC) bilayer containing 1% GM1 and 20% GD1a and FIG. 33B) HCCA spotted directly on a MALDI plate.
Figure 33B:
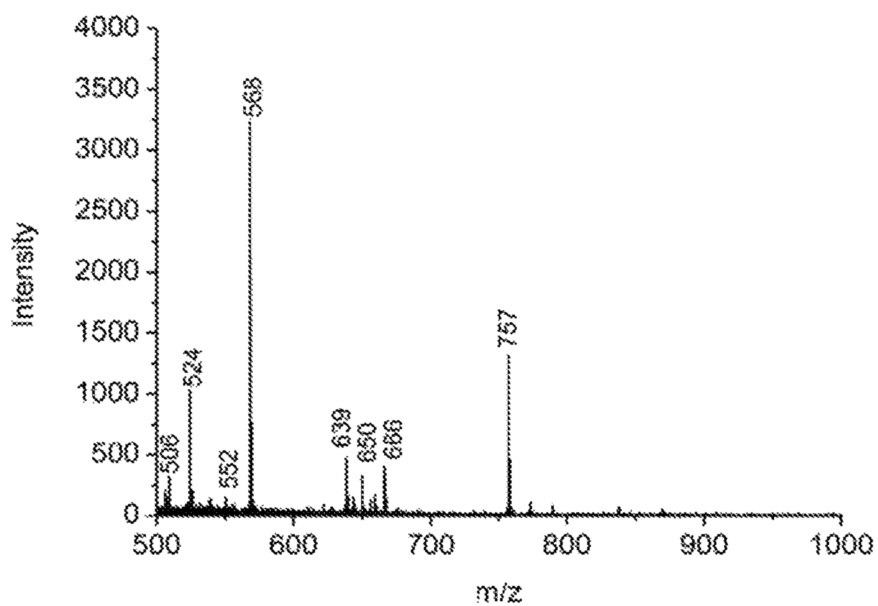
Figure 39A:
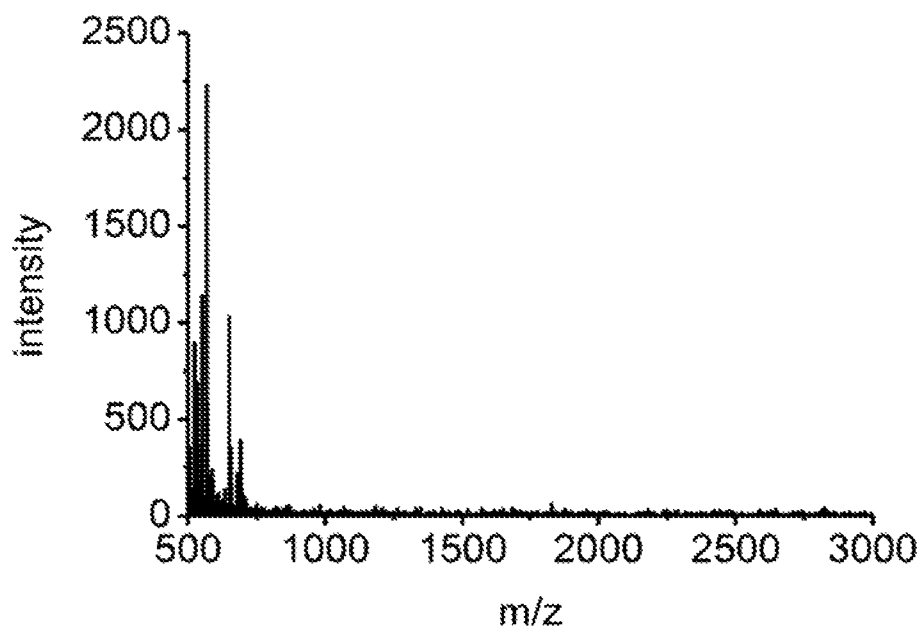
Figure 39B:
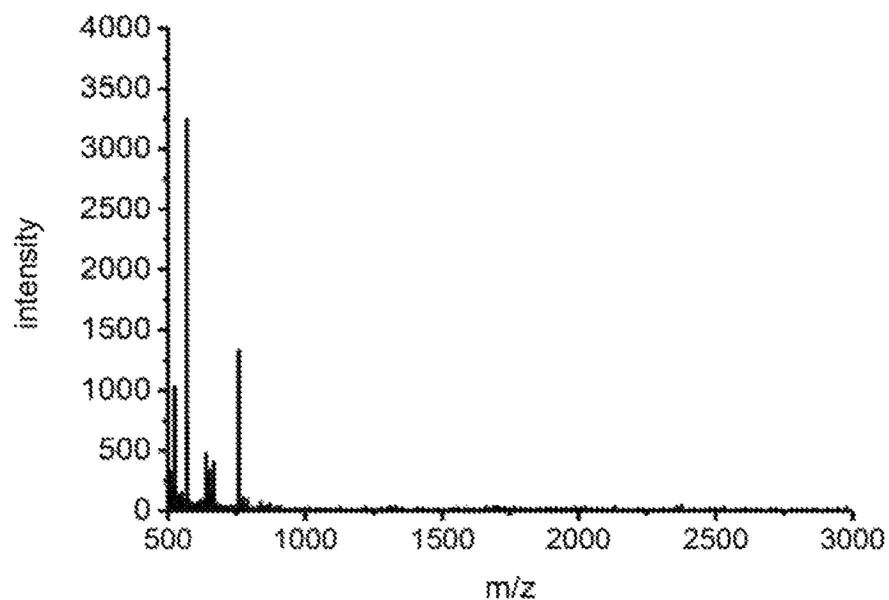
FIG. 39B) HCCA matix spotted directly on a MALDI plate. HCCA was spotted directly on a poly(bis-SorbPC) PSLB containing 1% GM1 and 20% GD1a and on a standard MALDI plate; the respective MALDI spectra are shown in FIG. 39. The ionization efficiencies are different on the two substrates for some matrix cluster ions which results in intensity differences for some peaks. The absence of peaks corresponding to GM1 (MW=1564 Da) and GD1a (MW=1836 Da) indicates that either the interactions between polymerized bis-SorbPC and gangliosides are not disrupted under experimental conditions or that the amount of ionized gangliosides is too low to be detected.
Figure 40A:
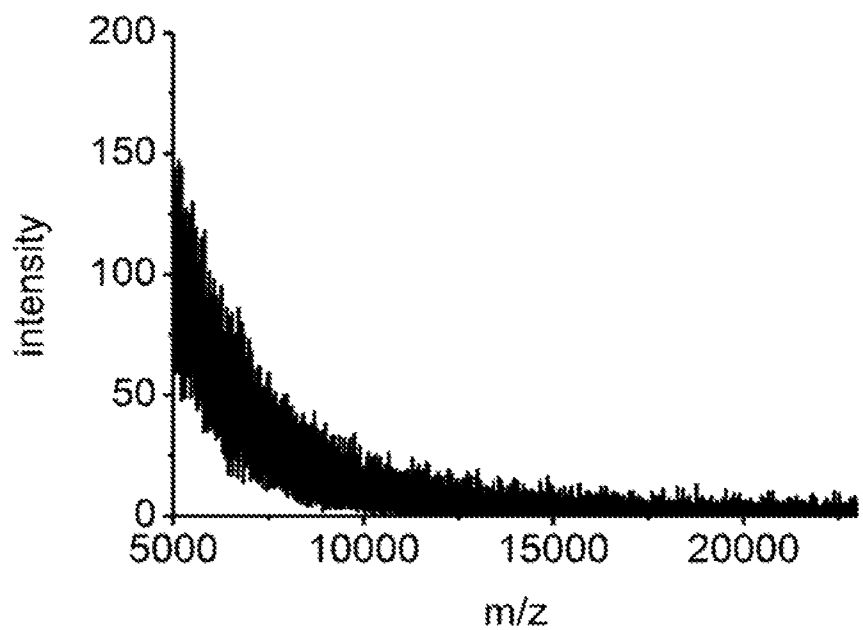
Figure 40B:
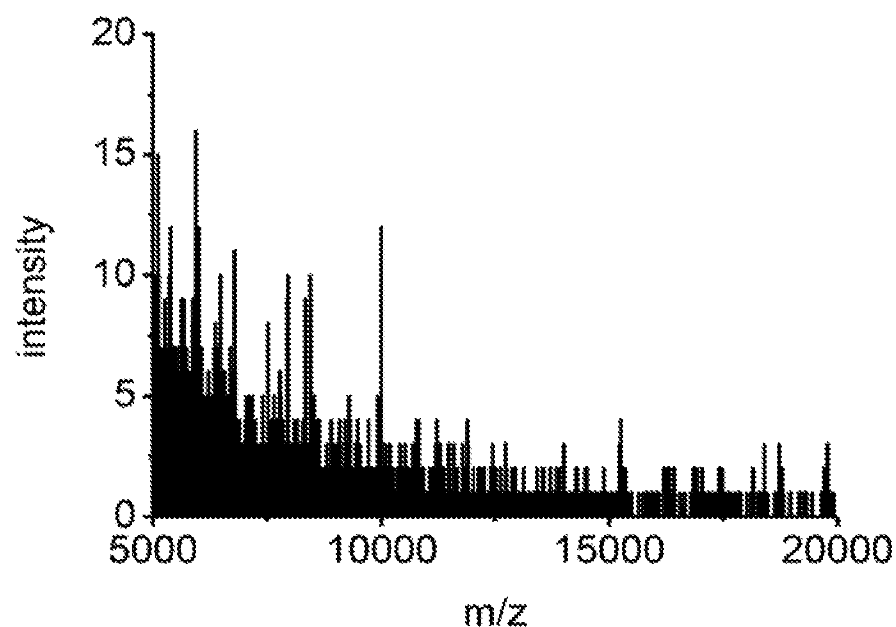
FIG. 40B) SA matrix spotted directly on a MALDI plate. SA was spotted directly on a poly(bis-SorbPC) PSLB containing 1 mol % GM1 and 20 mol % GD1a and on a standard MALDI plate; the respective MALDI spectra are shown in FIG. 40. The background from the lipid bilayer is greater than that from MALDI plate, which may be caused by differences in matrix crystallization on the two surfaces. However, the background intensity is much less than the intensity of peaks due to specifically captured toxin (FIG. 32).

Another set of control experiments was performed to assess if lipid molecules, either gangliosides or bis-SorbPC monomers and/or oligomers, could be detected. PSLBs composed of 1 mol % GM1 and 20 mol % GD1a in poly(bis-SorbPC) were prepared and analyzed by MALDI-TOF MS, as described above, except that the toxin incubation step was eliminated. HCCA and SA were used as the matrices for low and high m/z ranges, respectively. In FIG. 33, the HCCA matrix spectrum in the 500-1000 m/z range is compared with that of HCCA spotted directly on a MALDI plate. Matrix background peaks (e.g. m/z 568 and 757) were observed, as expected, but no lipid peaks appeared. The absence of a peak corresponding to the molecular weight (MW) of the bis-SorbPC monomer peak (MW=786 Da) indicates that the amount of ionized monomers is too low to be detected, consistent with a high degree of lipid polymerization. The HCCA spectra in the 500-3000 m/z range are shown in FIG. 39, respectively. No peaks corresponding to the molecular ions or fragment ions of GM1 (MW=1564 Da) and GD1a (MW=1836 Da) were detected, which suggests that ionization of these gangliosides is attenuated by their interactions with the polymerized bis-SorbPC membrane, and/or that the amount of ionized gangliosides and/or their fragment ions is too low to be detected. Mass spectra of SA spotted on a poly(bis-SorbPC) PSLB containing 1 mol % GM1 and 20 mol % GD1a and directly on a MALDI plate in the m/z range of 5-20 kD are shown in FIG. 40, respectively. The background from the lipid bilayer is greater than that from the plate but is low relative to the intensity of the toxin peaks shown in FIG. 32. Overall these data show that the lipid ionization background from ganglioside/poly(bis-SorbPC) PSLBs does not interfere with toxin detection under the conditions used herein.

Simultaneous Detection of CTB, LTB and PTB.

A number of label-free assays based on optical and electrochemical transduction principles have been developed for bacterial toxins, most notably for cholera toxin. However, these detection methods lack specificity, i.e., the signals from the analytes and nonspecific binding cannot be distinguished. Additionally, if two bacterial toxins target the same membrane receptor, as in the case of cholera toxin and heat-labile enterotoxin, these label-free methods cannot discern which toxin is present. In contrast, toxins with different molecular weights can be simultaneously captured on an affinity surface and identified in a label-free manner using MALDI mass spectrometry.

To assess the use of a ganglioside-doped lipid bilayer for simultaneous detection of CTB, LTB, and PTB, a poly(bis-SorbPC) PSLB containing 1 mol % GM1 and 20 mol % GD1a was incubated with a solution containing 0.24 μM CTB, 0.24 μM LTB, and 1 μM PTB. The mass spectrum is shown in FIG. 32D. The doubly charged monomer peaks appeared in the 5000-6000 m/z range. Resolution of the singly charged monomer peaks in the 11000-13000 m/z range is shown in the inset in FIG. 32D. The peaks at 11,606, 11,771, 12,007, and 12,056 m/z correspond to the CTB monomer ($[CTB+H]^+$), the PTB S5 monomer ($[S5+H]^+$), the LTB monomer ($[LTB+H]^+$), and the PTB S4 monomer ($[S4+H]^+$). Broad, low intensity peaks observed at ~21.9 k m/z and ~11.0 k m/z are assigned to S2 and S3 of PTB, as described above. The resolution at 12 k m/z is 1285 as calculated by FlexAnalysis (Bruker Daltonics); thus peaks separated by 12000/1285=9 m/z can be resolved which is consistent with the Bruker specification of resolution >1100 in linear mode.

The correspondence of the peaks in FIG. 32D with the individual toxin peaks present in FIGS. 32A-32C demonstrates the capability to capture and detect three protein toxins simultaneously. This result suggests the possibility of using a poly(lipid)-based affinity capture platform, fabricated as a two-dimensional array, for high throughput screening of samples for ligands. The number of analytes presumably could be greater than three, assuming that the surface coverage of each analyte was sufficient for detection and they could be distinguished on the basis of differences in m/z.

Application of the Affinity Capture Platform in Complex Samples.

Figure 34A:
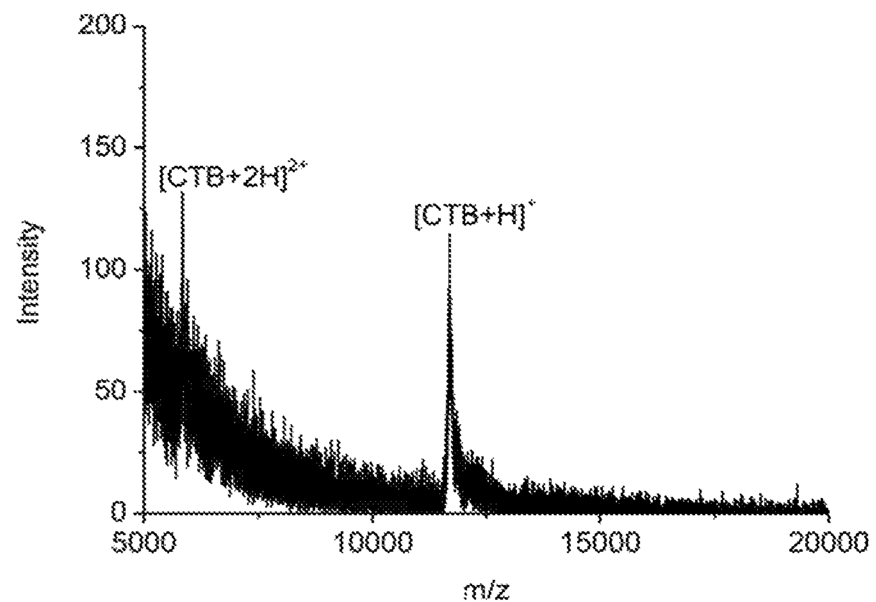
FIG. 34A and FIG. 34B show MALDI-TOF MS spectra of 0.24 μM CTB captured on a poly(bis-SorbPC) PSLB containing 1% GM1 in the presence of FIG. 34A) 10% (v/v) FBS and FIG. 34B) 10% (v/v) shrimp extract.
Figure 34B:
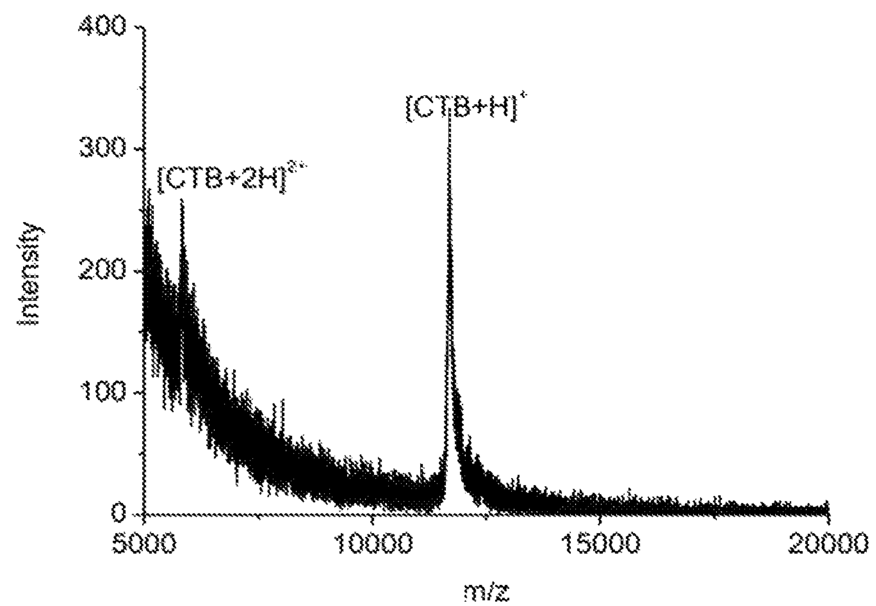
Figure 41A:
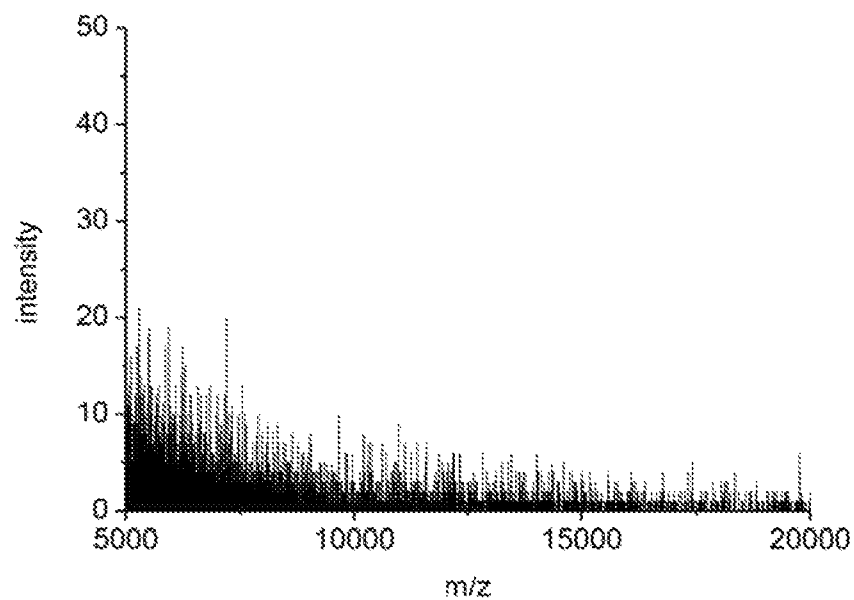
FIG. 41 shows MALDI-TOF MS spectra of poly(bis-SorbPC) PSLBs containing 1% GM1 after incubation with FIG. 41A) 10% (v/v) FBS and FIG. 41B) 10% (v/v) shrimp extract. To assess if components in complex matrices (FBS and/or shrimp extract) adsorb nonspecifically to poly(bis-SorbPC) PSLBs, control experiments were performed by incubating 10% (v/v) FBS or shrimp extract on a poly(bis-SorbPC) PSLB doped with 1 mol % GM1. The respective mass spectra are shown in FIG. 41. No peaks were detected.
Figure 41B:
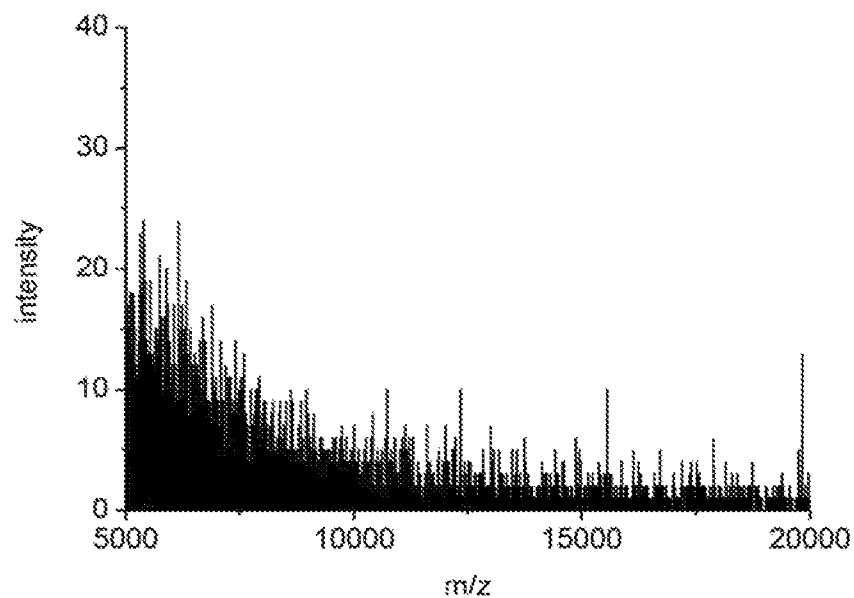
Figure 42A:
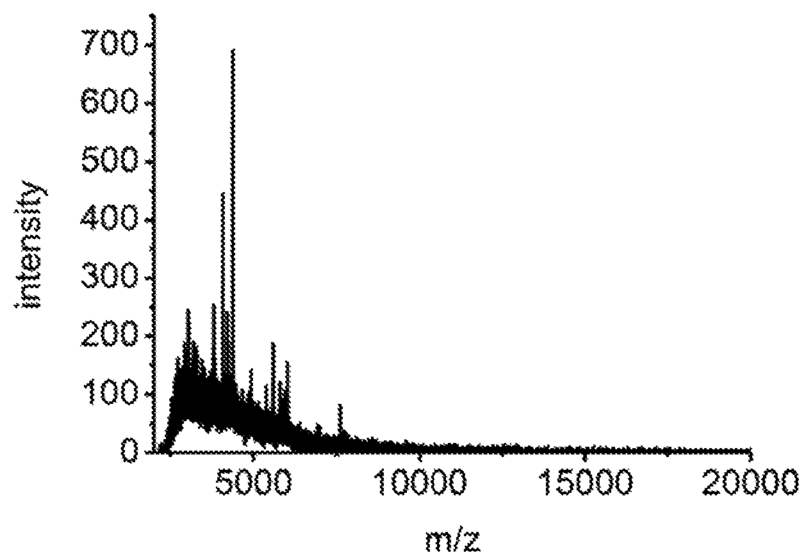
FIG. 42 shows MALDI-TOF MS spectra of FIG. 42A) 1% (v/v) FBS and FIG. 42B) 1% (v/v) shrimp spotted on standard MALDI plate. The inset of SM-6b is the same mass spectrum in the 5000-12000 m/z range. One μL of FBS or shrimp extract (10% (v/v)) was spotted on a standard MALDI plate and air-dried. One μL of HCCA in acetonitrile: $H_2O$ (50:50, v/v) was then spotted on the dried sample and air-dried. MALDI-TOF MS analysis was performed and the respective mass spectra are shown in FIG. 42. Peaks were detected that did not appear in the FIG. 41, demonstrating the resistance of poly(bis-SorbPC) PSLBs to nonspecific adsorption of components in FBS and shrimp extract.
Figure 42B:
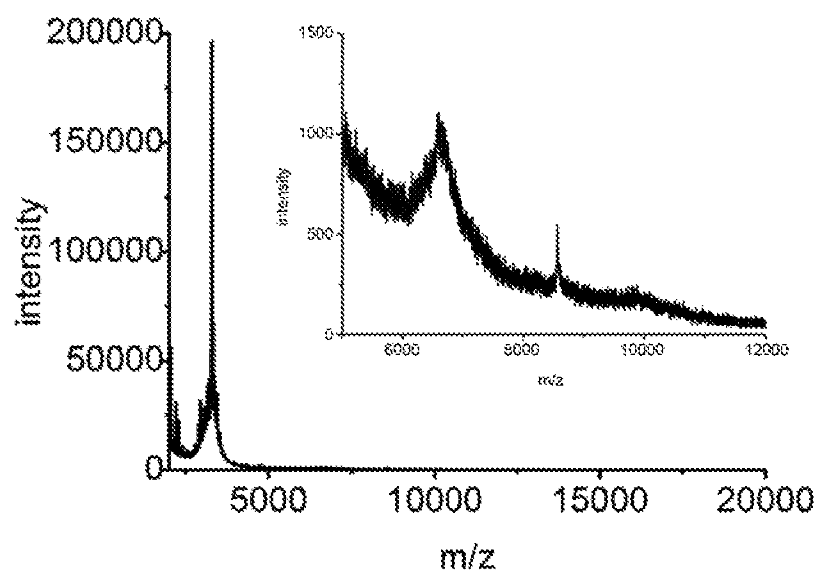

Typically, biological samples contain analyte(s) in a complex matrix of biomolecules and other components, such as tissue homogenate, fecal matter, blood serum, etc. To assess the utility of the poly(lipid)-based affinity capture platform in complex samples, analysis of CTB in both fetal bovine serum (FBS) and shrimp extract as the sample matrix was performed. CTB was spiked into either 10% (v/v) of FBS or 10% (v/v) of shrimp extract in PBS buffer, at a final CTB concentration of 0.24 μM, and the samples were incubated with poly(bis-SorbPC) PSLBs containing 1 mol % GM1, followed by rinsing, drying, and analysis as described above. Representative mass spectra are shown in FIGS. 34A and 34B. Peaks corresponding to singly and doubly charged CTB monomer peaks were clearly detectable despite the presence of a large excess of other proteins, although the peak intensities were generally lower than when the matrix was 100% buffer (compare to FIG. 32A). Two sets of control experiments were performed: a) 10% (v/v) of FBS and 10% (v/v) of shrimp extract were incubated with poly(bis-SorbPC) PSLBs containing 1 mol % GM1, rinsed, dried, and analyzed; the resulting spectra are shown in FIG. 41, 10% (v/v) of FBS and 10% (v/v) of shrimp extract were spotted directly on a MALDI plate, and the resulting spectra are shown in FIG. 42. These spectra show that some components in FBS and shrimp extract are detectable when spotted directly on a MALDI plate, as expected. However, they are not detectable when spotted on a poly(bis-SorbPC) PSLB, consistent with the low degree of nonspecific adsorption described above. Overall these results demonstrate that CTB can be selectively captured on a PSLB when present in a complex biological matrix.

Minimal Detectable Concentration.

The CTB-GM1 pair was used as a model system to estimate the minimal detectable concentration of protein captured on the PSLB-based affinity platform. Due to the semi-quantitative properties of MALDI-TOF MS, an approach based on the frequency with which CTB could be detected was used. After CTB was captured by a poly(bis-SorbPC) PSLB doped with GM1, SA matrix was spotted on different areas on the substrate. Multiple substrates were prepared and up to five matrix spots could be applied on each (the number of samples per substrate varied due to differences in substrate area). Due to the nature of dry-droplet matrix deposition, spatially heterogenous crystal formation occurs across the matrix spot which causes significant variations in signal strength. To overcome this variable, the laser was scanned across entire area of each matrix spot at distance intervals of less than 50 μm (the diameter of the laser spot). Detection of a CTB monomer peak at 11.6 k m/z with a S/N≥3 anywhere on the substrate was recorded as a detectable sample.

The minimal detectable concentration is defined here as the CTB solution concentration that produces a peak with S/N≥3 for 100% of the samples analyzed. In these experiments, the mol % of GM1 was constant (1 mol % in poly(bis-SorbPC)) and the CTB concentration of the solution that was incubated with the PSLB was varied. A large CTB concentration range, from 0.5 nM to 1 μM, was screened, from which the minimal detectable concentration was determined to be in the range of 1-5 nM. A larger number of samples was prepared and analyzed in this concentration range, with each matrix spot counted as one sample. The number of samples that gave a CTB m/z peak with S/N≥3 divided by the total number of samples is reported as a detection frequency in Table 15. At 4 nM CTB, the detection frequency is 100%, so this concentration is a conservative estimate of the minimal detectable CTB concentration. With respect to definitions used in clinical chemistry, 4 nM CTB is the concentration that produces a sensitivity of 100%, and since CTB was never detected in samples lacking the toxin, the specificity is 100%. The estimate of 4 nM is specific to the analysis conditions employed here, for example, the amount of GM1 is finite and the incubation time was selected to achieve an apparent steady state (but not equilibrium which, due to mass transport limitations, would have required much longer times). The minimal detectable concentration of CTB likely could be lowered by increasing the mol % of GM1 and the incubation time. The dissociation constant ($K_D$) for GM1-CTB also plays a role. Apparent $K_D$ values reported for CTB-GM1 range from 4.55 μM to 370 nM, a very wide range attributed to significant differences in experimental parameters; thus it is also possible that at 4 nM, the amount of bound CTB is limited by its binding affinity to GM1. Minimal detectable concentrations for cholera toxin using label-free SPR methods are in the nM range, such as the 4 nM reported here.

Table 15 provides estimations of the MALDI-TOF MS minimal detectable concentration for CTB bound to 1 mol % GM1 in poly(bis-SorbPC) PSLBs.[a]

Table 15 provides estimations of the MALDI-TOF MS minimal detectable concentration for CTB bound to 1 mol % GM1 in poly(bis-SorbPC) PSLBs. [a]

| Concentration of CTB (nM) | Frequency of samples that gave a S/N ≥3 [b] | Number of silicon wafers prepared |
|---|---|---|
| 1 | 0/10 | 2 |
| 2 | 8/16 | 3 |
| 3 | 11/15 | 3 |
| 4 | 9/9 | 2 |
| 5 | 10/10 | 2 |

[a] This table focuses on a narrow CTB concentration range that was identified from screening samples over a larger concentration range.
[b] Frequency is reported as the number of samples in which CTB was detected/total samples that were analyzed.

On-Plate Tryptic Digestion of Captured CTB.

Molecular weight information may be adequate to identify multiple analytes with resolvable molecular weights, as demonstrated above. However, when multiple analytes cannot be distinghuished solely based on molecular weight differences, additional steps may be necessary. To further explore the applicability of the PSLB-based affinity capture platform, on-plate tryptic digestion of captured CTB was performed and the fingerprint spectra of CTB peptide fragments were obtained. A solution of 0.24 μM CTB was incubated with a poly(bis-SorbPC) bilayer doped with 1 mol % GM1, rinsed with nanopure water, and dried. The trypsin concentration and on-plate digestion time were varied to obtain maximum amino acid coverage (data not shown). The optimal conditions were found to be 0.01 μg/μL Trypsin Gold and 12 hours, respectively, and MALDI-TOF MS was performed on CTB peptides generated using these conditions.

Figure 35:
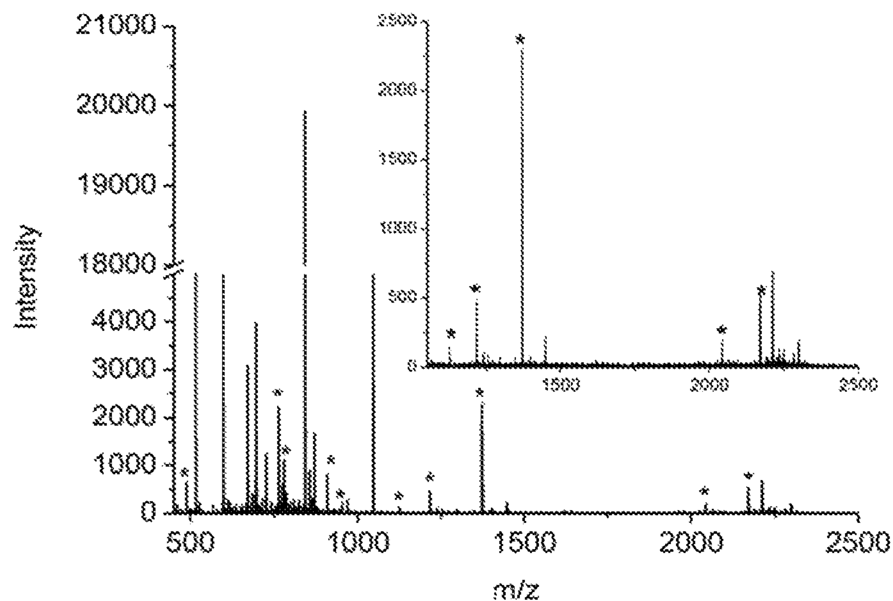
FIG. 35 is a representative MALDI-TOF mass spectrum of CTB captured on a poly(bis-SorbPC) PSLB containing 1% GM1 and subjected to on-plate tryptic digestion. The observed CTB peptide fragment peaks are marked with asterisks. The peaks marked with open circles are assigned to trypsin autolysis. The inset is an enlargement of the 1150-3000 m/z range, where CTB peptide peaks are most abundant.

A typical mass spectrum, in which the CTB peptides produced by digestion are labeled with asterisks, is shown in FIG. 35. Other peaks are assigned mostly to trypsin autolysis products. The 12 CTB tryptic peptides that were detected are listed in Table 16; these peptides account for 57% coverage of the CTB amino acid sequence. Sequences 1-22 and 82-103 are connected through intra-chain disulfide bonds and were not detected; it is possible that disulfide bridge reduction may be necessary to achieve full coverage.

Table 16 is a summary of peptide fragments observed in MALDI-TOF mass spectra of a CTB tryptic digest.

| Fragment (amino acid start-end) | Sequence | Calculated $MH^+$ (Da) | occurrence frequency* | Confirmed by MS/MS? |
|---|---|---|---|---|
| 64-67 | (K)AIER(M) | 488.28 | 3/4 | |
| 70-73 | (K)DTLR(I) | 504.28 | 1/4 | |
| 64-69 (1 Oxidation) or 68-73 | (K)AIERMK(D) or (R)MKDTLR(I) | 763.41 | 3/4 | |
| 68-73 (1 Oxidation) | (R)MKDTLR(I) | 779.4 | 3/4 | |
| 74-81 | (R)IAYLTEAK(V) | 908.51 | 3/4 | |
| 36-43 | (R)EMAIITFK(N) | 952.52 | 4/4 | |
| 35-43 | (K)REMAIITFK(N) | 1108.62 | 1/4 | |
| 35-43 (1 Oxidation) | (K)REMAIITFK(N) | 1124.61 | 4/4 | |
| 24-34 | (K)IFSYTESLAGK(R) | 1215.62 | 4/4 | Y |
| 24-35 | (K)IFSYTESLAGKR(E) | 1371.72 | 4/4 | Y |
| 44-62 | (K)NGATFQVEVPGSQHIDSQK(K) | 2041.99 | 4/4 | Y |
| 44-63 | (K)NGATFQVEVPGSQHIDSQKK(A) | 2170.09 | 4/4 | |

*Occurrence frequency is the number of samples in which the fragment peak appeared/total samples. Four samples were analyzed.

Figure 36A:
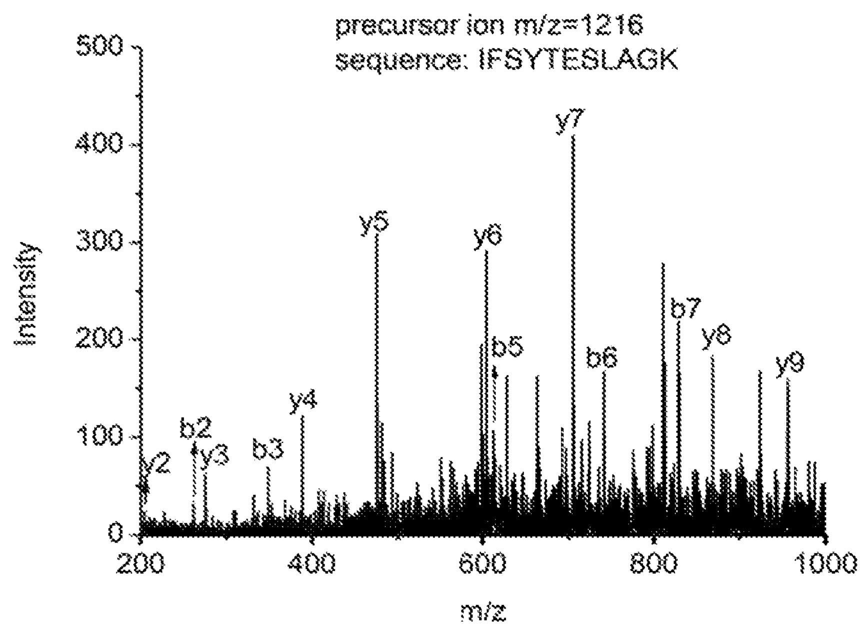
FIG. 36A) 1216 Da, FIG. 36B) 1372 Da and FIG. 36C) 2042 Da. Because these peptides were derived from a known protein (captured CTB), the m/z values of y ions and b ions were assigned by submitting the appropriate CTB sequence to Protein Prospector. In the case of an unknown protein, a search algorithm would be used. The Mascot algorithm was applied, although Mascot scores are known to vary with search parameters. Mascot scores for the spectra in FIG. 36A-36C, obtained with a typical set of search parameters, are 55, 38, and 96, respectively, with the score trend consistent with the S/N ratios apparent in the spectra. Mascot would have identified CTB based on the scores for the peptides in FIG. 36A and FIG. 36C, but not FIG. 36B.
Figure 36B:
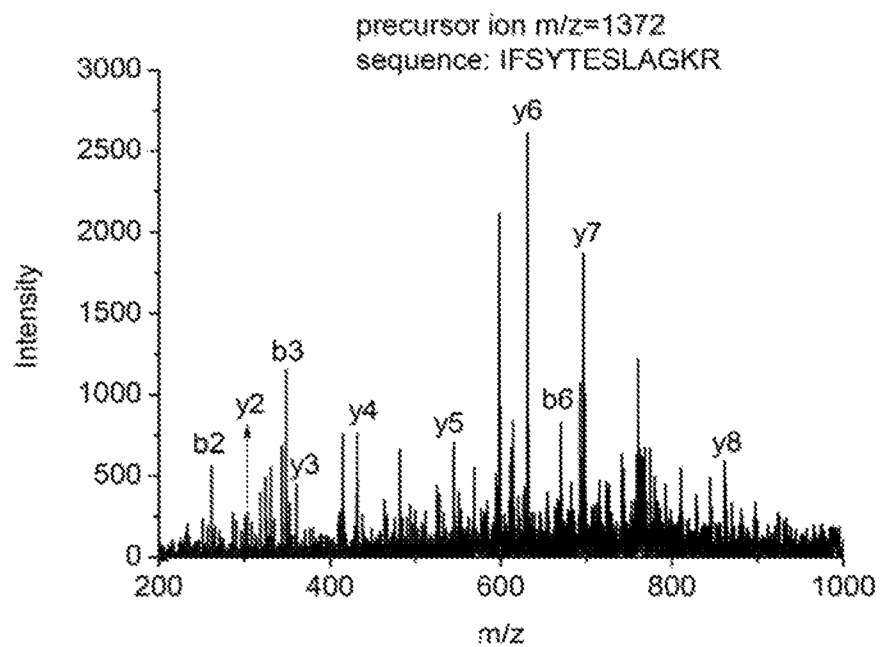
FIG. 36 shows MALDI MS/MS spectra of peptides generated by on-plate tryptic digestion of CTB captured on a poly(bis-SorbPC) PSLB containing 1% GM1. The peptide $MH^+$ values are.
Figure 36C:
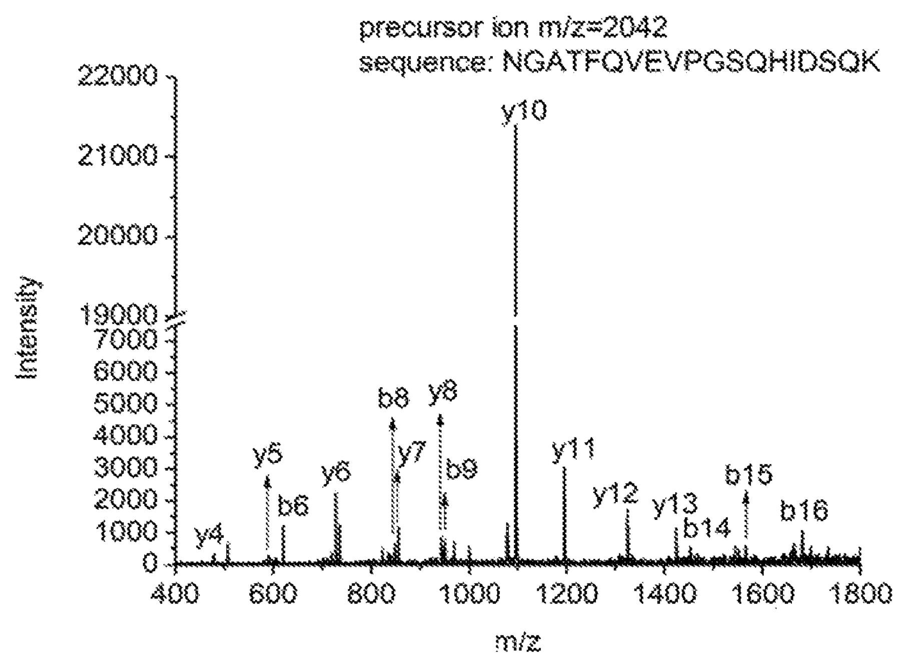
Figure 37:
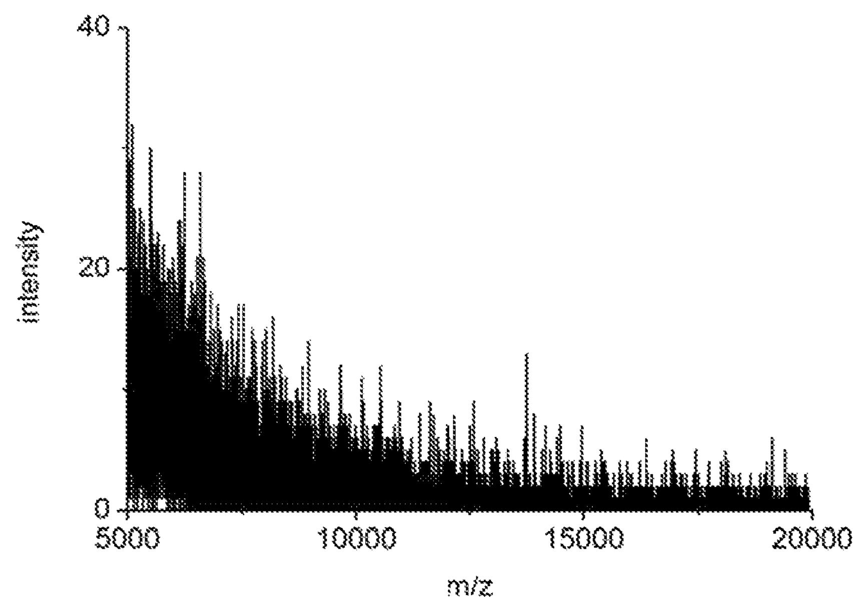
FIG. 37 shows MALDI-TOF MS spectrum of a PSLB composed of 1 mol % GM1/DPhPC that was incubated with 0.24 μM CTB. To assess the compatibility of a fluid PSLB with MALDI-TOF MS detection, 1,2-diphytanoyl-sn-glycero-3-phosphocholine (DPhPC, purchased from Avanti Polar Lipids), a non-polymerizable lipid, was used. PSLBs with bound CTB were prepared and subjected to MS analysis following the same procedures used for PSLBs composed of 1 mol % GM1 and 99 mol % bis-SorbPC, as shown in FIG. 37. No CTB peaks were detected, regardless of whether or not the PSLB was irradiated with UV light, which shows that a fluid PSLB does not provide the stability needed for MALDI-TOF MS analysis.
Figure 38A:
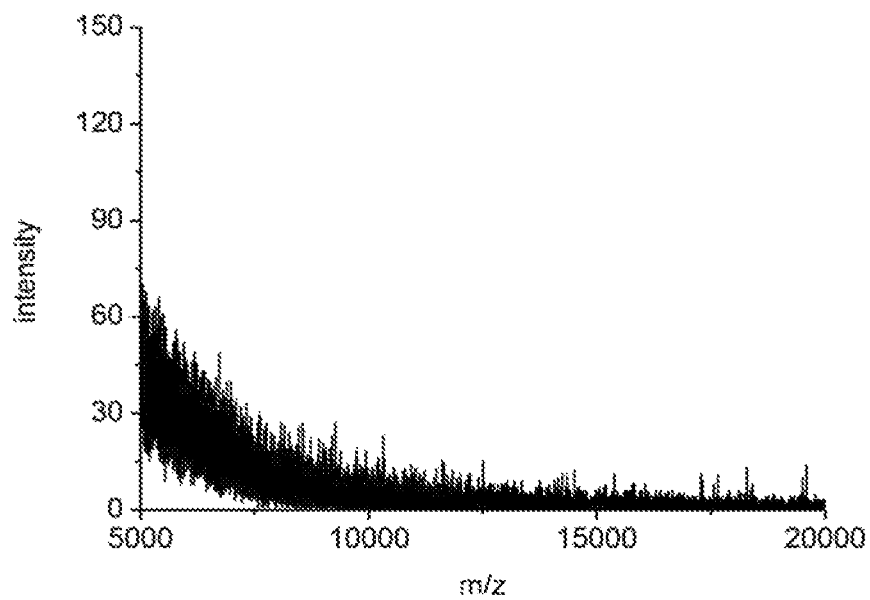
FIG. 38A) 0.24 μM CTB.
Figure 38B:
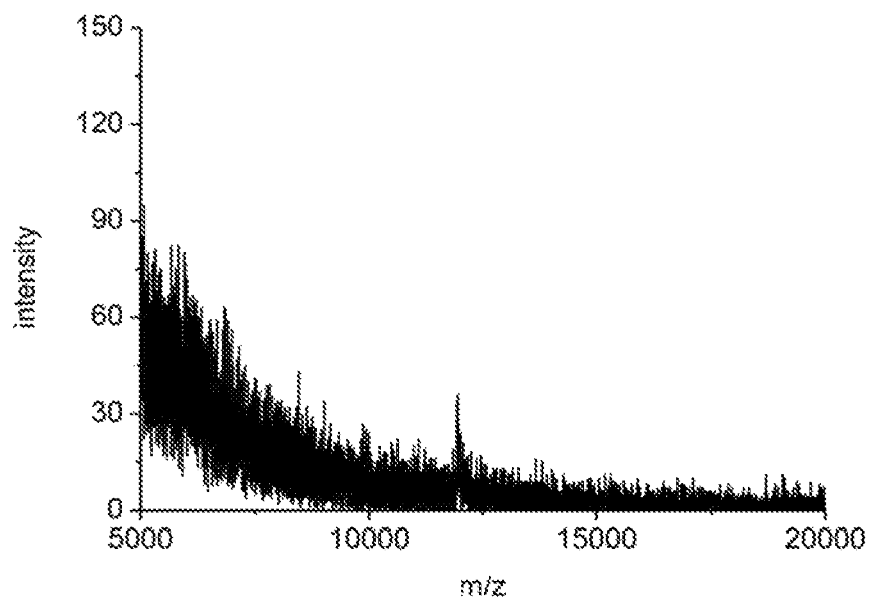
FIG. 38B) 0.24 μM LTB.
Figure 38C:
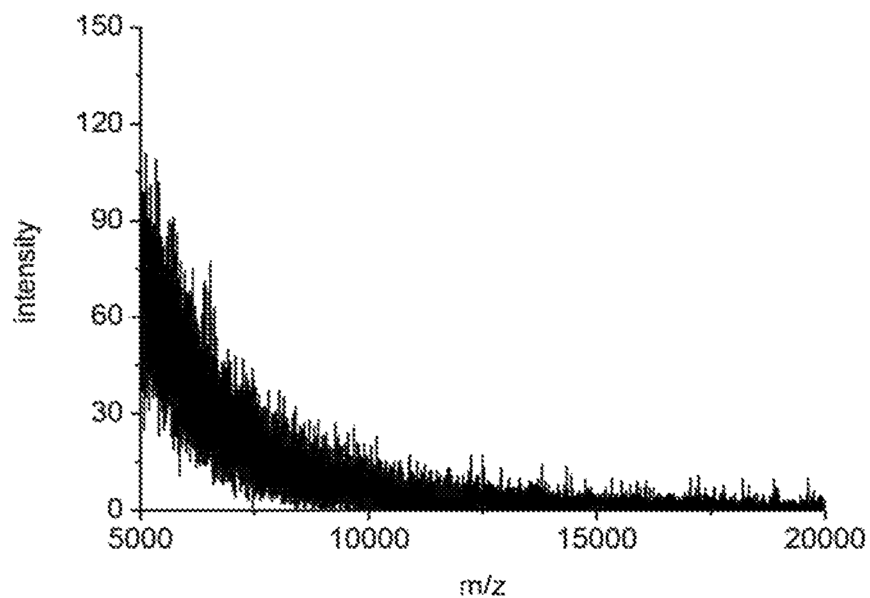
FIG. 38C) 1 μM PTB. To determine the degree of nonspecific adsorption of bacterial toxins to poly(bis-SorbPC), poly(bis-SorbPC) PSLBs lacking gangliosides were incubated with 0.24 μM CTB, 0.24 μM LTB, or 1 μM PTB. MALDI-TOF MS detection was carried out and the respective results are shown in FIG. 38. Nonspecific toxin adsorption of CTB and PTB was not detectable under the experimental conditions. Some experiments with LTB showed a small peak near 12.0 kDa. However, when this peak was observed, the S/N was always <3.

In some cases, e.g. when analyzing multiple and/or unknown proteins, the m/z of the constituent peptides may not be sufficient to identify the proteins; in these cases, identification may be possible using MS/MS. Here the amino acid sequences of three peptides produced by on-plate tryptic digestion of captured CTB were obtained using MS/MS. These three peptides were selected for analysis because their relative yields were high in comparison to those of the other nine peptides (which were too low for this analysis). Spectra of sequences with MWs of 1216 Da, 1372 Da and 2042 Da are shown in FIG. 36 and listed in Table 16. The mass difference between the measured m/z and the theoretical m/z of identified b ions and y ions is within 0.4 m/z. Overall, the results obtained from MALDI-TOF MS and MS/MS detection of peptides produced by on-PSLB tryptic digestion of CTB show that the PSLB-based affinity capture platform should be useful for identifying captured proteins with very similar molecular weights.

Minimal Detectable Surface Coverage of CTB.

Another estimate of the minimal detectable concentration was obtained by maintaining the CTB concentration at a high, constant value (0.24 μM) and varying the mol % of GM1 in the PSLB from 0.005 to 1 mol %. Under these conditions, the concentration of CTB greatly exceeds the GM1 concentration and it is reasonable to assume that one CTB pentamer binds to each GM1; thus this method provides an estimate of the minimal detectable concentration in units of protein surface coverage. PSLBs with a large mol % range of GM1 (0.005-1 mol %) were prepared and screened for CTB detectability. The minimal detectable surface coverage was determined to reside in the range of 0.01-0.05 mol %; thus more samples were prepared in this range. The results are reported in Table 17. At less than 0.05 mol %, the detection frequency was low but reached unity at 0.05 mol % and above. Assuming one bound CTB per GM1 and respective projected molecular areas for GM1 and bis-SorbPC of ~1 $nm^2$ and ~0.5 $nm^2$, the surface coverage of CTB bound to 0.05 mol % GM1 in a bis-SorbPC PSLB is $1.7\times10^{-13}$ mol/$cm^2$. This surface coverage corresponds to ~3% of a CTB monolayer, assuming that one monolayer is $6.6\times10^{-12}$ mol/$cm^2$ based on a projected area of ~25 $nm^2$ per CTB pentamer. Assuming the average matrix spot diameter is ~2 mm, this surface coverage corresponds to ~$2\times10^{-14}$ mol of CTB within one matrix spot and ~$5\times10^{-16}$ mol of CTB within one 50 μm diameter laser spot.

Table 17 provides estimations of the MALDI-TOF MS minimal detectable surface coverage for 0.24 μM CTB using various GM1 mol % in poly(bis-SorbPC) bilayers.[a]

| Concentration of GM1 (mol %) | Frequency of samples that gave a S/N ≥3[b] | Number of silicon wafers prepared |
|---|---|---|
| 0.01 | 3/17 | 4 |
| 0.02 | 2/18 | 4 |
| 0.03 | 1/20 | 4 |
| 0.04 | 0/22 | 5 |
| 0.05 | 10/10 | 2 |

[a]This table focuses on a narrow range of GM1 mol % that was identified from a screening samples over a larger range of GM1 mol %.
[b]Frequency is reported as the number of samples in which CTB was detected/total samples that were analyzed.

Saturable Binding of Toxins to Poly(Bis-SorbPC) PSLBs Doped with Gangliosides.

CTB labeled with Alexa Fluor 488 (Alexa 488-CTB) was purchased from Invitrogen (Eugene, Oreg.). Total internal reflection fluorescence microscopy (TIRFM) was used to measure the binding of Alexa 488-CTB to 1 mol % GM1 in a polymerized bis-SorbPC PSLB. The TIRFM system has been described previously. The 488 nm line of an $Ar^+$ laser (Ion Laser Technology) was coupled into a fused silica slide using a 45° prism (Edmund Optics). Immersion oil (Type FF, Cargille Laboratories, Cedar Grove, N.J.) with a refractive index of 1.4790 was used to couple the prism to the fused silica slide, which formed the lower wall of a liquid flow cell that was mounted on an stage of an inverted microscope (Nikon Diaphot). The PSLB was formed on the upper surface of the slide as described in manuscript. One of the internal reflections at the upper surface of the slide was used to excite fluorescence from Alexa 488-CTB bound to the PSLB. The fluorescence signal was collected using a 4× objective, directed through a 535DF35 (Omega Optical, Brattleboro, Vt.) band pass filter, and detected using CCD (Andor Technology USA, South Windsor, Conn.).

Figure 43:
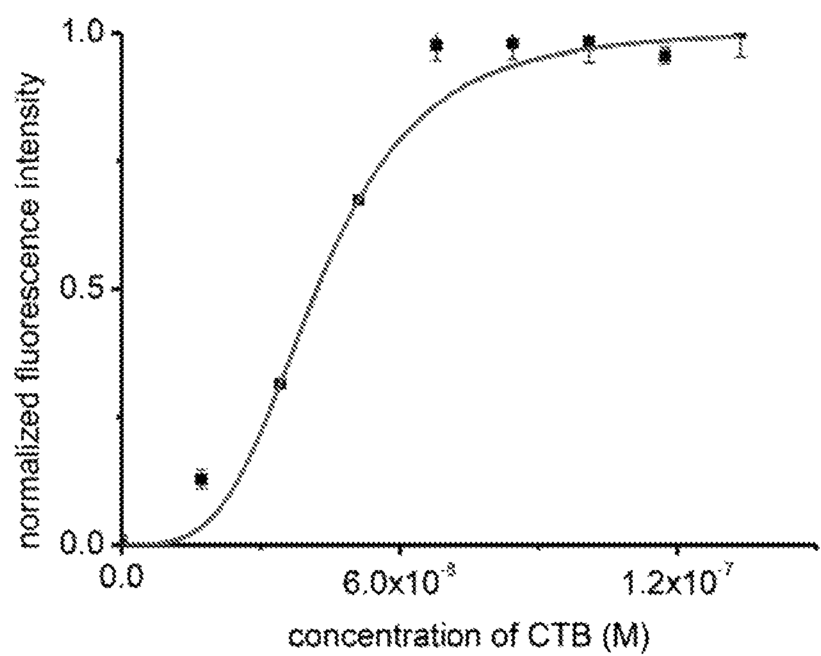
FIG. 43 shows TIRFM measurement of CTB binding to 1 mol % GM1 doped in a polymerized bis-SorbPC PSLB. Phosphate buffered saline (PBS) was used to measure the background. Alexa 488-CTB solutions (500 μL) were then injected into the flow cell, sequentially from the lowest concentration to the highest. One hour of static incubation after each injection, the fluorescent signal from GM1-bound Alexa 488-CTB was then measured. The fluorescent signal from dissolved Alexa 488-CTB was negligible so the dissolved protein solution was not flushed from the cell before each measurement. The solid line is a fit of the data to the Hill equation.

The binding curve in FIG. 43 shows that Alexa 488-CTB saturates the PSLB when the dissolved concentration is approximately 0.1 μM. A concentration greater than this (0.24 μM) was used to prepare PSLBs saturated with CTB for use in MALDI-TOF MS experiments. In the case of LTB and PTB binding to polymerized bis-SorbPC PSLBs doped with 1 mol % GM1 and 20 mol % GD1a, respectively, existing binding data was relied upon.

Conclusions

This work demonstrates that cross-linking lipid polymerization provides the stability necessary for implementation of a receptor-doped PSLB as an affinity capture platform for label-free protein detection using MALDI-TOF MS. Simultaneous capture and detection of CTB, LTB and PTB was performed, showing that differences in ligand molecular weight are sufficient to distinguish among multiple captured proteins. The high resistance of poly(bis-SorbPC) membranes to nonspecific protein adsorption is another feature that makes them useful for analysis of complex biological matrices. In some cases, differences in molecular weights among captured proteins may be inadequate for their identification. As demonstrated here, on-PSLB trypsin digestion can be employed to obtain the molecular weights of peptide fragments using MS/MS, which illustrates the potential use of the PSLB-based platform for proteomic identification of membrane-associated proteins. Finally, it is feasible to incorporate transmembrane proteins, such as bovine rhodopsin and ion channels, into poly(lipid) membranes with retention of activity. This suggests the possibility of using the approaches described herein to capture and identify ligands that bind to transmembrane protein targets.

As used herein, the term "about" refers to plus or minus 10% of the referenced number.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety. Additional advantages and features of the present invention are apparent in U.S. Application No. 62/018,794 and U.S. Application No. 62/018,822, the specifications of which are incorporated herein in their entirety by reference.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

What is claimed:

1. A suspended lipid system comprising:

a. a supporting substrate having a substrate surface and an aperture;

b. a modified lipid membrane comprising a plurality of non-polymerizable lipid monomers and a plurality of hydrophobic non-lipid monomers dissolved in an organic solvent to form a solution, wherein said solution is disposed on the substrate such that the lipid monomers form a planar lipid bilayer suspended across the aperture, wherein the non-lipid monomers are disposed in the suspended planar lipid bilayer and polymerized to stabilize the suspended planar lipid bilayer; and c. one or more protein ion channels disposed through the suspended planar lipid bilayer.

2. The system of claim 1, wherein the lipid bilayer is suspended across the aperture such that a first lipid leaflet and a second lipid leaflet of the lipid bilayer are both disposed above or below the aperture.

3. The system of claim 1, wherein the lipid bilayer is suspended across the aperture such that a first lipid leaflet of the lipid bilayer is disposed above the aperture and a second lipid leaflet of the lipid bilayer is disposed below the aperture.

4. The system of claim 1, wherein the supporting substrate is constructed from a material selected from a group consisting of a glass, a polymeric material, an epoxy, or a metal oxide.

5. The system of claim 1, wherein an energy modifying layer is disposed on the substrate surface at or near the aperture, wherein the energy modifying layer is disposed between the lipid monomers and the substrate surface, wherein the energy modifying layer lowers a surface energy of the substrate surface.

6. The system of claim 5, wherein the energy modifying layer lowers the surface energy of the supporting substrate to less than about 40 $mJ/m^2$.

7. The system of claim 6, wherein the energy modifying layer is a silane-modified layer, wherein the silane-modified layer comprises an alkylated silane.

8. The system of claim 7, wherein the alkylated silane is selected from a group consisting of (tridecafluoro 1, 1, 2, 2-tetrahydrooctyl)-dimethylchlorosilane (PFDCS), (heptadecafluoro 1, 1, 2, 2-tetrahydrodecyl)-dimethylchlorosilane (PFDDCS) (tridecafluoro 1, 1, 2, 2-tetrahydrooctyl)-trichlorosilane (PFTCS), 3-cyanopropyldimethylchlorosilane (CPDCS), ethyldimethylchlorosilane (EDCS), aminopropyldimethylethoxyosilane (APDES), 3,3,3-trifluoropropyldimethylchlorosilane (FPDCS), or n-octyldimethylchlorosilane (ODCS).

9. The system of claim 1, wherein the substrate surface has a surface energy of less than about 40 $mJ/m^2$.

10. The system of claim 1, wherein the non-lipid monomers comprise a methacrylate and a cross-linking agent.

11. The system of claim 10, wherein the methacrylate is an aliphatic methacrylate or an aromatic methacrylate.

12. The system of claim 11, wherein the aromatic methacrylate is a benzyl methacrylate or a naphthyl methacrylate.

13. The system of claim 10, wherein the cross-linking agent is a dimethacrylate.

14. The system of claim 13, wherein the dimethacrylate is ethylene glycol dimethacrylate.

15. The system of claim 1, wherein a ratio of the non-polymerizable lipid monomers to the non-lipid monomers is 1:2, wherein a breakdown voltage of the modified lipid membrane is at least 1,250 mV, wherein an air-to-water transfer (AWT) count of the modified lipid membrane is at least 20, and wherein a lifetime of the modified lipid membrane is at least 24 hours.

16. The system of claim 1, wherein the lipid monomers are cell membrane fragments, 1,2-diphytanoyl-sn-glycero-3-phosphocholine monomers, naturally occurring lipids, or synthetic lipids.

17. The system of claim 1, wherein the non-lipid monomers are polymerized by UV irradiation, visible irradiation, gamma irradiation, redox polymerization, or thermal polymerization.

18. The system of claim 17, wherein the modified lipid membrane further comprises photoinitiators, wherein the non-lipid monomers are polymerized by UV or visible irradiation, wherein a breakdown voltage of the modified lipid membrane is at least 1,250 mV.

19. The system of claim 18, wherein the duration of UV or visible irradiation is sufficient to photopolymerize the non-lipid monomers.

20. The system of claim 17, wherein the non-lipid monomers are polymerized by redox polymerization, wherein a redox polymerization mixture comprises an initiator-buffer component and $NaHSO_3$.

21. The system of claim 20, wherein the initiator-buffer component comprises ammonium persulfate, wherein a mole ratio of ammonium persulfate, $NaHSO_3$, and lipid monomers is between about 10-500:10-500:1.

22. The system of claim 17, wherein redox polymerization occurs at a near neutral pH.

23. The system of claim 17, wherein the redox polymerization occurs at a pH between about 5 to 9.

24. A suspended lipid system comprising:

a. a supporting substrate having a substrate surface and an aperture, wherein an energy modifying layer is disposed on the substrate surface at or near the aperture, wherein the energy modifying layer lowers a surface energy of the substrate surface;

b. a modified lipid membrane comprising a plurality of non-polymerizable lipid monomers and a plurality of polymerizable, hydrophobic non-lipid monomers dissolved in an organic solvent to form a solution, the non-lipid monomers comprising a methacrylate and a cross-linking agent, wherein the solution is disposed on the substrate such that the lipid monomers form a planar lipid bilayer suspended across the aperture, wherein the energy modifying layer is disposed between the lipid monomers and the substrate surface, wherein the non-lipid monomers are disposed in the suspended planar lipid bilayer and polymerized to stabilize the suspended planar lipid bilayer; and c. one or more protein ion channels disposed through the suspended planar lipid bilayer;

wherein the plurality of polymerizable, hydrophobic non-lipid monomers are polymerized by redox polymerization using a redox polymerization mixture comprising an initiator-buffer component and $NaHSO_3$, wherein redox polymerization occurs at a near neutral pH.

25. The system of claim 24, wherein a ratio of the non-polymerizable lipid monomers to the non-lipid monomers is 1:2, wherein a breakdown voltage of the modified lipid membrane is at least 1,250 mV, wherein an air-to-water transfer (AWT) count of the modified lipid membrane is at least 20, and wherein a lifetime of the modified lipid membrane is at least 24 hours.

26. A stabilized suspended lipid system comprising: a supporting substrate having a substrate aperture and a stabilized, planar lipid bilayer suspended across the aperture, wherein the stabilized, planar lipid bilayer has a polymer scaffold and protein ion channels disposed therein, wherein the stabilized, planar lipid bilayer is formed by:

a. preparing a monomer mixture comprising non-polymerizable lipid monomers and polymerizable, hydrophobic non-lipid monomers, dissolved in an organic solvent;

b. adding the monomer mixture to the substrate aperture, wherein the non-polymerizable lipid monomers form a planar lipid bilayer suspended across the aperture, wherein the polymerizable, hydrophobic non-lipid monomers are disposed in the suspended planar lipid bilayer to form a modified lipid membrane;

c. polymerizing the non-lipid monomers to produce the polymer scaffold that stabilizes the modified lipid membrane; and d. inserting one or more proteins through the lipid membrane to form the protein ion channels.

27. The system of claim 26, wherein a ratio of the non-polymerizable lipid monomers to the non-lipid monomers is 1:2, wherein a breakdown voltage of the modified lipid membrane is at least 1,250 mV, wherein an air-to-water transfer (AWT) count of the modified lipid membrane is at least 20, and wherein a lifetime of the modified lipid membrane is at least 24 hours.

28. A method of enhancing stability of a suspended lipid membrane, said method comprising:

a. providing a supporting substrate having a substrate surface and an aperture;

b. preparing a monomer mixture comprising non-polymerizable lipid monomers and polymerizable, hydrophobic non-lipid monomers, dissolved in an organic solvent;

c. adding the monomer mixture to the substrate aperture, wherein the non-polymerizable lipid monomers form a planar lipid bilayer suspended across the aperture, wherein the polymerizable, hydrophobic non-lipid monomers are disposed in the suspended planar lipid bilayer to form a modified lipid membrane;

d. polymerizing the non-lipid monomers to stabilize the modified lipid membrane; and e. inserting one or more proteins through the lipid membrane to form protein ion channels.

29. The method of claim 28, wherein a ratio of the non-polymerizable lipid monomers to the non-lipid monomers is 1:2, wherein a breakdown voltage of the modified lipid membrane is at least 1,250 m, wherein an air-to-water transfer (AWT) count of the modified lipid membrane is at least 20, and wherein a lifetime of the modified lipid membrane is at least 24 hours.

30. A method of enhancing stability of a suspended lipid membrane, said method comprising:

a. depositing an energy modifying layer on a substrate surface at or near an aperture of a supporting substrate, wherein the energy modifying layer lowers a surface energy of the substrate surface;

b. preparing a monomer mixture comprising non-polymerizable lipid monomers and polymerizable, hydrophobic non-lipid monomers, dissolved in an organic solvent;

c. adding the monomer mixture to the substrate aperture, wherein the non-polymerizable lipid monomers form a planar lipid bilayer suspended across the aperture, wherein the polymerizable, hydrophobic non-lipid monomers are disposed in the suspended planar lipid bilayer to form a modified lipid membrane;

d. polymerizing the non-lipid monomers to stabilize the modified lipid membrane; and e. inserting one or more proteins through the lipid membrane to form protein ion channels.

31. The method of claim 30, wherein a ratio of the non-polymerizable lipid monomers to the non-lipid monomers is 1:2, wherein a breakdown voltage of the modified lipid membrane is at least 1,250 mV, wherein an air-to-water transfer (AWT) count of the modified lipid membrane is at least 20, and wherein a lifetime of the modified lipid membrane is at least 24 hours.

32. A method of enhancing stability of a suspended lipid membrane, said method comprising:

a. depositing an energy modifying layer on a substrate surface at or near an aperture of a supporting substrate, wherein the energy modifying layer lowers a surface energy of the substrate surface;

b. preparing a monomer mixture comprising non-polymerizable lipid monomers and polymerizable, hydrophobic non-lipid monomers, dissolved in an organic solvent, wherein the non-lipid monomers comprises a methacrylate and a cross-linking agent;

c. adding the monomer mixture to the substrate aperture, wherein the non-polymerizable lipid monomers form a planar lipid bilayer suspended across the aperture, wherein the energy modifying layer is disposed between the lipid monomers and the substrate surface, wherein the polymerizable, hydrophobic non-lipid monomers are disposed in the suspended planar lipid bilayer to form a modified lipid membrane;

d. polymerizing the non-lipid monomers using a redox polymerization mixture to stabilize the modified lipid membrane, wherein the redox polymerization mixtures comprises an initiator-buffer component and $NaHSO_3$, wherein redox polymerization occurs at a near neutral pH; and e. inserting one or more proteins through the lipid membrane to form protein ion channels.

33. The method of claim 32, wherein a ratio of the non-polymerizable lipid monomers to the non-lipid monomers is 1:2, wherein a breakdown voltage of the modified lipid membrane is at least 1,250 mV, wherein an air-to-water transfer (AWT) count of the modified lipid membrane is at least 20, and wherein a lifetime of the modified lipid membrane is at least 24 hours.

* * * * *